US011680276B2

(12) United States Patent
Ali et al.

(10) Patent No.: US 11,680,276 B2
(45) Date of Patent: Jun. 20, 2023

(54) COMPOSITIONS AND METHODS FOR TREATING RETINAL DISORDERS

(71) Applicant: UCL BUSINESS LTD, London (GB)

(72) Inventors: Robin Ali, London (GB); Takaaki Matsuki, London (GB); Alexander Smith, London (GB); Anastasios Georgiadis, London (GB)

(73) Assignee: UCL BUSINESS LTD., London (GB)

( * ) Notice: Subject to any disclaimer, the term of this patent is extended or adjusted under 35 U.S.C. 154(b) by 36 days.

(21) Appl. No.: 16/961,857

(22) PCT Filed: Jan. 14, 2019

(86) PCT No.: PCT/GB2019/050092
§ 371 (c)(1),
(2) Date: Jul. 13, 2020

(87) PCT Pub. No.: WO2019/138250
PCT Pub. Date: Jul. 18, 2019

(65) Prior Publication Data
US 2020/0392536 A1 Dec. 17, 2020

(30) Foreign Application Priority Data
Jan. 12, 2018 (GB) ..................................... 1800546

(51) Int. Cl.

| | |
|---|---|
| ***C12N 15/861*** | (2006.01) |
| ***A61K 35/761*** | (2015.01) |
| ***A61P 27/02*** | (2006.01) |
| ***A61K 39/235*** | (2006.01) |

(52) U.S. Cl.
CPC .......... *C12N 15/861* (2013.01); *A61K 35/761* (2013.01); *A61K 39/235* (2013.01); *A61P 27/02* (2018.01)

(58) Field of Classification Search
None
See application file for complete search history.

(56) References Cited

U.S. PATENT DOCUMENTS 11,021,519 B2 * 6/2021 Chalberg, Jr. ..... A61K 48/0066

FOREIGN PATENT DOCUMENTS

WO 2011034947 A2 3/2011
WO 2015142941 A1 9/2015

OTHER PUBLICATIONS

Sengillo et al., Gene and Cell-Based Therapies for Inherited Retinal Disorders, Am J Med Genet C Semin Med Genet 172(4): 349-366 (Year: 2016).*
Remmer et al. ("Achromatopsia: a review," Curr Opin Ophthalmol 26: 333-340 (Year: 2015).*
Smallwood, P. M. et al., "Role of a Locus Control Region in the Mutually Exclusive Expression of Human Red and Green Cone Pigment Cones"; PNAS USA (2002); vol. 99:2; pp. 1008-1011.
Dai, X. et al., "Long-Term Retinal Cone Rescue using a Capsid Mutant AAV8 Vector in a Mouse Model of CNGA3-Achromatopsia"; PLOS One (2017); vol. 12:11; pp. e0188032 (16 pgs).
(Continued)

*Primary Examiner* — M Franco G Salvoza
(74) *Attorney, Agent, or Firm* — Fox Rothschild LLP

(57) ABSTRACT

The present invention relates to the prevention and/or treatment of retinal disorders, such as cone dystrophies, cone-rod dystrophies, in particular Achromatopsia.

42 Claims, 13 Drawing Sheets

Specification includes a Sequence Listing.

(56) References Cited

OTHER PUBLICATIONS

Alexander, J. J. et al., "Restoration of Cone Vision in a Mouse Model of Achromatopsia"; Nature Medicine (2007); vol. 13:6' pp. 685-687.
Ye, G. et al., "Cone-Specific Promoters for Gene Therapy of Achromatopsia and Other Retinal Diseases"; Human Gene Therapy (2016); vol. 27:1.; pp. 72-82.
Komaromy, A. M. et al., "Gene Therapy Rescues Cone Function in Congenital Achromatopsia"; Human Molecular Genetics (2010); vol. 19:13; pp. 2581-2593.

* cited by examiner

A

B

A

B

C

A

B

SEQUENCE LISTING

<160> NUMBER OF SEQ ID NOS: 17

<210> SEQ ID NO 1
<211> LENGTH: 1253
<212> TYPE: DNA
<213> ORGANISM: Artificial Sequence
<220> FEATURE:
<223> OTHER INFORMATION: 1.2 kb fragment of the M/L opsin Locus Control
Region (LCR)

<400> SEQUENCE: 1
taggaataga agggtgggtg caggaggctg aggggtgggg aaagggcatg ggtgtttcat 60
gaggacagag cttccgtttc atgcaatgaa aagagtttgg agacggatgg tggtgactgg 120

-continued

```
actatacact tacacacggt agcgatggta cactttgtat tatgtatatt ttaccacgat    180

ctttttaaag tgtcaaaggc aaatggccaa atggttcctt gtcctatagc tgtagcagcc    240

atcggctgtt agtgacaaag cccctgagtc aagatgacag cagcccccat aactcctaat    300

cggctctccc gcgtggagtc atttaggagt agtcgcatta gagacaagtc caacatctaa    360

tcttccaccc tggccagggc cccagctggc agcgagggtg ggagactccg ggcagagcag    420

agggcgctga cattggggcc cggcctggct tgggtccctc tggcctttcc ccaggggccc    480

tctttccttg gggctttctt gggccgccac tgctcccgct cctctccccc catcccaccc    540

cctcaccccc tcgttcttca tatccttctc tagtgctccc tccactttca tccacccttc    600

tgcaagagtg tgggaccaca aatgagtttt cacctggcct ggggacacac gtgcccccac    660

aggtgctgag tgactttcta ggacagtaat ctgctttagg ctaaaatggg acttgatctt    720

ctgttagccc taatcatcaa ttagcagagc cggtgaaggt gcagaaccta ccgcctttcc    780

aggcctcctc ccacctctgc cacctccact ctccttcctg ggatgtgggg gctggcacac    840

gtgtggccca gggcattggt gggattgcac tgagctgggt cattagcgta atcctggaca    900

agggcagaca gggcgagcgg agggccagct ccggggctca ggcaaggctg gggggcttccc   960

ccagacaccc cactcctcct ctgctggacc cccacttcat agggcacttc gtgttctcaa   1020

agggcttcca aatagcatgg tggccttgga tgcccaggga agcctcagag ttgcttatct   1080

ccctctagac agaaggggaa tctcggtcaa gagggagagg tcgccctgtt caaggccacc   1140

cagccagctc atggcggtaa tgggacaagg ctggccagcc atcccaccct cagaagggac   1200

ccggtggggc aggtgatctc agaggaggct cacttctggg tctcacattc ttg           1253
```

<210> SEQ ID NO 2
<211> LENGTH: 1970
<212> TYPE: DNA
<213> ORGANISM: Artificial Sequence
<220> FEATURE:
<223> OTHER INFORMATION: 2.0 kb M opsin promoter fragment, with no M8 sequence

<400> SEQUENCE: 2

```
taaaaagcaa gtcttgccag ggcagtggtg tgcacctgtg gtcccagcta ctcaggatgc     60

tgaggcagga ggattacttg tgcccagcaa gtagaggctg cagtgacctg tgactgtgct    120

actgccctcc aacctgggtg acagagtgag accttgtctc aaaaaaaaaa gagcgggggg    180

gggggccgg gccgggcgtg gtggctcaca gctgtaatcc cagcactttg ggaagccaag    240

gcgggtggat cacttgaggt caggagtttg agaccatcat ggtcaacact gcgaaacact    300

gtccctacta aaaatacaaa aattagccgg gcatggtggc acacacctgt aatcccagct    360

actggggagg ctgaggcagg agaattgctt gagccgggga gacggaggtt gcagtgagcc    420

gagactgcgc cactgcactc cagcctgact gacaagagtg agattgtctc aaaaaaaaaa    480

aaaaagtaat cactagaaaa gaagctacat atgtacataa catccaaata accaagagga    540

gaaaaaaatg ggacttgatt aatcaaaaca aaaacaaaaa agaaagaaag aaagggggag    600

aaaataaaac aagggctggg tgtgctggct catgcctgta atcccagcac tttggaagcc    660

aaggtgggtg gatctcttga gctcaggagg tcaagaccag cctgggcaac atggcgaaac    720

cccgtctcta ttaaaaaaaa aattaataca acaattatcc tggagtggtg gtgcacacct    780

gtagtcccag ctacccagga cgctgagacg ggaggatcgc ttgatcccgg ggatgtcgag    840

gctgccgtga tcgcaccact gccctccagc cagggtggca gactgagacc ccatctcaaa    900
```

-continued

```
aaataaataa ataaaagcaa acaagaaaaa aaaaggcttg aaacatatct gatagataaa    960

gggctaatca acacaatata taaagaactg caaatcagta aactaagagc aaataaccca   1020

atataaagac attaaagggt agccacggac atctcagacg acgaaaaaca aaagacagta   1080

aacgtataat aaaacatgta attgcaaggt gatccgggaa tagtaagcga aaagcaacaa   1140

ttaaatacta ttttctcatc caccagaacg ccaaaaatta aaaagcctaa caatgtccag   1200

ggctggcgag aatgtggcag aaggtgatgt cacataccct gcaagtggga atctaaacag   1260

attcagggtt ttggtttttt tttaatcgca attaggtggc ctgttaaatt ttttttcttg   1320

agacagagtt ttgctcttgt tgcccaggct ggagtgcaat ggctcgatct tggctcaccg   1380

caacctcgac ctcccaggta caagcgattc tcctgtctca gcctcccaag tagctgggag   1440

tacaggtatt tgccactaag cccagctaat tgttttttat ttagtagaaa cggggtttca   1500

ccatgttagt caggctggtc gggaactcct gacctcagga gatctacccg ccttggcctc   1560

ccaaagtgct gggattacag gcgtgtgcca ctgtgcccag ccactttttt ttagacagag   1620

tcttggtctg ttgcccaggc tagagttcag tggcgccatc tcagctcact gcaacctccg   1680

cctcccagat tcaagcgatt ctcctgcctc gacctcccag tagctgggat tacaggtttc   1740

cagcaaatcc ctctgagccg cccccggggg ctcgcctcag gagcaaggaa gcaaggggtg   1800

ggaggaggag gtctaagtcc caggcccaat taagagatca gatggtgtag gatttgggag   1860

cttttaaggt gaagaggccc gggctgatcc cactggccgg tataaagcac cgtgaccctc   1920

aggtgacgca ccagggccgg ctgccgtcgg ggacagggct ttccatagcc              1970
```

<210> SEQ ID NO 3
<211> LENGTH: 529
<212> TYPE: DNA
<213> ORGANISM: Artificial Sequence
<220> FEATURE:
<223> OTHER INFORMATION: 500 bp M opsin fragment, with M8 mutation

<400> SEQUENCE: 3

```
acaggtattt gccactaagc ccagctaatt gttttttatt tagtagaaac ggggtttcac     60

catgttagtc aggctggtcg ggaactcctg acctcaggag atctacccgc cttggcctcc    120

caaagtgctg ggattacagg cgtgtgccac tgtgcccagc cacttttttt tagacagagt    180

cttggtctgt tgcccaggct agagttcagt ggcgccatct cagctcactg caacctccgc    240

ctcccagatt caagcgattc tcctgcctcg acctcccagt agctgggatt acaggtttcc    300

agcaaatccc tctgagccgc ccccgggggc tcgcctcagg agcaaggaag caaggggtgg    360

gaggaggagg tctaagtccc aggcccaatt aagagatcag atggtgtagg atttgggagc    420

ttttaaggtg aagaggcccg ggctgatccc actggccggt ataaagcacc gtgaccctca    480

ggtgacgcac catctagagc tgccgtcggg gacagggctt tccatagcc               529
```

<210> SEQ ID NO 4
<211> LENGTH: 1782
<212> TYPE: DNA
<213> ORGANISM: Artificial Sequence
<220> FEATURE:
<223> OTHER INFORMATION: variant of hG1.7 construct, 1.2 kb M/L opsin
      LCR fragment, 500 bp M opsin fragment, with M8 mutation

<400> SEQUENCE: 4

```
taggaataga agggtgggtg caggaggctg aggggtgggg aaagggcatg ggtgtttcat     60

gaggacagag cttccgtttc atgcaatgaa aagagtttgg agacggatgg tggtgactgg    120
```

```
actatacact tacacacggt agcgatggta cactttgtat tatgtatatt ttaccacgat    180
ctttttaaag tgtcaaaggc aaatggccaa atggttcctt gtcctatagc tgtagcagcc    240
atcggctgtt agtgacaaag cccctgagtc aagatgacag cagcccccat aactcctaat    300
cggctctccc gcgtggagtc atttaggagt agtcgcatta gagacaagtc caacatctaa    360
tcttccaccc tggccagggc cccagctggc agcgagggtg ggagactccg ggcagagcag    420
agggcgctga cattggggcc cggcctggct tgggtccctc tggcctttcc ccaggggccc    480
tctttccttg gggctttctt gggccgccac tgctcccgct cctctccccc catcccaccc    540
cctcaccccc tcgttcttca tatccttctc tagtgctccc tccactttca tccacccttc    600
tgcaagagtg tgggaccaca aatgagtttt cacctggcct ggggacacac gtgcccccac    660
aggtgctgag tgactttcta ggacagtaat ctgctttagg ctaaaatggg acttgatctt    720
ctgttagccc taatcatcaa ttagcagagc cggtgaaggt gcagaaccta ccgcctttcc    780
aggcctcctc ccacctctgc cacctccact ctccttcctg ggatgtgggg gctggcacac    840
gtgtggccca gggcattggt gggattgcac tgagctgggt cattagcgta atcctggaca    900
agggcagaca gggcgagcgg agggccagct ccggggctca ggcaaggctg gggggcttccc    960
ccagacaccc cactcctcct ctgctggacc cccacttcat agggcacttc gtgttctcaa   1020
agggcttcca aatagcatgg tggccttgga tgcccaggga agcctcagag ttgcttatct   1080
ccctctagac agaaggggaa tctcggtcaa gagggagagg tcgccctgtt caaggccacc   1140
cagccagctc atggcggtaa tgggacaagg ctggccagcc atcccaccct cagaagggac   1200
ccggtggggc aggtgatctc agaggaggct cacttctggg tctcacattc ttgacaggta   1260
tttgccacta agcccagcta attgtttttt atttagtaga aacggggttt caccatgtta   1320
gtcaggctgg tcgggaactc ctgacctcag gagatctacc cgccttggcc tcccaaagtg   1380
ctgggattac aggcgtgtgc cactgtgccc agccactttt ttttagacag agtcttggtc   1440
tgttgcccag gctagagttc agtggcgcca tctcagctca ctgcaacctc cgcctcccag   1500
attcaagcga ttctcctgcc tcgacctccc agtagctggg attacaggtt tccagcaaat   1560
ccctctgagc cgcccccggg ggctcgcctc aggagcaagg aagcaagggg tgggaggagg   1620
aggtctaagt cccaggccca attaagagat cagatggtgt aggatttggg agcttttaag   1680
gtgaagaggc ccgggctgat cccactggcc ggtataaagc accgtgaccc tcaggtgacg   1740
caccatctag agctgccgtc ggggacaggg ctttccatag cc                      1782
```

<210> SEQ ID NO 5
<211> LENGTH: 247
<212> TYPE: DNA
<213> ORGANISM: Artificial Sequence
<220> FEATURE:
<223> OTHER INFORMATION: 200 bp M opsin fragment, with M8 mutation

<400> SEQUENCE: 5

```
gatcgattac aggtttccag caaatccctc tgagccgccc ccgggggctc gcctcaggag     60
caaggaagca aggggtggga ggaggaggtc taagtcccag gcccaattaa gagatcagat    120
ggtgtaggat ttgggagctt ttaaggtgaa gaggcccggg ctgatcccac tggccggtat    180
aaagcaccgt gaccctcagg tgacgcacca tctagagctg ccgtcgggga cagggctttc    240
catagcc                                                              247
```

<210> SEQ ID NO 6
<211> LENGTH: 1500

<212> TYPE: DNA
<213> ORGANISM: Artificial Sequence
<220> FEATURE:
<223> OTHER INFORMATION: hG1.4 construct: 1.2 kb M/L opsin LCR fragment, 200bp M opsin fragment, with M8 mutation

<400> SEQUENCE: 6

```
taggaataga agggtgggtg caggaggctg aggggtgggg aaagggcatg ggtgtttcat      60
gaggacagag cttccgtttc atgcaatgaa aagagtttgg agacggatgg tggtgactgg     120
actatacact tacacacggt agcgatggta cactttgtat tatgtatatt ttaccacgat     180
ctttttaaag tgtcaaaggc aaatggccaa atggttcctt gtcctatagc tgtagcagcc     240
atcggctgtt agtgacaaag cccctgagtc aagatgacag cagcccccat aactcctaat     300
cggctctccc gcgtggagtc atttaggagt agtcgcatta gagacaagtc caacatctaa     360
tcttccaccc tggccagggc cccagctggc agcgagggtg ggagactccg ggcagagcag     420
agggcgctga cattggggcc cggcctggct tgggtccctc tggcctttcc ccaggggccc     480
tctttccttg ggctttcttg ggccgccac tgctcccgct cctctccccc catcccaccc     540
cctcaccccc tcgttcttca tatccttctc tagtgctccc tccactttca tccacccttc     600
tgcaagagtg tgggaccaca aatgagtttt cacctggcct ggggacacac gtgcccccac     660
aggtgctgag tgactttcta ggacagtaat ctgctttagg ctaaaatggg acttgatctt     720
ctgttagccc taatcatcaa ttagcagagc cggtgaaggt gcagaaccta ccgcctttcc     780
aggcctcctc ccacctctgc cacctccact ctccttcctg ggatgtgggg gctggcacac     840
gtgtggccca gggcattggt gggattgcac tgagctgggt cattagcgta atcctggaca     900
agggcagaca gggcgagcgg agggccagct ccggggctca ggcaaggctg gggcttccc     960
ccagacaccc cactcctcct ctgctggacc cccacttcat agggcacttc gtgttctcaa    1020
agggcttcca aatagcatgg tggccttgga tgcccaggga agcctcagag ttgcttatct    1080
ccctctagac agaaggggaa tctcggtcaa gagggagagg tcgccctgtt caaggccacc    1140
cagccagctc atggcggtaa tgggacaagg ctggccagcc atcccaccct cagaagggac    1200
ccggtggggc aggtgatctc agaggaggct cacttctggg tctcacattc ttggatcgat    1260
tacaggtttc cagcaaatcc ctctgagccg cccccggggg ctcgcctcag gagcaaggaa    1320
gcaaggggtg ggaggaggag gtctaagtcc caggcccaat taagagatca gatggtgtag    1380
gatttgggag cttttaaggt gaagaggccc gggctgatcc cactggccgg tataaagcac    1440
cgtgaccctc aggtgacgca ccatctagag ctgccgtcgg ggacagggct ttccatagcc    1500
```

<210> SEQ ID NO 7
<211> LENGTH: 2085
<212> TYPE: DNA
<213> ORGANISM: Artificial Sequence
<220> FEATURE:
<223> OTHER INFORMATION: non-codon optimised CNGA3 cDNA

<400> SEQUENCE: 7

```
atggccaaga tcaacaccca atactcccac ccctccagga cccacctcaa ggtaaagacc      60
tcagaccgag atctcaatcg cgctgaaaat ggcctcagca gagcccactc gtcaagtgag     120
gagacatcgt cagtgctgca gccggggatc gccatggaga ccagaggact ggctgactcc     180
gggcagggct ccttcaccgg ccaggggatc gccaggctgt cgcgcctcat cttcttgctg     240
cgcaggtggg ctgccaggca tgtgcaccac caggaccagg gaccggactc ttttcctgat     300
cgtttccgtg gagccgagct taaggaggtg tccagccaag aaagcaatgc ccaggcaaat     360
```

```
gtgggcagcc aggagccagc agacagaggg agaagcgcct ggcccctggc caaatgcaac    420

actaacacca gcaacaacac ggaggaggag aagaagacga aaaagaagga tgcgatcgtg    480

gtggacccgt ccagcaacct gtactaccgc tggctgaccg ccatcgccct gcctgtcttc    540

tataactggt atctgcttat ttgcagggcc tgtttcgatg agctgcagtc cgagtacctg    600

atgctgtggc tggtcctgga ctactcggca gatgtcctgt atgtcttgga tgtgcttgta    660

cgagctcgga caggttttct cgagcaaggc ttaatggtca gtgataccaa caggctgtgg    720

cagcattaca agacgaccac gcagttcaag ctggatgtgt tgtccctggt ccccaccgac    780

ctggcttact taaaggtggg cacaaactac ccagaagtga ggttcaaccg cctactgaag    840

ttttcccggc tctttgaatt ctttgaccgc acagagacaa ggaccaacta ccccaatatg    900

ttcaggattg ggaacttggt cttgtacatt ctcatcatca tccactggaa tgcctgcatc    960

tactttgcca tttccaagtt cattggtttt gggacagact cctgggtcta cccaaacatc   1020

tcaatcccag agcatgggcg cctctccagg aagtacattt acagtctcta ctggtccacc   1080

ttgaccctta ccaccattgg tgagacccca ccccccgtga aagatgagga gtatctcttt   1140

gtggtcgtag acttcttggt gggtgttctg atttttgcca ccattgtggg caatgtgggc   1200

tccatgatct cgaatatgaa tgcctcacgg gcagagttcc aggccaagat tgattccatc   1260

aagcagtaca tgcagttccg caaggtcacc aaggacttgg agacgcgggt tatccggtgg   1320

tttgactacc tgtgggccaa caagaagacg gtggatgaga aggaggtgct caagagcctc   1380

ccagacaagc tgaaggctga gatcgccatc aacgtgcacc tggacacgct gaagaaggtt   1440

cgcatcttcc aggactgtga ggcagggctg ctggtggagc tggtgctgaa gctgcgaccc   1500

actgtgttca gccctgggga ttatatctgc aagaagggag atattgggaa ggagatgtac   1560

atcatcaacg agggcaagct ggccgtggtg gctgatgatg gggtcaccca gttcgtggtc   1620

ctcagcgatg gcagctactt cggggagatc agcattctga acatcaaggg gagcaagtcg   1680

gggaaccgca ggacggccaa catccgcagc attggctact cagacctgtt ctgcctctca   1740

aaggacgatc tcatggaggc cctcaccgag taccccgaag ccaagaaggc cctggaggag   1800

aaaggacggc agatcctgat gaaagacaac ctgatcgatg aggagctggc cagggcgggc   1860

gcggacccca aggaccttga ggagaaagtg gagcagctgg ggtcctccct ggacaccctg   1920

cagaccaggt ttgcacgcct cctggctgag tacaacgcca cccagatgaa gatgaagcag   1980

cgtctcagcc aactggaaag ccaggtgaag ggtggtgggg acaagcccct ggctgatggg   2040

gaagttcccg gggatgctac aaaaacagag gacaaacaac agtga                   2085
```

<210> SEQ ID NO 8
<211> LENGTH: 2085
<212> TYPE: DNA
<213> ORGANISM: Artificial Sequence
<220> FEATURE:
<223> OTHER INFORMATION: codon-optimised CNGA3 cDNA

<400> SEQUENCE: 8

```
atggcaaaaa tcaataccca gtacagccac ccctcacgaa ctcacctgaa agtcaaaaca     60

agcgatagag acctgaacag agccgagaac ggcctgtcca gggcccacag ctcctctgag    120

gaaactagtt cagtgctgca gcctggaatc gctatggaga ccagagggct ggctgactct    180

ggccaaggaa gtttcacagg gcagggcatc gccaggctgt ctagactgat tttctgctg     240

aggagatggg ccgctaggca tgtgcaccat caggaccagg gacccgatag tttccctgac    300
```

```
aggttcaggg gggccgaact gaaggaggtc agctcccagg aatctaacgc acaggccaat    360
gtgggcagtc aggagcccgc tgatagagga cggtccgcat ggcctctggc caagtgcaac    420
actaatacct ctaacaatac agaggaagag aagaaaacta agaaaaagga tgccatcgtg    480
gtcgaccctt ctagtaacct gtactatagg tggctgacag ctatcgcact gccagtgttc    540
tacaattggt atctgctgat ttgcagagct tgttttgacg aactgcagag tgagtatctg    600
atgctgtggc tggtgctgga ttactcagca gacgtgctgt atgtgctgga tgtcctggtg    660
cgcgcacgaa ctgggttcct ggagcagggc ctgatggtga gcgacaccaa cagactgtgg    720
cagcactaca aaaccacaac tcagtttaag ctggatgtcc tgtccctggt gccaaccgac    780
ctggcctacc tgaaagtcgg cacaaactat cccgaggtgc ggttcaatcg cctgctgaag    840
ttctctcggc tgtttgagtt cttcgatagg acagagacta gaaccaacta cccaaatatg    900
ttccgcatcg gcaacctggt gctgtatatt ctgatcatta tccactggaa tgcttgtatc    960
tactttgcaa tcagcaagtt cattggattt gggaccgaca gctgggtgta tccaaacatt   1020
tccatccccg aacatggacg actgagcagg aagtacatct attcactgta ctggagcaca   1080
ctgactctga ccacaattgg ggagaccccc cctccagtga aggatgaaga gtacctgttc   1140
gtggtcgtgg actttctggt cggcgtgctg atcttcgcaa caattgtcgg caatgtggga   1200
agtatgatct caaacatgaa tgcctcacga gctgagttcc aggctaaaat tgacagcatc   1260
aagcagtata tgcagtttag aaaagtcact aaggatctgg agaccagagt gatccggtgg   1320
tttgactacc tgtgggccaa caaaaagaca gtcgatgaaa aagaggtgct gaagagcctg   1380
cccgacaaac tgaaggcaga gattgccatc aatgtccatc tggatactct gaaaaaggtg   1440
cggatcttcc aggactgcga agcaggactg ctggtcgagc tggtgctgaa gctgcgccct   1500
accgtgttta gcccaggcga ttatatctgt aaaaaggggg acattggcaa agaaatgtac   1560
attatcaacg aggggaagct ggctgtcgtg gcagacgatg gcgtgaccca gttcgtcgtg   1620
ctgagcgatg gcagctattt tggggaaatt tccatcctga atatcaaagg ctccaagtct   1680
ggaaaccggc gcacagctaa tattcggtcc atcggatatt ctgacctgtt ctgcctgtct   1740
aaggacgatc tgatggaggc actgactgaa taccccgagg ccaaaaaggc tctggaagag   1800
aaaggccggc agatcctgat gaaggataac ctgattgacg aagagctggc acgagctgga   1860
gcagacccta aagatctgga agagaaggtg gagcagctgg gatcaagcct ggataccctg   1920
cagacacgct tcgctcgact gctggcagaa tacaatgcca cccagatgaa aatgaagcag   1980
cgcctgagtc agctggagtc acaggtgaaa ggcggagggg acaagcccct ggcagatggc   2040
gaagtccctg gcgacgctac aaaaacagaa gataaacagc agtaa                   2085
```

<210> SEQ ID NO 9
<211> LENGTH: 2577
<212> TYPE: DNA
<213> ORGANISM: Artificial Sequence
<220> FEATURE:
<223> OTHER INFORMATION: PDE6C cDNA, NM_006204.3

<400> SEQUENCE: 9

```
atgggtgaga tcaaccaagt tgccgtggag aaatacctgg aggagaaccc tcagtttgcc     60
aaggagtact ttgacaggaa gttgcgggtg gaggtgctgg gagaaatctt caagaacagc    120
caggtgccag tccagtccag catgtccttc tctgagctga cccaggtgga ggagtcagcc    180
ctgtgcttgg agctgctgtg gaccgtgcag gaggaggggg gcaccccaga gcagggggtt    240
cacagggccc tgcagaggct ggcccacctg ctccaggctg accgctgcag catgttcctg    300
```

```
tgccggtccc ggaacggcat acctgaggtg gcctctaggt tgctggatgt cacccccacc    360
tccaagtttg aggacaacct ggtgggccct gacaaagaag ttgtgtttcc attggacatt    420
gggatagtgg gttgggctgc tcacacgaag aaaactcata atgtcccaga tgtgaaaaag    480
aacagccatt tttctgactt catggacaag caaactgggt atgtcactaa gaacctgctg    540
gcaaccccga tcgtggtggg caaggaggtt cttgctgtga tcatggcagt taacaaagta    600
aatgcatctg aattttccaa acaggatgaa gaggtctttt ccaaatacct caactttgtg    660
tctatcatcc taaggcttca tcacaccagc tacatgtaca atattgaatc ccgaagaagc    720
cagatcctta tgtggtcagc caataaagta tttgaagaac tcacagatgt tgagcgacag    780
tttcacaaag cgctctacac ggttagatca tatctgaact gtgaacgata ctccattgga    840
ctgctggaca tgaccaagga gaaggaattc tacgatgaat ggccaatcaa gcttggagaa    900
gtagagcctt ataaaggtcc aaagacacct gatggcaggg aagtcaactt ttataaaatc    960
attgattaca ttttacatgg aaaagaagag atcaaagtga ttccgacgcc tcctgcagac   1020
cactggacac tcattagtgg gttgccaaca tatgttgctg aaaatggatt tatctgtaac   1080
atgatgaatg cccctgcgga tgaatacttc acatttcaga aaggacctgt agacgaaact   1140
ggttgggtca ttaagaatgt tttgtccctg cctattgtca acaagaaaga agatattgtg   1200
ggagtggcta cattttacaa caggaaggat ggaaaacctt tcgatgagca tgatgaatac   1260
attaccgaga ctctcacaca atttcttgga tggtctcttt taaatactga cacctacgat   1320
aagatgaata agctagaaaa cagaaaggac attgctcagg aaatgctcat gaaccaaacc   1380
aaagccactc ctgaagaaat taagtccatt ttgaaatttc aagagaagtt aaatgttgat   1440
gtaattgacg actgtgaaga aaaacaactt gttgcaattt tgaaagagga cttgccagac   1500
ccacgctcag cagaactgta cgaattccgc ttcagtgact tccccttac agagcacgga   1560
ttgattaaat gtggaatacg actgtttttt gaaataaatg tggtggagaa attcaaagta   1620
cctgtagagg ttcttaccag atggatgtac actgtgagga aagggtaccg agctgtcact   1680
taccacaatt ggcggcatgg gttcaacgtg gggcagacca tgtttacttt gctgatgaca   1740
ggaagattaa agaagtacta cacagatctc gaagcctttg ccatgcttgc tgctgctttc   1800
tgccatgata ttgaccacag aggcaccaat aatttgtacc agatgaaatc cacgtctcca   1860
ttagcaagac ttcatggttc ttctattttg gagaggcacc acctggagta cagtaagact   1920
ctgttgcagg atgagagttt aaacatcttc cagaacctaa ataagcggca gtttgaaaca   1980
gttattcatt tgttcgaggt cgcaataata gcaactgacc tggctttata tttcaagaag   2040
aggaccatgt ttcaaaaaat tgttgatgcc tgtgaacaaa tgcaaacgga agaagaagcc   2100
atcaaatatg taactgttga tccaaccaag aaagagatta tcatggcaat gatgatgacg   2160
gcatgtgact tgtctgctat taccaagccc tgggaggtgc aaagtcaggt agcacttatg   2220
gttgcaaatg aattttggga acaaggagat ctggagagaa cagtgttgca gcaacaaccc   2280
attcctatga tggacagaaa caaaagagat gaattaccta aacttcaagt tggatttatt   2340
gattttgttt gtacttttgt atataaggag ttctcacggt ttcacaaaga aatcacacct   2400
atgctgagtg gtcttcagaa taacagagta gaatggaaat cactagctga tgagtatgat   2460
gcaaagatga aggtcattga agaggaggca aaaaagcaag aaggaggagc cgaaaaagct   2520
gctgaagatt caggaggtgg tgatgacaaa aagtccaaaa catgtttaat gttgtaa      2577
```

<210> SEQ ID NO 10

<211> LENGTH: 252
<212> TYPE: DNA
<213> ORGANISM: Artificial Sequence
<220> FEATURE:
<223> OTHER INFORMATION: PDE6H cDNA, NM_006205.2

<400> SEQUENCE: 10
atgagtgaca acactactct gcctgctcca gcttcaaacc agggtcctac caccccacgc 60
aaaggccctc ccaagttcaa gcagaggcag actcgccaat tcaagagtaa acctccaaag 120
aaaggtgtga aaggatttgg agatgacatt ccaggaatgg aggggctagg aacagatatc 180
acagtgattt gtccatggga ggcattcagc cacctggaat tgcatgagct cgctcagttt 240
gggattatct ga 252

<210> SEQ ID NO 11
<211> LENGTH: 1065
<212> TYPE: DNA
<213> ORGANISM: Artificial Sequence
<220> FEATURE:
<223> OTHER INFORMATION: GNAT2 cDNA, NM_005272.3

<400> SEQUENCE: 11
atgggaagtg gagccagtgc tgaggacaaa gaactggcca agaggtccaa ggagctagaa 60
aagaagctgc aggaggatgc tgataaggaa gccaagactg tcaagctgct actgctgggt 120
gctggggagt caggaaagag caccatcgtc aaacagatga agatcattca ccaggatggc 180
tattcaccag aagaatgcct ggagttcaag gctatcatct atggaaatgt gctgcagtcc 240
atcctggcta tcatccgggc catgaccaca ctgggcatcg attatgctga accaagctgt 300
gcggatgacg ggcgacagct caacaacctg gctgactcca ttgaggaggg aaccatgcct 360
cctgagctcg tggaggtcat taggaggttg tggaaggatg gtggggtgca agcctgcttc 420
gagagagctg cagaatacca gcttaatgac tccgcatctt actacctgaa ccaattagaa 480
cgaattacag accctgagta cctccctagt gagcaagatg tgctccgatc cagagtcaaa 540
accacgggca tcattgaaac caagttttcc gtcaaagact tgaatttcag gatgtttgat 600
gtgggagggc agagatccga gagaaagaag tggatccact gcttcgaggg agtcacctgc 660
atcattttct gtgcagccct cagtgcctat gatatggtgc tggtggaaga tgacgaagtg 720
aatcgtatgc atgagtcttt gcatctgttc aacagcatat gtaaccacaa attctttgcg 780
gctacttcca ttgtcctctt tctcaacaag aaggacctct ttgaggaaaa aatcaagaaa 840
gtccatctca gcatttgttt tccagagtat gatggtaaca actcctatga tgatgcgggg 900
aattacataa agagccagtt ccttgacctc aatatgcgaa aagatgtcaa agaaatctac 960
agtcacatga cctgtgctac agatacacag aatgtcaaat ttgtgtttga tgcagttaca 1020
gatattatca tcaaagaaaa cctcaaggac tgcggcctct tctaa 1065

<210> SEQ ID NO 12
<211> LENGTH: 1638
<212> TYPE: DNA
<213> ORGANISM: Artificial Sequence
<220> FEATURE:
<223> OTHER INFORMATION: KCNV2 cDNA, NM_133497.3

<400> SEQUENCE: 12
atgctcaaac agagtgagag gagacggtcc tggagctaca ggccctggaa cacgacggag 60
aatgagggca gccaacaccg caggagcatt tgctccctgg gtgcccgttc cggctcccag 120
gccagcatcc acggctggac agagggcaac tataactact acatcgagga agacgaagac 180

```
ggcgaggagg aggaccagtg gaaggacgac ctggcagaag aggaccagca ggcaggggag    240
gtcaccaccg ccaagcccga gggccccagc gaccctccgg ccctgctgtc cacgctgaat    300
gtgaacgtgg gtggccacag ctaccagctg gactactgcg agctggccgg cttccccaag    360
acgcgcctag gtcgcctggc cacctccacc agccgcagcc gccagctaag cctgtgcgac    420
gactacgagg agcagacaga cgaatacttc ttcgaccgcg acccggccgt cttccagctg    480
gtctacaatt tctacctgtc cggggtgctg ctggtgctcg acgggctgtg tccgcgccgc    540
ttcctggagg agctgggcta ctggggcgtg cggctcaagt acacgccacg ctgctgccgc    600
atctgcttcg aggagcggcg cgacgagctg agcgaacggc tcaagatcca gcacgagctg    660
cgcgcgcagg cgcaggtcga ggaggcggag gaactcttcc gcgacatgcg cttctacggc    720
ccgcagcggc gccgcctctg gaacctcatg gagaagccat tctcctcggt ggccgccaag    780
gccatcgggg tggcctccag caccttcgtg ctcgtctccg tggtggcgct ggcgctcaac    840
accgtggagg agatgcagca gcactcgggg cagggcgagg gcggcccaga cctgcggccc    900
atcctggagc acgtggagat gctgtgcatg ggcttcttca cgctcgagta cctgctgcgc    960
ctagcctcca cgcccgacct gaggcgcttc gcgcgcagcg ccctcaacct ggtggacctg   1020
gtggccatcc tgccgctcta ccttcagctg ctgctcgagt gcttcacggg cgagggccac   1080
caacgcggcc agacggtggg cagcgtgggt aaggtgggtc aggtgttgcg cgtcatgcgc   1140
ctcatgcgca tcttccgcat cctcaagctg gcgcgccact ccaccggact gcgtgccttc   1200
ggcttcacgc tgcgccagtg ctaccagcag gtgggctgcc tgctgctctt catcgccatg   1260
ggcatcttca ctttctctgc ggctgtctac tctgtggagc acgatgtgcc cagcaccaac   1320
ttcactacca tcccccactc ctggtggtgg gccgcggtga gcatctccac cgtgggctac   1380
ggagacatgt acccagagac ccacctgggc aggtttttg ccttcctctg cattgctttt   1440
gggatcattc tcaacgggat gcccatttcc atcctctaca acaagttttc tgattactac   1500
agcaagctga aggcttatga gtataccacc atacgcaggg agaggggaga ggtgaacttc   1560
atgcagagag ccagaaagaa gatagctgag tgtttgcttg gaagcaaccc acagctcacc   1620
ccaagacaag agaattag                                                1638
```

<210> SEQ ID NO 13
<211> LENGTH: 3414
<212> TYPE: DNA
<213> ORGANISM: Artificial Sequence
<220> FEATURE:
<223> OTHER INFORMATION: CACNA2D4 cDNA, NM_172364.4

<400> SEQUENCE: 13

```
atggtctgtg gctgctctgc cctccttccc ctccccaacc ccaggcccac catgcctgca     60
actcccaact tcctcgcaaa ccccagctcc agcagccgct ggattcccct ccagccaatg    120
cccgtggcct gggcctttgt gcagaagacc tcggccctcc tgtggctgct gcttctaggc    180
acctccctgt cccctgcgtg gggacaggcc aagattcctc tggaaacagt gaagctatgg    240
gctgacacct tcggcgggga cctgtataac actgtgacca aatactcagg ctctctcttg    300
ctgcagaaga agtacaagga tgtggagtcc agtctgaaga tcgaggaggt ggatggcttg    360
gagctggtga ggaagttctc agaggacatg gagaacatgc tgcggaggaa agtcgaggcg    420
gtccagaatc tggtggaagc tgccgaggag gccgacctga accacgaatt caatgaatcc    480
ctggtgttcg actattacaa ctcggtcctg atcaacgaga gggacgagaa gggcaacttc    540
```

```
gtggagctgg gcgccgagtt cctcctggag tccaatgctc acttcagcaa cctgccggtg    600
aacacctcca tcagcagcgt gcagctgccc accaacgtgt acaacaaaga cccagatatt    660
ttaaatggag tctacatgtc tgaagccttg aatgctgtct tcgtggagaa cttccagaga    720
gacccaacgt tgacctggca atattttggc agtgcaactg gattcttcag gatctatcca    780
ggtataaaat ggacacctga tgagaatgga gtcattactt ttgactgccg aaaccgcggc    840
tggtacattc aagctgctac ttctcccaag gacatagtga ttttggtgga cgtgagcggc    900
agtatgaagg ggctgaggat gactattgcc aagcacacca tcaccaccat cttggacacc    960
ctgggggaga atgacttcat taatatcata gcgtacaatg actacgtcca ttacatcgag   1020
ccttgtttta aagggatcct cgtccaggcg gaccgagaca atcgagagca tttcaaactg   1080
ctggtggagg agttgatggt caaaggtgtg ggggtcgtgg accaagccct gagagaagcc   1140
ttccagatcc tgaagcagtt ccaagaggcc aagcaaggaa gcctctgcaa ccaggccatc   1200
atgctcatca gcgacggcgc cgtggaggac tacgagccgg tgtttgagaa gtataactgg   1260
ccagactgta aggtccgagt tttcacttac ctcattggga gagaagtgtc ttttgctgac   1320
cgcatgaagt ggattgcatg caacaacaaa ggctactaca cgcagatctc aacgctggcg   1380
gacacccagg agaacgtgat ggaatacctg cacgtgctca gccgccccat ggtcatcaac   1440
cacgaccacg acatcatctg gacagaggcc tacatggaca gcaagctcct cagctcgcag   1500
gctcagagcc tgacactgct caccactgtg gccatgccag tcttcagcaa gaagaacgaa   1560
acgcgatccc atggcattct cctgggtgtg gtgggctcag atgtggccct gagagagctg   1620
atgaagctgg cgccccggta caagcttgga gtgcacggat acgcctttct gaacaccaac   1680
aatggctaca tcctctccca tcccgacctc cggcccctgt acagagaggg gaagaaacta   1740
aaacccaaac ctaactacaa cagtgtggat ctctccgaag tggagtggga agaccaggct   1800
gaatctctga gaacagccat gatcaatagg gaaacaggta ctctctcgat ggatgtgaag   1860
gttccgatgg ataaagggaa gcgagttctt ttcctgacca atgactactt cttcacggac   1920
atcagcgaca cccctttcag tttgggggtg gtgctgtccc ggggccacgg agaatacatc   1980
cttctgggga acacgtctgt ggaagaaggc ctgcatgact tgcttcaccc agacctggcc   2040
ctggccggtg actggatcta ctgcatcaca gatattgacc cagaccaccg gaagctcagc   2100
cagctagagg ccatgatccg cttcctcacc aggaaggacc cagacctgga gtgtgacgag   2160
gagctggtcc gggaggtgct gtttgacgcg gtggtgacag cccccatgga agcctactgg   2220
acagcgctgg ccctcaacat gtccgaggag tctgaacacg tggtggacat ggccttcctg   2280
ggcacccggg ctggcctcct gagaagcagc ttgttcgtgg gctccgagaa ggtctccgac   2340
aggaagttcc tgacacctga ggacgaggcc agcgtgttca ccctggaccg cttcccgctg   2400
tggtaccgcc aggcctcaga gcatcctgct ggcagcttcg tcttcaacct ccgctgggca   2460
gaaggaccag aaagtgcggg tgaacccatg gtggtgacgg caagcacagc tgtggcggtg   2520
accgtggaca agaggacagc cattgctgca gccgcgggcg tccaaatgaa gctggaattc   2580
ctccagcgca aattctgggc ggcaacgcgg cagtgcagca ctgtggatgg gccgtgcaca   2640
cagagctgcg aggacagtga tctggactgc ttcgtcatcg acaacaacgg gttcattctg   2700
atctccaaga ggtcccgaga gacgggaaga tttctggggg aggtggatgg tgctgtcctg   2760
acccagctgc tcagcatggg ggtgttcagc caagtgacta tgtatgacta tcaggccatg   2820
tgcaaaccct cgagtcacca ccacagtgca gcccagcccc tggtcagccc aatttctgcc   2880
ttcttgacgg cgaccaggtg gctgctgcag gagctggtgc tgttcctgct ggagtggagt   2940
```

```
gtctggggct cctggtacga cagaggggcc gaggccaaaa gtgtcttcca tcactcccac   3000

aaacacaaga agcaggaccc gctgcagccc tgcgacacgg agtaccccgt gttcgtgtac   3060

cagccggcca tccgggaggc caacgggatc gtggagtgcg ggccctgcca gaaggtattt   3120

gtggtgcagc agattcccaa cagtaacctc ctcctcctgg tgacagaccc cacctgtgac   3180

tgcagcatct tcccaccagt gctgcaggag gcgacagaag tcaaatataa tgcctctgtc   3240

aaatgtgacc ggatgcgctc ccagaagctc cgccggcgac cagactcctg ccacgccttc   3300

catccagagg agaatgccca ggactgcggc ggcgcctcgg acacctcagc ctcgccgccc   3360

ctactcctgc tgcctgtgtg tgcctggggg ctactgcccc aactcctgcg gtga         3414
```

<210> SEQ ID NO 14
<211> LENGTH: 2430
<212> TYPE: DNA
<213> ORGANISM: Artificial Sequence
<220> FEATURE:
<223> OTHER INFORMATION: CNGB3 cDNA, NM_019098.4

<400> SEQUENCE: 14

```
atgtttaaat cgctgacaaa agtcaacaag gtgaagccta taggagagaa caatgagaat     60

gaacaaagtt ctcgtcggaa tgaagaaggc tctcacccaa gtaatcagtc tcagcaaacc    120

acagcacagg aagaaaacaa aggtgaagag aaatctctca aaaccaagtc aactccagtc    180

acgtctgaag agccacacac caacatacaa gacaaactct ccaagaaaaa ttcctctgga    240

gatctgacca caaaccctga ccctcaaaat gcagcagaac caactggaac agtgccagag    300

cagaaggaaa tggaccccgg gaaagaaggt ccaaacagcc cacaaaacaa accgcctgca    360

gctcctgtta taaatgagta tgccgatgcc cagctacaca acctggtgaa aagaatgcgt    420

caaagaacag ccctctacaa gaaaaagttg gtagagggag atctctcctc acccgaagcc    480

agcccacaaa ctgcaaagcc cacggctgta ccaccagtaa aagaaagcga tgataagcca    540

acagaacatt actacaggct gttgtggttc aaagtcaaaa agatgccttt aacagagtac    600

ttaaagcgaa ttaaacttcc aaacagcata gattcataca cagatcgact ctatctcctg    660

tggctcttgc ttgtcactct tgcctataac tggaactgct ggtttatacc actgcgcctc    720

gtcttcccat atcaaaccgc agacaacata cactactggc ttattgcgga catcatatgt    780

gatatcatct acctttatga tatgctattt atccagccca gactccagtt tgtaagagga    840

ggagacataa tagtggattc aaatgagcta aggaaacact acaggacttc tccaaaattt    900

cagttggatg tcgcatcaat aataccattt gatatttgct acctcttctt tgggtttaat    960

ccaatgttta gagcaaatag gatgttaaag tacacttcat tttttgaatt taatcatcac   1020

ctagagtcta taatggacaa agcatatatc tacagagtta ttcgaacaac tggatacttg   1080

ctgtttattc tgcacattaa tgcctgtgtt tattactggg cttcaaacta tgaaggaatt   1140

ggcactacta gatgggtgta tgatggggaa ggaaacgagt atctgagatg ttattattgg   1200

gcagttcgaa ctttaattac cattggtggc ctaccagaac cacaaacttt atttgaaatt   1260

gtttttcaac tcttgaattt tttttctgga gtttttgtgt tctccagttt aattggtcag   1320

atgagagatg tgattggagc agctacagcc aatcagaact acttccgcgc ctgcatggat   1380

gacaccattg cctacatgaa caattactcc attcctaaac ttgtgcaaaa gcgagttcgg   1440

acttggtatg aatatacatg ggactctcaa agaatgctag atgagtctga tttgcttaag   1500

accctaccaa ctacggtcca gttagccctc gccattgatg tgaacttcag catcatcagc   1560
```

-continued

```
aaagtcgact tgttcaaggg ttgtgataca cagatgattt atgacatgtt gctaagattg   1620

aaatccgttc tctatttgcc tggtgacttt gtctgcaaaa agggagaaat tggcaaggaa   1680

atgtatatca tcaagcatgg agaagtccaa gttcttggag gccctgatgg tactaaagtt   1740

ctggttactc tgaaagctgg gtcggtgttt ggagaaatca gccttctagc agcaggagga   1800

ggaaaccgtc gaactgccaa tgtggtggcc cacgggtttg ccaatctttt aactctagac   1860

aaaaagaccc tccaagaaat tctagtgcat tatccagatt ctgaaaggat cctcatgaag   1920

aaagccagag tgcttttaaa gcagaaggct aagaccgcag aagcaacccc tccaagaaaa   1980

gatcttgccc tcctcttccc accgaaagaa gagacaccca aactgtttaa aactctccta   2040

ggaggcacag gaaaagcaag tcttgcaaga ctactcaaat tgaagcgaga gcaagcagct   2100

cagaagaaag aaaattctga aggaggagag gaagaaggaa aagaaaatga agataaacaa   2160

aaagaaaatg aagataaaca aaaagaaaat gaagataaag gaaaagaaaa tgaagataaa   2220

gataaaggaa gagagccaga agagaagcca ctggacagac ctgaatgtac agcaagtcct   2280

attgcagtgg aggaagaacc ccactcagtt agaaggacag ttttacccag agggacttct   2340

cgtcaatcac tcattatcag catggctcct tctgctgagg gcggagaaga ggttcttact   2400

attgaagtca aagaaaaggc taagcaataa                                    2430
```

<210> SEQ ID NO 15
<211> LENGTH: 1786
<212> TYPE: DNA
<213> ORGANISM: Artificial Sequence
<220> FEATURE:
<223> OTHER INFORMATION: hG1.7 construct , 1.2 kb M/L opsin LCR fragment, 500 bp M opsin fragment, with M8 mutation

<400> SEQUENCE: 15

```
taggaataga agggtgggtg caggaggctg aggggtgggg aaagggcatg ggtgtttcat     60

gaggacagag cttccgtttc atgcaatgaa aagagtttgg agacggatgg tggtgactgg    120

actatacact tacacacggt agcgatggta cactttgtat tatgtatatt ttaccacgat    180

ctttttaaag tgtcaaaggc aaatggccaa atggttcctt gtcctatagc tgtagcagcc    240

atcggctgtt agtgacaaag cccctgagtc aagatgacag cagcccccat aactcctaat    300

cggctctccc gcgtggagtc atttaggagt agtcgcatta gagacaagtc caacatctaa    360

tcttccaccc tggccagggc cccagctggc agcgagggtg ggagactccg ggcagagcag    420

agggcgctga cattggggcc cggcctggct tgggtccctc tggcctttcc ccaggggccc    480

tctttccttg gggctttctt gggccgccac tgctcccgct cctctccccc catcccaccc    540

cctcaccccc tcgttcttca tatccttctc tagtgctccc tccactttca tccacccttc    600

tgcaagagtg tgggaccaca aatgagtttt cacctggcct ggggacacac gtgcccccac    660

aggtgctgag tgactttcta ggacagtaat ctgctttagg ctaaaatggg acttgatctt    720

ctgttagccc taatcatcaa ttagcagagc cggtgaaggt gcagaaccta ccgcctttcc    780

aggcctcctc ccacctctgc cacctccact ctccttcctg ggatgtgggg gctggcacac    840

gtgtggccca gggcattggt gggattgcac tgagctgggt cattagcgta atcctggaca    900

agggcagaca gggcgagcgg agggccagct ccggggctca ggcaaggctg gggcttcccc    960

ccagacaccc cactcctcct ctgctggacc cccacttcat agggcacttc gtgttctcaa   1020

agggcttcca aatagcatgg tggccttgga tgcccaggga agcctcagag ttgcttatct   1080

ccctctagac agaaggggaa tctcggtcaa gagggagagg tcgccctgtt caaggccacc   1140
```

-continued

```
cagccagctc atggcggtaa tgggacaagg ctggccagcc atcccaccct cagaagggac   1200

ccggtggggc aggtgatctc agaggaggct cacttctggg tctcacattc ttggatcaca   1260

ggtatttgcc actaagccca gctaattgtt ttttatttag tagaaacggg gtttcaccat   1320

gttagtcagg ctggtcggga actcctgacc tcaggagatc tacccgcctt ggcctcccaa   1380

agtgctggga ttacaggcgt gtgccactgt gcccagccac tttttttag acagagtctt   1440

ggtctgttgc ccaggctaga gttcagtggc gccatctcag ctcactgcaa cctccgcctc   1500

ccagattcaa gcgattctcc tgcctcgacc tcccagtagc tgggattaca ggtttccagc   1560

aaatccctct gagccgcccc cgggggctcg cctcaggagc aaggaagcaa ggggtgggag   1620

gaggaggtct aagtcccagg cccaattaag agatcagatg gtgtaggatt tgggagcttt   1680

taaggtgaag aggcccgggc tgatcccact ggccggtata aagcaccgtg accctcaggt   1740

gacgcaccat ctagagctgc cgtcggggac agggctttcc atagcc                  1786
```

<210> SEQ ID NO 16
<211> LENGTH: 6
<212> TYPE: DNA
<213> ORGANISM: Artificial Sequence
<220> FEATURE:
<223> OTHER INFORMATION: M8 mutation

<400> SEQUENCE: 16

```
tctaga                                                                 6
```

<210> SEQ ID NO 17
<211> LENGTH: 1970
<212> TYPE: DNA
<213> ORGANISM: Artificial Sequence
<220> FEATURE:
<223> OTHER INFORMATION: 2.0 kb M opsin promoter fragment with M8 mutation

<400> SEQUENCE: 17

```
taaaaagcaa gtcttgccag ggcagtggtg tgcacctgtg gtcccagcta ctcaggatgc     60

tgaggcagga ggattacttg tgcccagcaa gtagaggctg cagtgacctg tgactgtgct    120

actgccctcc aacctgggtg acagagtgag accttgtctc aaaaaaaaaa gagcgggggg    180

ggggggccgg gccgggcgtg gtggctcaca gctgtaatcc cagcactttg ggaagccaag    240

gcgggtggat cacttgaggt caggagtttg agaccatcat ggtcaacact gcgaaacact    300

gtccctacta aaaatacaaa aattagccgg gcatggtggc acacacctgt aatcccagct    360

actggggagg ctgaggcagg agaattgctt gagccgggga gacggaggtt gcagtgagcc    420

gagactgcgc cactgcactc cagcctgact gacaagagtg agattgtctc aaaaaaaaaa    480

aaaaagtaat cactagaaaa gaagctacat atgtacataa catccaaata accaagagga    540

gaaaaaaatg ggacttgatt aatcaaaaca aaaacaaaaa agaaagaaag aaagggggag    600

aaaataaaac aagggctggg tgtgctggct catgcctgta atcccagcac tttggaagcc    660

aaggtgggtg gatctcttga gctcaggagg tcaagaccag cctgggcaac atggcgaaac    720

cccgtctcta ttaaaaaaaa aattaataca acaattatcc tggagtggtg gtgcacacct    780

gtagtcccag ctacccagga cgctgagacg ggaggatcgc ttgatcccgg ggatgtcgag    840

gctgccgtga tcgcaccact gccctccagc cagggtggca gactgagacc ccatctcaaa    900

aaataaataa ataaaagcaa acaagaaaaa aaaaggcttg aaacatatct gatagataaa    960

gggctaatca acacaatata taaagaactg caaatcagta aactaagagc aaataaccca   1020
```

-continued

```
atataaagac attaaagggt agccacggac atctcagacg acgaaaaaca aaagacagta   1080

aacgtataat aaaacatgta attgcaaggt gatccgggaa tagtaagcga aaagcaacaa   1140

ttaaatacta ttttctcatc caccagaacg ccaaaaatta aaaagcctaa caatgtccag   1200

ggctggcgag aatgtggcag aaggtgatgt cacataccct gcaagtggga atctaaacag   1260

attcagggtt ttggtttttt tttaatcgca attaggtggc ctgttaaatt tttttcttg    1320

agacagagtt ttgctcttgt tgcccaggct ggagtgcaat ggctcgatct tggctcaccg   1380

caacctcgac ctcccaggta caagcgattc tcctgtctca gcctcccaag tagctgggag   1440

tacaggtatt tgccactaag cccagctaat tgttttttat ttagtagaaa cggggtttca   1500

ccatgttagt caggctggtc gggaactcct gacctcagga gatctacccg ccttggcctc   1560

ccaaagtgct gggattacag gcgtgtgcca ctgtgcccag ccactttttt ttagacagag   1620

tcttggtctg ttgcccaggc tagagttcag tggcgccatc tcagctcact gcaacctccg   1680

cctcccagat tcaagcgatt ctcctgcctc gacctcccag tagctgggat tacaggtttc   1740

cagcaaatcc ctctgagccg cccccggggg ctcgcctcag gagcaaggaa gcaaggggtg   1800

ggaggaggag gtctaagtcc caggcccaat taagagatca gatggtgtag gatttgggag   1860

cttttaaggt gaagaggccc gggctgatcc cactggccgg tataaagcac cgtgaccctc   1920

aggtgacgca ccatctagag ctgccgtcgg ggacagggct ttccatagcc              1970
```

COMPOSITIONS AND METHODS FOR TREATING RETINAL DISORDERS

FIELD OF THE INVENTION

The present invention relates to a therapy for the treatment and/or prevention of retinal disorders, in particular cone dystrophies, cone-rod dystrophies and Achromatopsia.

BACKGROUND OF THE INVENTION

In many mammalian species including mice and humans, the number of rod photoreceptors that mediate vision under dim light outnumbers greatly that of cone photoreceptors. However, in an industrialized world where illumination allows cones to operate throughout the day and night, rod-mediated vision is less important. Many patients with absent rod function from birth are identified only incidentally and, in fact, cannot recognize their abnormal vision. In contrast, when cone dysfunction is present, patients are always symptomatic and often suffer visual handicap that is dependent on the degree of their cone dysfunction.

In some conditions, only, or mostly, the cones are lost or dysfunctional, and rods remain relatively preserved. Such conditions can be known as cone dystrophies or cone-rod dystrophies (CRDs). Cone or cone-rod dystrophies are inherited retinal dystrophies characterised by the primary loss of cones, or sometimes by the concomitant loss of both rods and cones. Symptoms include vision loss, sensitivity to bright lights and poor colour vision. For example, Achromatopsia is a severe, hereditary retinal dystrophy with a complete absence of cone function from birth but, presumably, with a normal rod function. Mutations in multiple genes including CNGA3, CNGB3 and PDE6C have been associated with the disease. Each of the disease causing genes encodes an essential component of the cone phototransduction cascade that translates light into an electric signal by causing hyperpolarization of the photoreceptor cell. The deficiency in, for example, the CNGA3 or CNGB3 protein in the cone photoreceptor cells leads to an inability of the cells to hyperpolarise in response to light. As a result, the cells initially survive, but do not function, and the patient suffers from poor visual acuity, lack of colour vision and photophobia from birth. Various groups have developed therapy protocols in CNGA3-deficient mice that improve cone survival and function, as well as vision.

Other examples of causative genes involved in the pathogenesis of cone dystrophies include KCNV2, PDE6H, GNAT2 and CACNA2D4. The KCNV2 gene encodes the potassium voltage-gated channel modifier subfamily V member 2 protein. Mutations in KCNV2 are associated with cone dystrophy with supernormal rod electroretinogram (ERG), or retinal cone dystrophy type 3B, an autosomal recessive disorder that causes lifelong visual loss combined with a supernormal ERG response to a bright flash of light. The PDE6H gene encodes the inhibitory (gamma) subunit of the cone-specific cGMP phosphodiesterase. Mutations in this gene are associated with retinal cone dystrophy type 3A (RCD3A). The GNAT2 gene encodes the cone-specific alpha subunit of transducin. Mutations in the gene can result in infantile onset cone dystrophy. The CACNA2D4 gene encodes the calcium channel, voltage-dependent, alpha-2/delta subunit 4. Mutations in the gene can cause non-progressive cone dysfunction (retinal cone dystrophy 4, RCD4).

In age-related macular degeneration (AMD), visual impairment is caused primarily by degeneration of the cone-rich fovea in the central macula. Thus patients lose central vision and acuity, but often have relatively well preserved peripheral macula and thus have some useful residual vision that is limited by the paucity of cones outside the fovea.

There is a need to develop therapies that can improve cone survival and function, in order to treat or prevent retinal disorders such as cone-rod dystrophies.

SUMMARY OF THE INVENTION

The invention provides nucleic acids, transcriptional control units (TCUs), optimized gene sequences, expression constructs, and vectors for expressing genes in cone photoreceptors.

The TCUs disclosed herein comprise an M-opsin promoter or a fragment thereof under control of the M/L-opsin Locus Control Region (LCR) and are useful for driving high levels of expression in all three human cone types.

Also provided are expression constructs, comprising a human CNGA3 gene under control of a TCU optimized for expressing genes in cone photoreceptors, wherein the TCU comprises an M-opsin promoter or fragment thereof under control of the M/L-opsin Locus Control Region.

In some embodiments, the TCUs and expression constructs contain a mutation of 6 bp immediately downstream of the transcription start site in the M-opsin promoter or fragment thereof (mutation "M8"), wherein the mutation may increase the treatment effect of vectors and expression constructs containing this mutation over time.

Further provided is a codon-optimized sequence of the CNGA3 gene, which is provided as SEQ ID NO:8.

Also provided are vectors, such as viral vectors, comprising the expression constructs disclosed herein. The expression construct is preferably delivered using a vector derived from adenovirus serotype 8 (AAV8) or an alternative strong AAV serotype.

The invention also provides methods of using the nucleic acids, transcriptional control units (TCUs), optimized gene sequences, expression constructs, and vectors for the treatment and/or prevention of retinal disorders or dystrophies, including but not limited to cone dystrophies such as Achromatopsia.

Accordingly, in one aspect the invention provides:

a transcriptional control unit (TCU) of up to 2500 nucleotides in length comprising in a 5' to 3' direction:

(a) a Locus Control Region (LCR) comprising (i) SEQ ID NO 1; or (ii) a sequence having at least 90% sequence identity to said sequence (a)(i); and (b) a promoter element comprising (i) at least 200 nucleotides of either SEQ ID NO: 2 or SEQ ID NO: 17; or (ii) a sequence having at least 90% sequence identity to said sequence (b)(i);

said TCU exhibiting cone photoreceptor-specific promoter activity.

According to the above aspect, promoter element (b) may optionally comprise at least the last 200 or the last 500 nucleotides of either SEQ ID NO: 2 or SEQ ID NO: 17, or a sequence having at least 90% sequence identity to the last 200 or the last 500 nucleotides of either SEQ ID NO: 2 or SEQ ID NO: 17.

According to any one of the above aspects, promoter element (b) may comprise at least 200 nucleotides of SEQ ID NO: 3, optionally wherein promoter element (b) also comprises a sequence of at least 10 contiguous nucleotides selected from nucleotides 1 to 35 of SEQ ID NO:3, or a sequence comprising at least 10 contiguous nucleotides selected from a sequence having at least 90% sequence identity to nucleotides 1 to 35 of SEQ ID NO:3.

According to any one of the above aspects, promoter element (b) may comprise SEQ ID NO: 3 [529 bp promoter element in hG1.7] or SEQ ID NO:5 [247 bp promoter element in hG1.4] or a sequence having at least 90% sequence identity to SEQ ID NO:3 or SEQ ID NO: 5.

In any one of the above aspects, the promoter element may further comprise SEQ ID NO:16 [the M8 mutation]. For example, according to any one of the above aspects, nucleotides corresponding to nucleotides 1934 to 1939 (GGGCCG) of SEQ ID NO:2 may be replaced by SEQ ID NO:16.

According to one aspect, the TCU comprises SEQ ID NO: 4 [variant of the hG1.7 promoter construct, four nucleotides missing], SEQ ID NO: 6 [hG1.4 construct] or SEQ ID NO:15 [hG1.7 promoter construct in product].

The invention also provides an expression construct comprising a TCU described herein, wherein the TCU is operably linked to a sequence to be expressed in a cone photoreceptor-specific manner. In one embodiment, the sequence operably linked to the TCU comprises a gene encoding CNGA3, CNGB3, PDE6C, PDE6H, GNAT2, KCNV2 or CACNA2D4. In some embodiments, the operably linked sequence comprises SEQ ID NO: 7, 8, 9, 10, 11, 12, 13 or 14, or that has at least 80% sequence identity to SEQ ID NO: 7, 8, 9, 10, 11, 12, 13 or 14 and has the ability to rescue cone photoreceptor function. In one embodiment, the operably linked sequence comprises SEQ ID NO: 8 [CNGA3 codon optimized sequence], or that has at least 80% sequence identity to SEQ ID NO: 8 and has the ability to rescue cone photoreceptor function.

The invention also provides vectors comprising any of the nucleic acids, TCUs, promoter fragments, codon optimized genes, and/or expression constructs described herein. In some embodiments, the vector is a viral vector.

In some embodiments, the vector is an AAV vector and/or comprises an AAV genome or a derivative thereof. In one embodiment, the derivative is a chimeric, shuffled or capsid modified derivative. In one embodiment, the AAV genome is from a naturally derived serotype or isolate or clade of AAV. In one embodiment, the AAV genome is from AAV serotype 2 (AAV2), AAV serotype 4 (AAV4), or AAV serotype 8 (AAV8), and/or the AAV capsid is derived from AAV8. In a preferred embodiment, the genome is derived from AAV2 and the capsid is derived from AAV8. In one embodiment, AAV vector carries a gene encoding CNGA3.

The invention further provides host cells containing a nucleic acid or vector disclosed herein, as well as host cells that produce a nucleic acid or viral vector as disclosed herein. In one embodiment, the host cell is a HEK293 or HEK293T cell.

Also provided are pharmaceutical compositions comprising a nucleic acid or vector described herein and a pharmaceutically acceptable carrier.

The invention further provides methods of using the nucleic acids, vectors, optimized gene sequences, and/or expression constructs described herein in a method of preventing or treating retinal disorders. In one embodiment, the nucleic acids, vectors, optimized gene sequences, and/or expression constructs described herein are used in the manufacture of a medicament for the treatment or prevention of retinal disorders. Also provided is a method of treating or preventing retinal disorders in a patient in need thereof, comprising administering a therapeutically effective amount of a vector disclosed herein. In one embodiment, the retinal disorder is Achromatopsia. In some embodiments, the vector is administered to a patient by direct retinal, subretinal, or intravitreal injection.

BRIEF DESCRIPTION OF THE SEQUENCES

Figure 1:
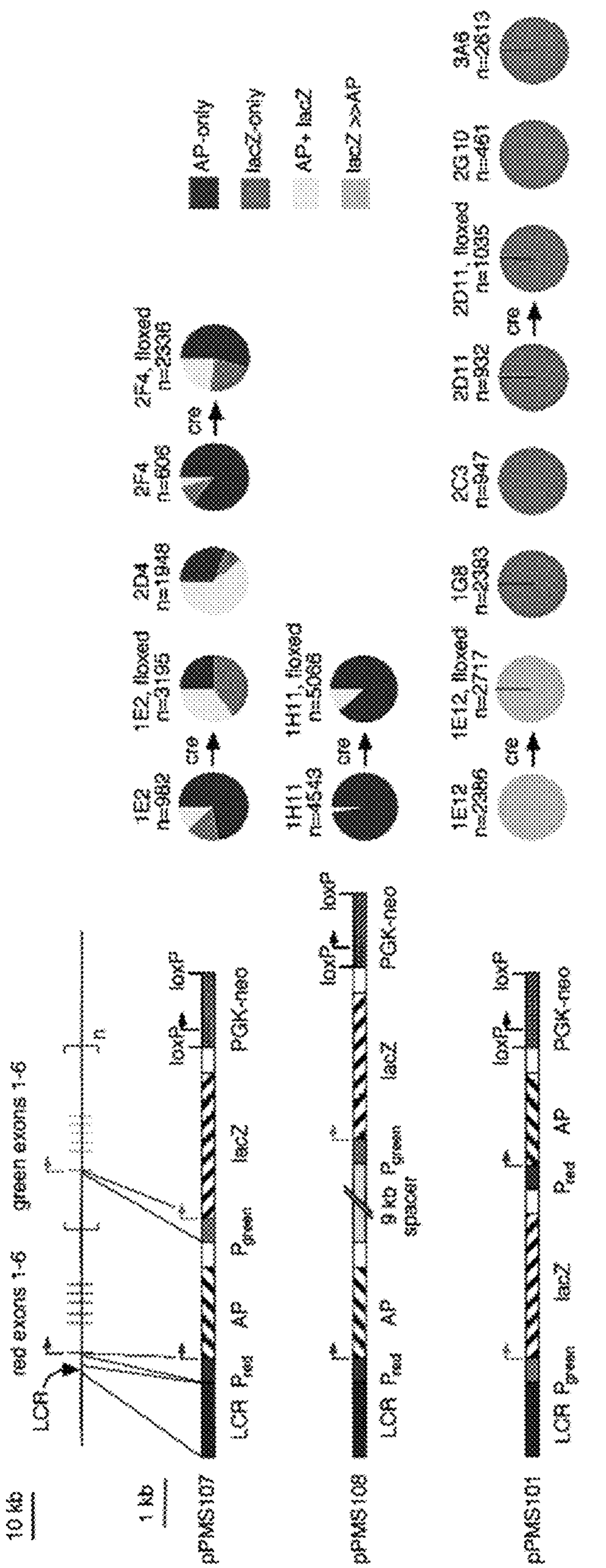
FIG. 1 shows the results of an in vivo reporter gene expression study in transgenic mice in order to assess the position effect of the Locus Control Region (LCR) on the green (M) opsin core promoter. Top left: The normal human red and green pigment gene array showing the locations of the LCR, transcription units, and exons. Lower left: Modified visual pigment gene arrays shown at a 10-fold enlarged scale. The start sites and direction of transcription are shown by arrows. $P_{red}$=human red pigment gene promoter. $P_{green}$=human green pigment gene promoter. AP, human placental alkaline phosphatase. lacZ, *E. coli* β-galactosidase. Right: Pie charts showing the fraction of transgene-expressing cells that express only AP, only lacZ, both AP and lacZ, or lacZ>>AP in chimeric or germ-line-transmitted mice for the constructs shown on the left. Cell counts from different mice derived from the same ES cell line were pooled to produce a single pie chart. Cell counts for those mouse lines from which the PGK-neo marker was excised by crossing to germ-line cre mice are shown immediately to the right of the pie chart for the corresponding parental line.

SEQ ID NO: 1 shows the DNA sequence of a 1.2 kb fragment of the human M/L opsin Locus Control Region.

SEQ ID NO:2 shows the DNA sequence of a 2.0 kb fragment of the human M opsin promoter.

SEQ ID NO:3 shows the DNA sequence of a 500 bp fragment of the human M opsin promoter.

SEQ ID NO:4 shows the DNA sequence of a variant of the hG1.7(M8) construct, which consists of a 1.2 kb fragment of the human M/L, opsin Locus Control Region followed by a 500 bp fragment of the human M opsin promoter, said opsin promoter fragment including the M8 mutation.

SEQ ID NO:5 shows the DNA sequence of a 200 bp fragment of the human M opsin promoter.

SEQ ID NO:6 shows the cDNA sequence of the hG1.4 (M8) construct, which consists of a 1.2 kb fragment of the human M/L opsin Locus Control Region followed by a 200 bp fragment of the human M opsin promoter, said opsin promoter fragment including the M8 mutation.

SEQ ID NO:7 shows the cDNA sequence of the human CNGA3 gene.

SEQ ID NO:8 shows the codon-optimised cDNA sequence of the human CNGA3 gene.

SEQ ID NO:9 shows the cDNA sequence of the human PDE6C gene.

SEQ ID NO:10 shows the cDNA sequence of the human PDE6H gene.

SEQ ID NO:11 shows the cDNA sequence of the human GNAT2 gene.

SEQ ID NO:12 shows the cDNA sequence of the human KCNV2 gene.

SEQ ID NO:13 shows the cDNA sequence of the human CACNA2D4 gene.

SEQ ID NO:14 shows the cDNA sequence of the human CNGB3 gene.

SEQ ID NO:15 shows the DNA sequence of the hG1.7 (M8) construct, which comprises a 1.2 kb fragment of the human M/L opsin Locus Control Region followed by the sequence GATC, and a 500 bp fragment of the human M opsin promoter, said opsin promoter fragment including the M8 mutation.

SEQ ID NO:16 shows the sequence of the M8 mutation.

SEQ ID NO:17 shows the DNA sequence of a 2.0 kb fragment of the human M opsin promoter containing the M8 mutation.

DETAILED DESCRIPTION OF THE INVENTION

It is to be understood that different applications of the disclosed polynucleotide sequences may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural references unless the content clearly dictates otherwise. Thus, for example, reference to "a polynucleotide" includes "polynucleotides", reference to "a promoter" includes "promoters", reference to "a vector" includes two or more such vectors, and the like. "M/L opsin" and "L/M opsin" are used interchangeably to refer to green and red opsin.

All publications, patents and patent applications cited herein, whether supra or infra, are hereby incorporated by reference in their entirety.

Transcriptional Control Units (TCUs)

In one aspect, the invention provides a TCU optimized for the expression of genes in cone photoreceptor cells. In one embodiment, the disclosure provides a TCU that comprises a fragment of the M/L opsin Locus Control Region (LCR). In a preferred embodiment, the TCU comprises a fragment of the human M/L opsin Locus Control Region (LCR).

In another embodiment, the disclosure provides a TCU that comprises a promoter region, such as a the M opsin promoter or a fragment thereof. In a preferred embodiment, the TCU disclosed herein comprises the human M opsin promoter or a fragment thereof.

In some embodiments, the TCU comprises fragments and/or variants of the human M/L opsin Locus Control Region (LCR) and the human M-opsin promoter or a fragment thereof, wherein the TCU has cone photoreceptor-specific promoter activity.

In one embodiment, the TCU comprises an LCR that comprises a sequence of nucleotides, typically contiguous nucleotides, from SEQ ID NO:1 that confers cone photoreceptor-specific expression of an operably linked polynucleotide sequence. Further contemplated is an LCR that comprises a sequence that has at least 75%, at least 80%, at least 85%, at least 90%, at least 95%, at least 98%, or at least 99% sequence identity to SEQ ID NO:1. In some embodiments, the LCR contains a deletion or an insertion of one or more nucleotides, wherein the deletion or insertion does not abolish cone photoreceptor-specific expression of a gene payload operatively linked to the modified LCR.

In one embodiment, the TCU comprises an M opsin promoter or a fragment thereof, wherein the M opsin promoter or fragment thereof comprises a sequence of nucleotides, typically contiguous nucleotides, from SEQ ID NO: 2 or SEQ ID NO:17 that confers cone photoreceptor-specific expression on an operably linked polynucleotide sequence. The M opsin promoter or fragment thereof may, for example, comprise up to 1200 nucleotides of SEQ ID NO:2 or SEQ ID NO:17, and preferably no more than 1100, no more than 1000, no more than 900, no more than 800, no more than 700, no more than 600, no more than 500, no more than 400, no more than 300, or no more than 200 nucleotides of SEQ ID NO:2 or SEQ ID NO:17. In some embodiments, the fragment of the M opsin promoter comprises at least 200, 300, 400 or 500 nucleotides of SEQ ID NO:2 or SEQ ID NO:17. Further contemplated is a fragment of the M opsin promoter having at least 75%, at least 80%, at least 85%, at least 90%, at least 95%, at least 98%, or at least 99% sequence identity to at least 200, at least 300, at least 400, or at least 500 contiguous nucleotides of SEQ ID NO: 2 or SEQ ID NO: 17. In some embodiments, the M-opsin promoter or fragment thereof contains a deletion or an insertion of one or more nucleotides, wherein the deletion or insertion does not abolish cone photoreceptor-specific expression of a gene payload operatively linked to the modified M-opsin promoter or fragment. In some embodiments, the M-opsin promoter or fragment thereof consists essentially of SEQ ID NO:2 or SEQ ID NO:17. In some embodiments, the M-opsin promoter or fragment thereof consists of SEQ ID NO: 2 or SEQ ID NO:17.

Preferably, the TCU comprises a fragment of the M opsin promoter that comprises SEQ ID NO:3 or a sequence that a substantially identical to SEQ ID NO:3. Further contemplated is a TCU comprising a fragment of the M opsin promoter that comprises at least 200, at least 300, at least 400, or at least 500 nucleotides of SEQ ID NO:3 or a sequence having at least 75%, at least 80%, at least 85%, at least 90%, at least 95%, at least 98%, or at least 99% sequence identity to the at least 200, at least 300, at least 400, or at least 500 nucleotides of SEQ ID NO: 3. In some embodiments, the fragment of the M opsin promoter consists essentially of SEQ ID NO:3. In some embodiments, the fragment of the M opsin promoter consists of SEQ ID NO:3.

In some embodiments, the TCU comprises at least 200 nucleotides of SEQ ID NO:3 or a sequence having at least 90% sequence identity to at least 200 nucleotides of SEQ ID NO:3 and a sequence comprising at least 10, at least 15, at least 20, at least 25, at least 30 or at least 35 contiguous nucleotides of nucleotides 1-35 of SEQ ID NO:3. In some embodiments, the TCU comprises at least 200 nucleotides of SEQ ID NO:3 or a sequence having at least 90% sequence identity to at least 200 nucleotides of SEQ ID NO:3 and a sequence having at least 90% sequence identity to at least 10, at least 15, at least 20, at least 25, at least 30 or at least 35 contiguous nucleotides corresponding to nucleotides 1-35 of SEQ ID NO:3.

Preferably, the TCU comprises a fragment of the M opsin promoter that comprises SEQ ID NO:5 or a sequence that is substantially identical to SEQ ID NO:5. In some embodiments, the fragment of the M opsin promoter consists essentially of SEQ ID NO:5. In some embodiments, the fragment of the M opsin promoter consists of SEQ ID NO:5.

Additional promoters and fragments thereof contemplated for use in the TCU are promoters or promoter fragments that differ in sequence from the sequences above but retain cone photoreceptor-specific promoter activity. Such sequences have at least 75%, at least 80%, at least 85%, at least 90%, at least 95%, at least 98%, or at least 99% sequence identity to a sequence of contiguous nucleotides from SEQ ID NO:2 or SEQ ID NO:17 as defined above. Percentage sequence identity of variants is preferably measured over the full length of the corresponding portion of SEQ ID NO:2 or SEQ ID NO:17, or over a 500, 600, 700, 800, 900, 1000, 1100 or 1200 nucleotide section of SEQ ID NO:2 or SEQ ID NO:17 aligned with the variant sequence. Further contemplated are promoters and fragments thereof that comprises a sequence has at least 75%, at least 80%, at least 85%, at least 90%, at least 95%, at least 98%, or at least 99% sequence identity to SEQ ID NO:3 and/or to SEQ ID NO:5.

Sequence identity may be calculated using any suitable algorithm. For example, the PILEUP and BLAST algorithms can be used to calculate identity or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10. Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Alternatively, the UWGCG Package provides the BESTFIT program which can be used to calculate identity (for example used on its default settings) (Devereux et al (1984) Nucleic Acids Research 12, 387-395).

In some embodiments, the TCU comprises an M-opsin promoter or fragment thereof that contains an M8 mutation sequence TCTAGA (SEQ ID NO:16). In one embodiment, the TCU comprises an M-opsin promoter or fragment thereof that contains, one, two, there, four, five, or six nucleotides of SEQ ID NO:16. For example, nucleotides corresponding to nucleotides 1934 to 1939 (GGGCCG) of SEQ ID NO:2 may be replaced by SEQ ID NO:16.

In some embodiments, the TCU includes additional nucleotide sequences not naturally found in the M/L, opsin LCR and/or M-opsin promoter regions. The additional nucleotide sequence can be 5' or 3' of either the LCR or the M-opsin promoter region. In some embodiments, the additional sequence is located between the LCR and the M-opsin promoter region. In one embodiments, the sequence "GATC" is located between the LCR region and the M-opsin region.

In one embodiment, the TCU comprises SEQ ID NO:4. In one embodiment, the TCU comprises SEQ ID NO:6. In one embodiment, the TCU comprises SEQ ID NO:15.

Further contemplated is a TCU comprising a sequence having at least 75%, at least 80%, at least 85%, at least 90%, at least 95%, at least 98%, or at least 99% sequence identity to SEQ ID NO:4, SEQ ID NO:6 or SEQ ID NO:15.

In one embodiment, the TCU consists essentially of SEQ ID NO:4. In one embodiment, the TCU consists essentially of SEQ ID NO:6. In one embodiment, the TCU consists essentially of SEQ ID NO:15.

In one embodiment, the TCU consists of SEQ ID NO:4. In one embodiment, the TCU consists of SEQ ID NO:6. In one embodiment, the TCU consists of SEQ ID NO:15.

The TCU may further be positioned anywhere within a larger sequence as long as cone photoreceptor-specific promoter activity is retained. In embodiments, the TCUs described herein are located 5', or immediately 5', to the gene to be expressed (e.g., the payload) in a cone photoreceptor-specific manner as described herein.

The TCU can also be used in tandem with other regulatory elements such as one or more further promoters, enhancers and/or LCRs.

The TCU may be provided in form of an isolated nucleic acid molecule.

The TCU provided by this disclosure can be used to drive expression of genes (payload) in the cone photoreceptor in a cone photoreceptor-specific manner. Cone photoreceptor-specific expression may be defined as expression that is only present in the cone photoreceptor, but not significantly in other cell types. Cone photoreceptor-specific expression may be defined as expression that is more than about 10 times greater, 20 times greater, 50 times greater, or 100 or more times greater in the cone photoreceptor than in other cell types, especially rod photoreceptor cells. Expression in the cone photoreceptors and other cells types can be measured by any suitable standard technique known to the person skilled in the art. For example, RNA expression levels can be measured by quantitative real-time PCR. Protein expression can be measured by western blotting or immunohistochemistry. TCUs provided herein provide expression of an operably linked gene in all cone photoreceptor subtypes.

The TCU provided by this disclosure can be used to drive significantly increased expression of genes in the cone photoreceptor as compared to a reference TCU or promoter. Significantly increased expression can be defined as more than about 10 times, 20 times, 50 times, 100 times, 200 times or 300 times the expression of the gene in the cone photoreceptor when compared with expression driven by a reference TCU or promoter, including but not limited to the original M-opsin promoter. Expression in the cone photoreceptors and other cells types can be measured by any suitable standard technique known to the person skilled in the art. For example, RNA expression levels can be measured by quantitative real-time PCR. Protein expression can be measured by western blotting or immunohistochemistry.

The TCU provided by this disclosure can be used to drive expression of a protein encoding nucleotide sequence in the cone photoreceptor, including nucleotide sequences expressing proteins that are not normally expressed in the cone photoreceptor such as GFP.

For instance, the TCUs provided in this disclosure are useful for expressing genes in cone photoreceptors necessary for the normal function of cone photoreceptors, including, but not limited to, guanine nucleotide-binding protein G(t) subunit alpha-2 (GNAT2), cyclic nucleotide-gated cation channel alpha-3 (CNGA3), cyclic nucleotide-gated cation channel beta-3 (CNGB3), cone cGMP-specific 3',5'-cyclic phosphodiesterase subunit alpha' (PDE6C), retinal cone rhodopsin-sensitive cGMP 3',5'-cyclic phosphodiesterase subunit gamma (PDE6H), potassium voltage-gated channel subfamily V member 2 (KCNV2), and voltage-dependent calcium channel subunit alpha-2/delta-4 (CACNA2D4), which are essential proteins for the normal function of cones. As such, the present invention provides TCUs and methods for expressing, for example, GNAT2, CNGA3, CNGB3, PDE6C, PDE6H, KCNV2, and CACNA2D4 genes in cone photoreceptors. The PDE6C, GNAT2, CNGA3 and CNGB3 genes are four of the genes contributing to Achromatopsia. PDE6C is the alpha subunit of the cone cGMP-specific 3',5'-cyclic phosphodiesterase. GNAT2 is the alpha component of cone transducin, an essential element of the cone phototransduction cascade. CNGA3 is the alpha subunit of the cone cyclic nucleotide-gated ion channel, which closes in response to light, thereby hyperpolarising the cone cell. CNGB3 is the beta subunit of the cone cyclic nucleotide-gated ion channel, which closes in response to light, thereby hyperpolarising the cone cell.

Expression Constructs

The invention also provides expression constructs comprising a TCU disclosed herein, operably linked to a sequence, such as a gene sequence, to be expressed in a cone photoreceptor-specific manner.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the expression construct. An expression construct may be defined as a polynucleotide sequence capable of driving protein expression from a polynucleotide sequence containing a coding sequence.

Thus, the expression construct may for example comprise an PDE6H, PDE6C, GNAT2, KCNV2, CACNA2D4, CNGA3 or CNGB3 coding sequence, for example a polynucleotide selected from SEQ ID NOs: 7 to 14, or a variant of SEQ ID NOs: 7 to 14 that retains the functionality of the protein translated from the sequence selected from SEQ ID NOs: 7 to 14.

A variant of a polynucleotide selected from the group consisting of SEQ ID NOs: 7 to 14 may be defined as any variant of the sequence of SEQ ID NOs: 7 to 14, including naturally occurring variants in the nucleic acid sequence. The variant may be defined as having at least about 60%, 70%, 80%, 90%, 95%, 96%, 97%, 98% or 99% sequence identity to any one of SEQ ID NOs 7 to 14, wherein the polypeptide translated from the variant sequence retains its functionality. The variant may be defined as having at least about 60%, 70%, 80%, 90%, 95%, 96%, 97%, 98% or 99% sequence identity to any one of SEQ ID NOs 7 to 14, wherein the polypeptide translated from the variant sequence has the ability to rescue cone photoreceptor function. In embodiments, the variant is a codon optimized version of the coding sequence.

The expression constructs contemplated by the disclosure may recue cone photoreceptor function. Rescuing cone photoreceptor function can be defined as restoring at least about 50%, 60%, 70%, 80% 90%, 95%, 96%, 97%, 98%, 99% or 100% of cone photoreceptor function. Cone photoreceptor function can be analysed by any suitable standard technique known to the person skilled in the art, for example, by electroretinography analysis of retinal responses.

Rescuing cone photoreceptor function can also be defined as prolonging cone survival. Prolonging cone survival can be defined as extending the time that a cone photoreceptor is functional by about 10%, 20%, 30%, 40%, 50%, 60%, 70%, 80%, 90%, 95%, 96%, 97%, 98%, 99%, 100% or more than 100% when compared with a cone photoreceptor affected by a cone dystrophy. Cone photoreceptor function can be analysed by any suitable standard technique known to the person skilled in the art, for example, by electroretinography analysis of retinal responses. Examples of prolonging cone survival also include improving ERG activity or slowing loss of ERG activity, improving retinal sensitivity or slowing/halting progressive loss of retinal sensitivity, slowing or halting loss of photoreceptor cells, improving vision or slowing/halting vision loss.

The expression construct of the invention may comprise a TCU operably linked to a CNGA3 gene. In some embodiments, the CNGA3 gene sequence comprises SEQ ID NO:7. In some embodiments, the CNGA3 gene comprises a codon-optimized sequence. "Codon-optimization" relates to the process of altering a naturally occurring polynucleotide sequence to enhance expression in the target organism, for example, humans. In one embodiment of the present invention, the human CNGA3 gene, SEQ ID NO:7, has been optimised to create SEQ ID NO:8. In the optimised CNGA3 cDNA of SEQ ID NO:8 rare codons have been replaced with those that occur more frequently and/or those which are frequently found in highly expressed human genes.

In one embodiment, the expression construct comprises a TCU operably linked to SEQ ID NO:8.

Vectors

The invention provides vectors comprising the nucleic acids, TCUs, promoters and fragments thereof, optimized genes, and expression constructs disclosed herein. The vector may be of any type, for example, it may be a plasmid vector or a minicircle DNA.

The efficacy of therapy is, in general, dependent upon adequate and efficient delivery of the donated DNA. This process is usually mediated by viral vectors. As such, the invention provides viral vectors, which may be based, for example, on the herpes simplex virus, adenovirus, or lentivirus. The viral vector may be an adeno-associated virus (AAV) vector or a derivative thereof. AAV is a particularly attractive vector as it is generally non-pathogenic; the majority people have been infected with this virus during their life with no adverse effects. The immune privilege of ocular tissue, a result of anatomical barriers and immunomodulatory factors, renders the eye largely exempt from adverse immunological responses.

In one embodiment, the viral vector comprises an AAV genome from a naturally derived serotype, isolate or clade of AAV, or a derivative thereof.

An "AAV genome" is a polynucleotide sequence which encodes functions needed for production of an AAV viral particle. These functions include those operating in the replication and packaging cycle for AAV in a host cell, including encapsidation of the AAV genome into an AAV viral particle. Naturally occurring AAV viruses are replication-deficient and rely on the provision of helper functions in trans for completion of a replication and packaging cycle. Accordingly and with the additional removal of the AAV rep and cap genes, the AAV genome of the vector of the invention is replication-deficient.

The AAV genome may be in single-stranded form, either positive or negative-sense, or alternatively in double-stranded form. The use of a double-stranded form allows bypass of the DNA replication step in the target cell and so can accelerate transgene expression.

The AAV genome may be from any naturally derived serotype or isolate or clade of AAV. As is known to the skilled person, AAV viruses occurring in nature may be classified according to various biological systems.

Commonly, AAV viruses are referred to in terms of their serotype. A "serotype" corresponds to a variant subspecies of AAV which owing to its profile of expression of capsid surface antigens has a distinctive reactivity which can be used to distinguish it from other variant subspecies. Typically, a virus having a particular AAV serotype does not efficiently cross-react with neutralising antibodies specific for any other AAV serotype. AAV serotypes include AAV1, AAV2, AAV3, AAV4, AAV5, AAV6, AAV7, AAV8, AAV9, AAV10 and AAV11, also recombinant serotypes, such as Rec2 and Rec3, recently identified from primate brain. In vectors of the invention, the genome may be derived from any AAV serotype. The capsid may also be derived from any AAV serotype. The genome and the capsid may be derived from the same serotype or different serotypes.

In one embodiment, the genome of the vector disclosed herein is derived from AAV serotype 2 (AAV2), AAV serotype 4 (AAV4), AAV serotype (AAV5) or AAV serotype 8 (AAV8). Other AAV vectors which may be used include vectors derived from AAV44.9 and AAV-Anc80. It is most preferred that the genome is derived from AAV2, which binds to the target cells via the heparin sulphate proteoglycan receptor, but other serotypes of particular interest for use in the invention include AAV4, AAV5 and AAV8, which efficiently transduce tissue in the eye, such as the retinal pigmented epithelium.

The sequences of AAV genomes or of elements of AAV genomes including ITR sequences, rep or cap genes for use in the invention may be derived from the following accession numbers for AAV whole genome sequences: Adeno-associated virus 1 NC_002077, AF063497; Adeno-associated virus 2 NC_001401; Adeno-associated virus 3 NC_001729; Adeno-associated virus 3B NC_001863; Adeno-associated virus 4 NC_001829; Adeno-associated virus 5 Y18065, AF085716; Adeno-associated virus 6 NC_001862; Avian AAV ATCC VR-865 AY186198, AY629583, N_004828; Avian AAV strain DA-1 NC_006263, AY629583; Bovine AAV NC_005889, AY388617.

AAV viruses may also be referred to in terms of clades or clones. This refers to the phylogenetic relationship of naturally derived AAV viruses, and typically to a phylogenetic group of AAV viruses which can be traced back to a common ancestor, and includes all descendants thereof. Additionally, AAV viruses may be referred to in terms of a specific isolate, i.e. a genetic isolate of a specific AAV virus found in nature. The term genetic isolate describes a population of AAV viruses which has undergone limited genetic mixing with other naturally occurring AAV viruses, thereby defining a recognisably distinct population at a genetic level.

Examples of clades and isolates of AAV that may be used in the invention include: Clade A: AAV1 NC_002077, AF063497, AAV6 NC_001862, Hu. 48 AY530611, Hu 43 AY530606, Hu 44 AY530607, Hu 46 AY530609, Clade B: Hu. 19 AY530584, Hu. 20 AY530586, Hu 23 AY530589, Hu22 AY530588, Hu24 AY530590, Hu21 AY530587, Hu27 AY530592, Hu28 AY530593, Hu 29 AY530594, Hu63 AY530624, Hu64 AY530625, Hu13 AY530578, Hu56 AY530618, Hu57 AY530619, Hu49 AY530612, Hu58 AY530620, Hu34 AY530598, Hu35 AY530599, AAV2 NC_001401, Hu45 AY530608, Hu47 AY530610, Hu51 AY530613, Hu52 AY530614, Hu T41 AY695378, Hu S17 AY695376, Hu T88 AY695375, Hu T71 AY695374, Hu T70 AY695373, Hu T40 AY695372, Hu T32 AY695371, Hu T17 AY695370, Hu LG15 AY695377, Clade C: Hu9 AY530629, Hu10 AY530576, Hu11 AY530577, Hu53 AY530615, Hu55 AY530617, Hu54 AY530616, Hu7 AY530628, Hul8 AY530583, Hul5 AY530580, Hu16 AY530581, Hu25 AY530591, Hu60 AY530622, Ch5 AY243021, Hu3 AY530595, Hu1 AY530575, Hu4 AY530602 Hu2, AY530585, Hu61 AY530623, Clade D: Rh62 AY530573, Rh48 AY530561, Rh54 AY530567, Rh55 AY530568, Cy2 AY243020, AAV7 AF513851, Rh35 AY243000, Rh37 AY242998, Rh36 AY242999, Cy6 AY243016, Cy4 AY243018, Cy3 AY243019, Cy5 AY243017, Rh13 AY243013, Clade E: Rh38 AY530558, Hu66 AY530626, Hu42 AY530605, Hu67 AY530627, Hu40 AY530603, Hu41 AY530604, Hu37 AY530600, Rh40 AY530559, Rh2 AY243007, Bb1 AY243023, Bb2 AY243022, Rh10 AY243015, Hu17 AY530582, Hu6 AY530621, Rh25 AY530557, Pi2 AY530554, Pi1 AY530553, Pi3 AY530555, Rh57 AY530569, Rh50 AY530563, Rh49 AY530562, Hu39 AY530601, Rh58 AY530570, Rh61 AY530572, Rh52 AY530565, Rh53 AY530566, Rh51 AY530564, Rh64 AY530574, Rh43 AY530560, AAV8 AF513852, Rh8 AY242997, Rh1 AY530556, Clade F: Hu14 (AAV9) AY530579, Hu31 AY530596, Hu32 AY530597, Clonal Isolate AAVS Y18065, AF085716, AAV 3 NC_001729, AAV 3B NC_001863, AAV4 NC_001829, Rh34 AY243001, Rh33 AY243002, Rh32 AY243003.

The skilled person can select an appropriate serotype, clade, clone or isolate of AAV for use in the present invention on the basis of their common general knowledge.

It should be understood however that the invention also encompasses use of an AAV genome of other serotypes that may not yet have been identified or characterised. The AAV serotype determines the tissue specificity of infection (or tropism) of an AAV virus. Accordingly, preferred AAV serotypes for use in AAV viruses administered to patients in accordance with the invention are those which have natural tropism for or a high efficiency of infection of target cone photoreceptor cells.

Wild-type AAV, containing viral genes, insert their genomic material into chromosome 19 of the host cell. The AAV single-stranded DNA genome comprises two inverted terminal repeats (ITRs) and two open reading frames, containing structural (cap) and packaging (rep) genes.

Typically, the AAV genome of a naturally derived serotype or isolate or clade of AAV comprises at least one inverted terminal repeat sequence (ITR). Vectors of the invention typically comprise two ITRs, preferably one at each end of the genome. An ITR sequence acts in cis to provide a functional origin of replication, and allows for integration and excision of the vector from the genome of a cell. Preferred ITR sequences are those of AAV2 and variants thereof. The AAV genome typically comprises packaging genes, such as rep and/or cap genes which encode packaging functions for an AAV viral particle. The rep gene encodes one or more of the proteins Rep78, Rep68, Rep52 and Rep40 or variants thereof. The cap gene encodes one or more capsid proteins such as VP1, VP2 and VP3 or variants thereof. These proteins make up the capsid of an AAV viral particle. Capsid variants are discussed below.

For therapeutic purposes, the ITRs may be provided in cis in addition to the therapeutic gene. The AAV virus may therefore be modified: the viral genes may be removed from the genome, producing recombinant AAV (rAAV). The rAAV contains the therapeutic gene and at least one ITR. The removal of the viral genes renders rAAV incapable of actively inserting its genome into the host cell DNA. Instead, the rAAV genomes fuse via the ITRs, forming circular, episomal structures, or insert into pre-existing chromosomal breaks. For viral production, the structural and packaging genes, now removed from the rAAV, are supplied in trans, in the form of a helper plasmid.

Preferably the AAV genome will be derivatised for the purpose of administration to patients. Such derivatisation is standard in the art and the present invention encompasses the use of any known derivative of an AAV genome, and derivatives which could be generated by applying techniques known in the art.

Derivatives of an AAV genome include any truncated or modified forms of an AAV genome which allow for expression of a Rep-1 transgene from a vector of the invention in vivo. Typically, it is possible to truncate the AAV genome significantly to include minimal viral sequence yet retain the above function. This is preferred for safety reasons to reduce the risk of recombination of the vector with wild-type virus, and also to avoid triggering a cellular immune response by the presence of viral gene proteins in the target cell.

Typically, a derivative will include at least one inverted terminal repeat sequence (ITR), preferably more than one ITR, such as two ITRs or more. One or more of the ITRs may be derived from AAV genomes having different serotypes, or may be a chimeric or mutant ITR. A preferred mutant ITR is one having a deletion of a trs (terminal resolution site). This deletion allows for continued replication of the genome to generate a single-stranded genome which contains both coding and complementary sequences, i.e. a self-complementary AAV genome. This allows for bypass of DNA replication in the target cell, and so enables accelerated transgene expression.

The one or more ITRs will preferably flank the expression construct cassette containing the promoter and transgene of the invention. The inclusion of one or more ITRs is preferred to aid packaging of the vector of the invention into viral particles. In preferred embodiments, ITR elements will be the only sequences retained from the native AAV genome in the derivative. Thus, a derivative will preferably not include the rep and/or cap genes of the native genome and any other sequences of the native genome. This is preferred for the reasons described above, and also to reduce the possibility of integration of the vector into the host cell genome. Additionally, reducing the size of the AAV genome allows for increased flexibility in incorporating other sequence elements (such as regulatory elements) within the vector in addition to the transgene.

With reference to the AAV2 genome, the following portions could therefore be removed in a derivative of the invention: One inverted terminal repeat (ITR) sequence, the replication (rep) and capsid (cap) genes. However, in some embodiments, including in vitro embodiments, derivatives may additionally include one or more rep and/or cap genes or other viral sequences of an AAV genome.

A derivative may be a chimeric, shuffled or capsid-modified derivative of one or more naturally occurring AAV viruses. The invention encompasses the provision of capsid protein sequences from different serotypes, clades, clones, or isolates of AAV within the same vector. The invention encompasses the packaging of the genome of one serotype into the capsid of another serotype, i.e. pseudotyping.

Chimeric, shuffled or capsid-modified derivatives will be typically selected to provide one or more desired functionalities for the viral vector. Thus, these derivatives may display increased efficiency of gene delivery, decreased immunogenicity (humoral or cellular), an altered tropism range and/or improved targeting of a particular cell type compared to an AAV viral vector comprising a naturally occurring AAV genome, such as that of AAV2. Increased efficiency of gene delivery may be effected by improved receptor or co-receptor binding at the cell surface, improved internalisation, improved trafficking within the cell and into the nucleus, improved uncoating of the viral particle and improved conversion of a single-stranded genome to double-stranded form. Increased efficiency may also relate to an altered tropism range or targeting of a specific cell population, such that the vector dose is not diluted by administration to tissues where it is not needed.

Chimeric capsid proteins include those generated by recombination between two or more capsid coding sequences of naturally occurring AAV serotypes. This may be performed for example by a marker rescue approach in which non-infectious capsid sequences of one serotype are co-transfected with capsid sequences of a different serotype, and directed selection is used to select for capsid sequences having desired properties. The capsid sequences of the different serotypes can be altered by homologous recombination within the cell to produce novel chimeric capsid proteins.

Chimeric capsid proteins also include those generated by engineering of capsid protein sequences to transfer specific capsid protein domains, surface loops or specific amino acid residues between two or more capsid proteins, for example between two or more capsid proteins of different serotypes.

Shuffled or chimeric capsid proteins may also be generated by DNA shuffling or by error-prone PCR. Hybrid AAV capsid genes can be created by randomly fragmenting the sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence.

The unrelated protein or peptide may advantageously be one which acts as a ligand for a particular cell type, thereby conferring improved binding to a target cell or improving the specificity of targeting of the vector to a particular cell population.

The unrelated protein may also be one which assists purification of the viral particle as part of the production process i.e. an epitope or affinity tag. The site of insertion will typically be selected so as not to interfere with other functions of the viral particle e.g. internalisation, trafficking of the viral particle. The skilled person can identify suitable sites for insertion based on their common general knowledge.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

The vector of the invention takes the form of a viral vector comprising the promoters and expression constructs of the invention.

For the avoidance of doubt, the invention also provides an AAV viral particle comprising a vector of the invention. The AAV particles of the invention include transcapsidated forms wherein an AAV genome or derivative having an ITR of one serotype is packaged in the capsid of a different serotype. The AAV particles of the invention also include mosaic forms wherein a mixture of unmodified capsid proteins from two or more different serotypes makes up the viral envelope. The AAV particle also includes chemically modified forms bearing ligands adsorbed to the capsid surface. For example, such ligands may include antibodies for targeting a particular cell surface receptor.

The AAV2 genome, like those of all AAV serotypes, can be enclosed in a number of different capsid proteins. AAV2 can be packaged in its natural AAV2 capsid (AAV2/2) or it can be pseudotyped with other capsids (e.g. AAV2 genome in AAV1 capsid, resulting in AAV2/1, or AAV2 genome in AAV8 capsid, resulting in AAV2/8).

In a preferred embodiment, the AAV capsid is derived from AAV8. In a particularly preferred embodiment, where the operably linked sequence is a CNGA3 gene, it is preferred that the capsid is AAV8 or another capsid other than AAV5.

AAV transduces cells via serotype specific receptor-mediated endocytosis. A major factor influencing the kinetics of rAAV transgene expression is the rate of virus particle uncoating within the endosome. This, in turn, depends upon the type of capsid enclosing the genetic material. After uncoating, the linear single-stranded rAAV genome is stabilised by forming a double-stranded molecule via de novo synthesis of a complementary strand. The use of self-complementary DNA may bypass this stage by producing double-stranded transgene DNA. It has been found that self-complementary AAV2/8 gene expression is of faster onset and higher amplitude, compared to single-stranded AAV2/8. Thus, by circumventing the time lag associated with second-strand synthesis, gene expression levels are increased, when compared to transgene expression from standard single-stranded constructs. Subsequent studies investigating the effect of self-complementary DNA in other AAV pseudotypes have produced similar results. One caveat to this technique is that, as AAV has a packaging capacity of approximately 4.8 kb, the self-complementary recombinant genome must be appropriately sized (i.e. 2.3 kb or less).

In addition to modifying packaging capacity, pseudotyping the AAV2 genome with other AAV capsids can alter cell specificity and the kinetics of transgene expression. For example, when AAV2 is pseudotyped with the AAV4 capsid, transgene expression is targeted specifically to RPE cells. In addition, AAV2/8 is reported to transduce photoreceptors more efficiently than either AAV2/2 or AAV2/5.

Preparation of Vectors

The vector of the invention may be prepared by standard means known in the art for provision of vectors for therapy. Thus, well established public domain transfection, packaging and purification methods can be used to prepare a suitable vector preparation.

As discussed above, a vector of the invention may comprise the full genome of a naturally occurring AAV virus in addition to a promoter of the invention or a variant thereof. However, commonly a derivatised genome will be used, for instance a derivative which has at least one inverted terminal repeat sequence (ITR), but which may lack AAV genes such as rep or cap.

In such embodiments, in order to provide for assembly of the derivatised genome into an AAV viral particle, additional genetic constructs providing AAV and/or helper virus functions may be provided in a host cell in combination with the derivatised genome. These additional constructs will typically contain genes encoding structural AAV capsid proteins i.e. cap, VP1, VP2, VP3, and genes encoding other functions required for the AAV life cycle, such as rep. The selection of structural capsid proteins provided on the additional construct will determine the serotype of the packaged viral vector.

A particularly preferred packaged viral vector for use in the invention comprises a derivatised genome of AAV2 in combination with the AAV8 capsid protein.

As mentioned above, AAV viruses are replication incompetent and so helper virus functions, preferably adenovirus helper functions can also be provided on one or more additional constructs to allow for AAV replication. There are also systems known to the skilled person that use a single construct that comprises rep, cap and Ad helper functions, so additional helper constructs are not required.

All of the above additional constructs may be provided as plasmids or other episomal elements in the host cell, or alternatively one or more constructs may be integrated into the genome of the host cell.

The transcriptional control unit of the invention has the ability to rescue loss of cone photoreceptor function, which may occur for example by mutations in the CNGA3 gene. "Rescue" generally means any amelioration or slowing of progression of a retinal disorder or dystrophy phenotype, for example restoring presence of CNGA3 protein in the cone photoreceptor, improving ERG activity or slowing loss of ERG activity, improving retinal sensitivity or slowing/halting progressive loss of retinal sensitivity, slowing or halting loss of photoreceptor cells, improving vision or slowing/halting vision loss.

The properties of transcriptional control unit of the invention can also be tested using techniques based on those in the Examples. In particular, a transcriptional control unit of the invention can be assembled into a vector of the invention and delivered to the retina of a CNGA3-deficient test animal, such as a mouse, and the effects observed and compared to a control. Preferably, the control will be the other eye of the same animal, which is either untreated or treated with a control vector such as one containing a reporter gene as opposed to a sequence of the invention. Electroretinography analysis of retinal responses to light can then be used to confirm that photoreceptor cells in the eyes that are treated with are more sensitive to light than photoreceptors from eyes that are untreated or treated with a control vector. The sensitivity of the treated eye to light may for example be at least 1.1, 1.2, 1.5, 2, 5, 10, 20, 50, 100, 200, 500 or 1000-fold greater than that of the untreated or control-treated eye.

Methods of Therapy and Medical Uses

In one aspect, the invention provides nucleic acid molecules (such as TCUs, promoters and fragments thereof, codon-optimized genes, expression constructs, and vectors)

as well as methods for the treatment and/or prevention of retinal disorders or dystrophies in a patient in need thereof.

The retina is composed of the retinal pigment epithelium (RPE) cell layer and three layers of neurosensory cells; namely (from outer to inner), the outer nuclear layer (containing rod and cone photoreceptor cells), the inner nuclear layer (containing bipolar cells), and the ganglion cell layer. Retinal disorders or dystrophies can be defined as diseases of the retina, characterised by progressive loss of photoreceptor cells and concomitant loss of vision. The retinal disorders or dystrophies may be inherited retinal disorders or dystrophies.

In one embodiment, nucleic acid molecules and methods are provided for the treatment and/or prevention of cone-rod dystrophy and/or cone dystrophy. Cone-rod dystrophies can be defined as diseases characterised by progressive loss of cone photoreceptor cells and concomitant loss of vision and may be inherited. In one embodiment, the retinal disorder is Achromatopsia or macular degeneration. The macular degeneration may be age-related macular degeneration (AMID), for example wet or neovascular AMD or geographic atrophy, an inherited macular degeneration condition or an inherited cone dystrophy.

The terms "patient" and "subject" may be used interchangeably. The patient is preferably a mammal. The mammal may be a commercially farmed animal, such as a horse, a cow, a sheep or a pig, a laboratory animal, such as a mouse or a rat, or a pet, such as a cat, a dog, a rabbit or a guinea pig. The patient is more preferably human. The subject may be male or female. The subject is preferably identified as being at risk of, or having, a retinal disorder or dystrophy.

The terms "treat," "treated," "treating," or "treatment" as used herein refer to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects.

The patient may be asymptomatic and/or may have a predisposition to the disease. As such, the invention also provides a method or use that comprises a step of identifying whether or not a subject is at risk of developing, or has, retinal disorders, such as cone dystrophies, including, but not limited to, Achromatopsia. A prophylactically effective amount of a nucleic acid, such as a vector, as disclosed herein may be administered to such a subject. A prophylactically effective amount is an amount which prevents the onset of one or more symptoms of the disease. As such, in some embodiments, a nucleic acid, such as a vector, as disclosed herein may be administered in order to prevent or delay the onset of one or more symptoms of retinal disorders, such as cone-rod dystrophies, including, but not limited to, Achromatopsia. Alternatively, a nucleic acid, such as a vector, as disclosed herein may be administered once the symptoms of the disease have appeared in a subject i.e. to cure existing symptoms of the disease. A therapeutically effective amount of the nucleic acid, such as a vector, as disclosed herein may be administered to such a subject. As used herein, "therapeutically effective amount" means an amount of a nucleic acid set forth herein that, when administered to a mammal, is effective in producing the desired therapeutic effect. In one embodiment, the invention provides for methods of treating and/or preventing a retinal disorder or dystrophy, wherein a nucleic acid, such as a vector, as disclosed herein is administered to a patient in need of in a therapeutically effective amount. In some embodiments, the retinal disorder or dystrophy is a cone dystrophy, including, but not limited to, Achromatopsia.

The invention also provides the use of a nucleic acid, such as a vector, as disclosed herein in the manufacture of a medicament for the treatment or prevention of retinal disorders or dystrophies, such as cone dystrophies, including, but not limited to, Achromatopsia. The invention also provides a method of treating or preventing retinal disorders, such as cone dystrophies, in particular Achromatopsia in a patient in need thereof comprising administering a therapeutically effective amount of a nucleic acid, such as a vector, as disclosed herein to the patient.

Methods of Administration

In general, direct retinal, subretinal or intravitreal delivery of a nucleic acid, such as a vector, as disclosed herein, typically by injection, is preferred. Delivery to the retinal, subretinal space or intravitreal space is thus preferred.

The invention therefore also provides a method of treating or preventing cone dystrophies, in particular Achromatopsia in a patient in need thereof, comprising administering a therapeutically effective amount of a nucleic acid, such as a vector, as disclosed herein to the patient by direct retinal, subretinal or intravitreal injection.

In a related aspect, the invention provides for use of a nucleic acid, such as a vector, as disclosed herein in a method of treating or preventing retinal disorders, such as cone dystrophies, in particular Achromatopsia by administering said vector to a patient by direct retinal, subretinal or intravitreal injection.

Additionally, the invention provides the use of a nucleic acid, such as a vector, as disclosed herein in the manufacture of a medicament for treating or preventing retinal disorders, such as cone dystrophies, in particular Achromatopsia by direct retinal, subretinal or intravitreal injection.

The invention also provides a nucleic acid, such as a vector, as disclosed herein for use in the treatment of retinal disorders, such as cone dystrophies, in particular Achromatopsia, wherein said vector is administered directly into the retinal, subretinal space or intravitreal space.

The administration of the nucleic acid, such as a vector, as disclosed herein is typically by direct retinal or subretinal injection. This includes direct delivery to cone photoreceptor cells.

The delivery is made typically directly to, or subretinally to, the degenerating retina in a patient suffering from retinal disorders, such as cone-rod dystrophies, in particular Achromatopsia.

The nucleic acid, such as a vector, as disclosed herein may transduce the above target cells without entering any other cell populations. Intravitreal injection may also be used to deliver the vector of the invention.

The dose of the nucleic acid, such as a vector, as disclosed herein may be determined according to various parameters, especially according to the age, weight and condition of the patient to be treated; the route of administration; and the required regimen. Again, a physician will be able to determine the required route of administration and dosage for any particular patient.

A typical single dose is between $10^{10}$ and $10^{12}$ genome particles, depending on the amount of remaining retinal tissue that requires transduction. A genome particle is defined herein as an AAV capsid that contains a single stranded DNA molecule that can be quantified with a sequence specific method (such as real-time PCR). That dose may be provided as a single dose, but may be repeated for the fellow eye or in cases where the nucleic acid, such as a vector, as disclosed herein may not have targeted the correct region of retina for whatever reason (such as surgical complication). The treatment is preferably a single permanent treatment for each eye, but repeat injections, for example in future years and/or with different AAV serotypes may be considered.

Host Cells

The invention additionally provides a host cell comprising a nucleic acid, such as a vector or a viral vector, or AAV viral particle disclosed herein. Any suitable host cell can be used to produce the nucleic acids, as such vectors, disclosed herein. In general, such cells will be transfected mammalian cells, but other cell types, e.g. insect cells, can also be used. In terms of mammalian cell production systems, HEK293 and HEK293T are preferred for AAV vectors. BHK or CHO cells may also be used.

Pharmaceutical Compositions and Dosages

The invention further provides a pharmaceutical composition comprising a nucleic acid, such as a vector, disclosed herein, as well as a pharmaceutically acceptable carrier, diluent, excipient, adjuvant, buffer, stabiliser, and/or other materials well known to those skilled in the art. Such materials should be non-toxic and should not interfere with the efficacy of the active ingredient. Also provided is a pharmaceutical composition that comprises a pharmaceutically acceptable carrier, diluent, excipient, adjuvant, buffer, stabiliser, and/or other materials well known to those skilled in the art and a nucleic acid sequence, a plasmid, a vector, or a viral vector as described herein.

The precise nature of the carrier or other material may be determined by the skilled person according to the route of administration, i.e. here direct retinal, subretinal or intravitreal injection.

The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. In some cases, a surfactant, such as pluronic acid (PF68) 0.001% may be used.

For injection at the site of affliction, the active ingredient will be in the form of an aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection, Hartmann's solution. Preservatives, stabilisers, buffers, antioxidants and/or other additives may be included, as required.

For delayed release, the vector may be included in a pharmaceutical composition which is formulated for slow release, such as in microcapsules formed from biocompatible polymers or in liposomal carrier systems according to methods known in the art.

Dosages and dosage regimes can be determined within the normal skill of the medical practitioner responsible for administration of the composition. The dosage of active agent(s) may vary, depending on the reason for use, the individual subject, and the mode of administration. The dosage may be adjusted based on the subject's weight, the age and health of the subject, and tolerance for the compound(s) or composition.

Combination Therapies

The nucleic acids, TCUs, promoters, codon-optimized genes, expression constructs, vectors and/or pharmaceutical compositions disclosed herein can be used in combination with any other therapy for the treatment and/or prevention of retinal disorders, such as cone dystrophies, including, but not limited to, Achromatopsia.

Kits

The nucleic acids, TCUs, promoters, codon-optimized genes, expression constructs, vectors and/or pharmaceutical compositions disclosed herein can be packaged into a kit.

EXAMPLES

Materials and Methods

Plasid Construction

To create an improved version of the Green Cone Opsin promoter, the 1250-bp Locus Control Region (LCR) (Smallwood et al., 2002) was combined with various fragments of the green opsin core promoter (bp −480 to +40) into the parent plasmid pAAV/CMV.eGFP, creating pAAV/hG1.7.eGFP plasmid construct and pAAV/hG1.4.eGFP. Vector constructs carrying the 'M8' mutated promoters were produced by site-specific mutagenesis.

For the therapeutic gene constructs, pAAV/coCNGA3 was created by cloning the codon- and Kozak-optimised CNGA3 sequence from a pUC57 plasmid (produced by GenScript) into the pAAV plasmid carrying the various green (M) cone opsin promoter constructs.

Codon Optimization

Codon optimization was achieved through GenScript's proprietary OptimumGene™ codon optimization tool.

Virus Production Protocol AAV2/8 and AAV2/5

Recombinant AAV2 serotype 8 virus and AAV2 serotype 5 virus were produced using the triple transfection of 293Tcells method previously described (Gao et el. 2002). 145 $cm^2$ plates of 293T cell plates (20 plates per virus batch) were transfected with a mix comprising of Plasmid of interest:Viral Capsid plasmid:Helper plasmid DNA in the ratio of 1:1:3, polyethylenimine (PEI—Polysciences Inc., Eppelheim, Germany) and DMEM after a 10 minute incubation. The transfected cells were bedded for 24 hours. 48 hours after transfection, cells were harvested, concentrated by centrifugation, resuspended in TD buffer (140 mM NaCl, 5 mM KCl, 0.7 mM K2HPO4, 3.5 mM MgCl2, 25 mM Tris Base [pH=7.5]). This was then lysed by 3-4 freeze-thaw cycles, followed by Benzonase (Sigma Aldrich, Dorset, UK) treatment, and then cellular debris was removed by successive centrifugation and syringe filtration steps.

Purification was performed by ion exchange chromatography (using a method based on that by Davidoff et al. 2004). The eluate was concentrated in a Vivaspin 4 10 kDa concentrator tube (Sartorius Stedim Biotech, Fisher Scientific, Loughborouh, UK), washed in PBS-MK, then concentrated to a 100-150 μl volume, then aliquoted for −80° C. (long term) or +4° C. (short term) storage.

Production and Transduction of Human Stem Cell Derived Retinal Organoids

The human H9 embryonic stem cell (ESC) lines was maintained on feeder free conditions on E8 medium and geltrex coated 6 well plates. hESCs were dissociated using a dispase and collagenase solution. ESC clumps were collected and resuspended in E8 media. For retinal neuroepithelia differentiation human ESC were maintained until confluent when media without FGF was added to cultures for two days. Proneural induction media (Advanced DMEM/F12, MEM non-essential amino acids, N2 Supplement, 100 mM Glutamine and Pen/Strep) was added until optic vesicles were observed. Vesicles were manually excised and kept in 96 well plates in retinal differentiation media (DMEM, F12, Pen/Strep and B27 without retinoic acid) and at 6 weeks of differentiation medium was supplemented with FBS, taurine and glutamax and at 10 weeks RA was added.

AAV vectors (serotype SsH10) carrying the Green Cone Opsin promoter constructs driving eGFP were added to the medium at $1.2\times10^{11}$ vg/well (1-3 organoids/well). Organoids were cultured for a further 28 days before harvesting and analysis.

Immunohistochemistry

Eyes were prepared for fixation by corneal piercing, and then immersed in 1% paraformaldehyde (PFA, pH 7.4). Retinal organoids were fixed by immersion in 1% paraformaldehyde (PFA, pH 7.4). Eyes were left to fix at room temperature for up to an hour, before being removed from solution, and fully immersed in Optimal cutting temperature (OCT) embedding matrix, with the anterior-posterior of the eye suspended in the horizontal-vertical axis within embedding tubes. These were then frozen and stored at −20° C. until required for sectioning.

10-18 micron sections were prepared using Bright® OTF5000 Cryostat (Bright Instrument Co Ltd, Cambridgeshire, UK), thereby enabling the visualization of both the superior and inferior aspects of the retina. Slices were collected immediately after sectioning on polysine-coated microscope slides, and allowed to air dry at room temperature. Slides were either stored at −20° C. or analysed directly.

For immunohistochemistry, sections were blocked in 5% goat serum and 1% bovine serum albumin in PBS. Anti-cone opsin primary antibodies (Millipore) were incubated overnight at 4° C. Sections were incubated with secondary antibody for 2 hrs at RT and washed. Alexa-fluor secondary antibodies (Invitrogen-Molecular Probes) were used at a 1:500 dilution. Slides were stained with DAPI either as an addition to the mounting medium (0.1% DAPI in medium) or by immersion in 0.2% DAPI in TBS and PBS-washing prior to mounting in fluorescent mounting medium (DAKO). Mounted slides were stored at 4° C.

Mounted slides were imaged using Leica DM5500Q confocal microscope (Leica Biosystems, Germany) or a Zeiss AxioObserver Z1 (Carl Zeiss Inc, Gottingen, Germany).

Subretinal Injection

Subretinal injections were performed on Cpfl5 (CNGA3-deficient) (Hawes et al., 2006) and C57BL/6 mice around 2 weeks after birth. An operating microscope was utilised throughout ophthalmic surgery. A 1.5 cm, 34-gauge hypodermic needle (Hamilton, Switzerland) was inserted tangentially through the sclera, creating a self-sealing scleral tunnel wound (Tan et al. 2009). 1.0-1.5 μl of the viral suspension was injected within the superior and inferior hemispheres of the subretinal space, each creating an ophthalmoscopically-visible bullous retinal detachment. C57BL/6 were utilised for the promoter study, and injected with $1\times10^{12}$ viral titre. Cpfl5 mice were used in the CNGA3 rescue studies. Mice were injected with CNGA3 viral constructs in a designated eye, with the control viral constructs injected in the contralateral eye. All mice were injected bilaterally.

In Vivo Treatment Efficacy

Restoration of retinal function was assessed by photopic electroretinography. ERG recordings were obtained from both eyes simultaneously. Following dark adaptation overnight (~12 hours), one drop of 2.5% phenylephrine and 1% tropicamide (Minims, Bausch & Lomb) was applied onto each eye to dilate the pupil and the eyes were kept moist by applying a lubricant. ERGs were carried out using commercially available equipment (Espion ERG Diagnosys System). Photopic single-flash recordings were obtained at increasing light intensities of 0.1, 1, 3.16, 10, 31.6 and 75.28 $cd\cdot s/m^2$ on a background of 30 $cd/m^2$. Unless indicated Figures show average photopic b-wave amplitudes (mean±SD) at 4 weeks post-treatment, when vectors had reached peak expression.

Example 1: Optimisation a Cone-Specific Transcriptional Control Unit (TCU)

The human Locus Control Region (LCR), which is situated upstream of the red opsin gene, enhances expression of both the red opsin (L-opsin) and green opsin (M-opsin) genes, which are located in tandem (see FIG. 1, top left). Powerful cone-specific promoters have previously utilised the LCR and red opsin promoter, as they are physically adjacent elements. In an in vivo reporter gene expression study in transgenic mice by Smallwood et al, the different levels of expression from either the red or green opsin promoter based on their physical proximity to the LCR were examined. Smallwood et al. constructed several derivatives of the human red and green array to demonstrate different levels of expression from either the red or green opsin promoter based on their physical proximity to the LCR (see FIG. 1, lower left). Each derivative consisted of an alkaline phosphatase (AP) reporter gene under control of the red opsin promoter and a β-galactosidase (LacZ) under control of the green opsin promoter. For each embryonic stem cell line, retinas were analysed either from multiple chimeric founders or from multiple progeny that had stably inherited the transgene. In the latter case, the analysis was performed both before and after crossing to germ-line cre mice to remove the loxP-flanked PGK-neo cassette.

In the wild-type construct, which uses the natural chromosomal arrangement (pPMS107), 65-95% of cones express either AP (under control of the red opsin promoter) or lacZ (under control of the green opsin promoter), but not both. Inserting a 9-kb spacer between the two transcription units (i.e. increasing the distance between the LCR and the green opsin promoter, construct pPMS108) leads to a large shift from lacZ (green promoter)- to AP (red promoter)-expressing cells. Exchanging the locations of the two transcription units (pPMS101) and placing the green opsin core promoter immediately after the LCR (pPMS101), skewed the expression profile of these transgenic mice almost exclusively towards green opsin core promoter transcription (>99%).

Figure 2:
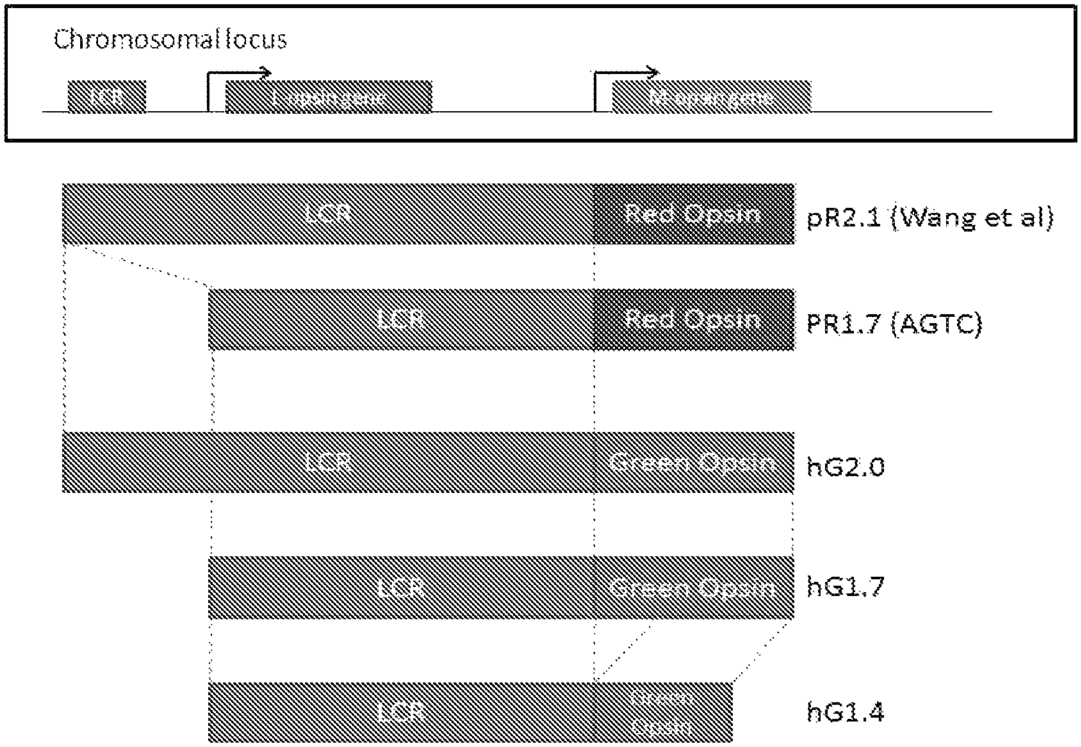
FIG. 2 shows a schematic diagram of the chromosomal arrangement of the red (L-) and green (M-) opsin promoters (boxed, top). Schematic diagrams of previously developed transcriptional units (pR2.1 and PR1.7), as well as the engineered transcriptional control units disclosed in this study. LCR=Locus Control Region.

This disclosure provides an alternative cone-specific transcriptional control unit (TCU) utilising the human LCR and an optimized human green opsin promoter. A conserved core element of the human green opsin promoter (0.2 kb) was identified and a series of TCUs using engineered green opsin promoters was generated using the LCR region and green opsin promoters of various sizes: 2.0 Kb (hG2.0), 1.7 Kb (hG1.7) and 1.4 Kb (hG1.4), see FIG. 2. A red opsin promoter fragment of 1.7 Kb (PR1.7, analogous to the promoter used by AGTC, Ye et al., 2016)) was also generated as a control.

Additionally, a series of AAVshh10 vectors containing GFP reporters driven by the promoters described above was generated and the expression in human ES-derived retinal cultures was assessed.

All constructs tested provided similar transduction profiles in terms of levels of GFP expression and cone cell-specificity. Constructs with smaller promoter fragments provide more space to package larger genes within the AAV vector.

Figure 3:
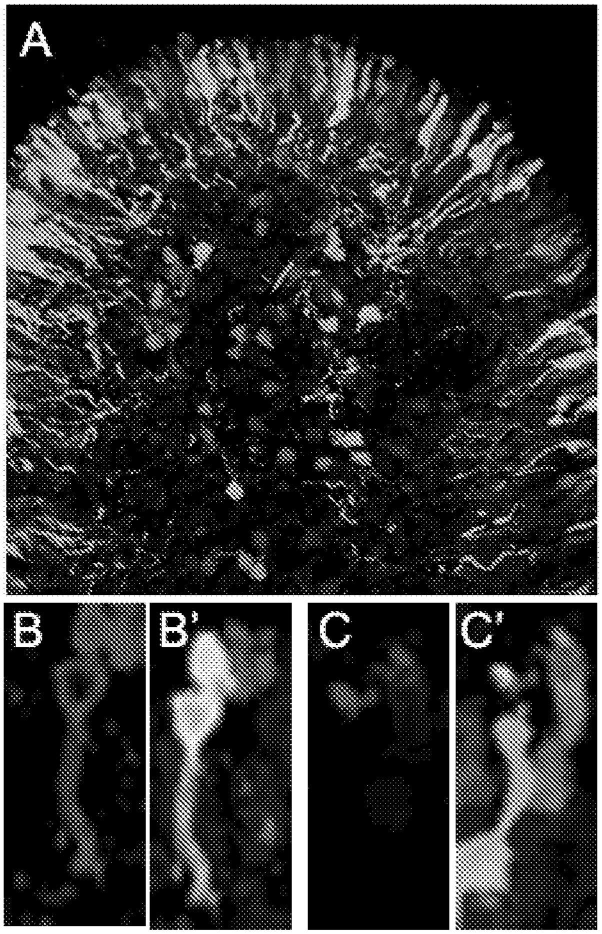
FIG. 3 illustrates the transduction pattern of cone cells transduced with an AAVssh10 vector expressing green fluorescent protein (GFP) under the control of the hG1.4 TCU. Shown are cryosections of human embryonic stem cell-derived retina transduced with AAVshh10-hG1.4(M8)-GFP. Transduction pattern of cone cells was visualised by GFP imaging (A). Co-localisation of blue opsin (S-opsin; B) with GFP (B') and red/green opsin (L/M-opsin; C) with GFP (C') is indicated following staining using antibodies that bind to either blue opsin (S-opsin) or red/green opsins (L/M opsin).

Example 2—An Optimized TCU Provides Robust Expression of a Reporter Gene in All Cone Subtypes To test the ability of the optimized TCUs disclosed herein to promote reporter protein expression in cone cells, human ES-derived retinas were transduced using AAVshh10-hG1.4.GFP, Robust reporter gene expression (FIG. 3A) in all cone subtypes (FIG. 3B', C') was observed.

Compared with a previously characterised human cone arrestin (CAR) promoter, the expression levels provided by hG1.4 were higher in human cones and there was no ectopic expression in rod or retinal pigment epithelium (RPE) cells. In mice, cone promoters based on human red opsin promoters were not cone-specific and mediated expression in rods as well (Ye et al., 2016).

Example 3: Additional Optimization of the TCUs and Codon Optimisation of the Human CNGA3 Gene Changing the GGGCCG sequence in positions +5 to +10 relative to the transcription start site of the green opsin gene to TCTAGA, doubles the resultant expression level. This sequence alteration (M8), see SEQ ID NO:16, was therefore incorporated into the hG1.4 and hG1.7 constructs In addition, the coding sequence of CNGA3 was subjected to codon-optimisation, to attempt to improve the codon usage bias and CG content, and remove any cryptic processing sites and potential stem-loop structures in the mRNA.

Figure 4:
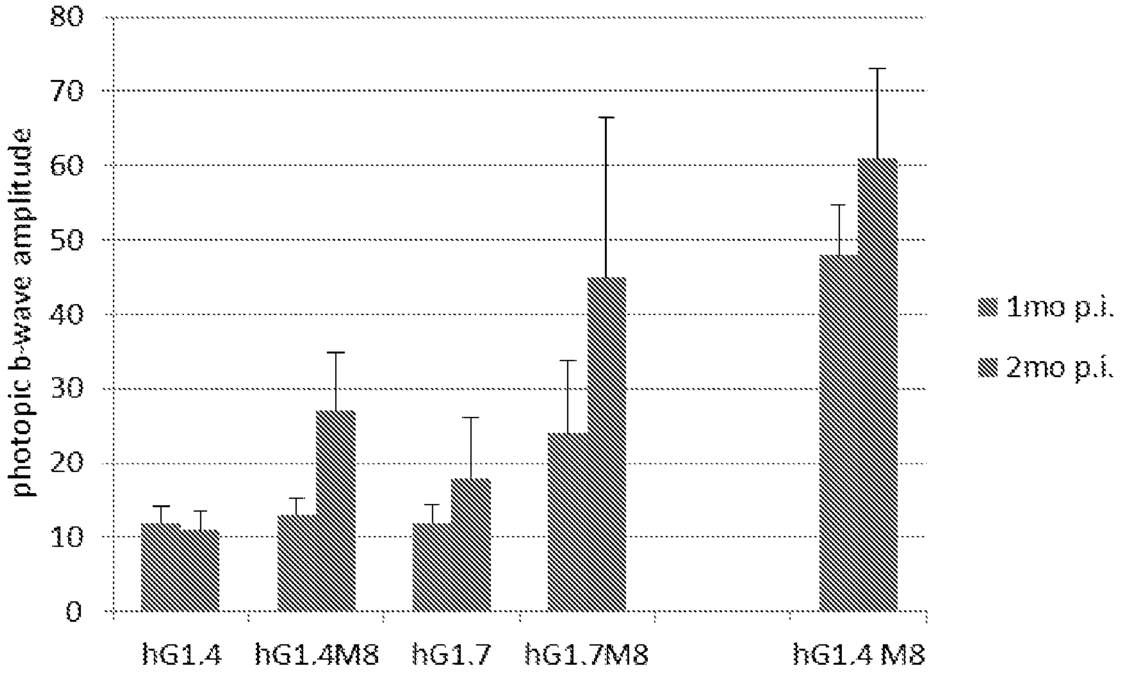
FIG. 4 illustrates that the inclusion of the M8 sequence in the TCU enhances rescue of phototopic responses in CNGA3 knockout mice. Photopic electroretinogram (ERG) responses of Cnga3 knockout mice treated with AAV2/8 vectors carrying codon optimised CNGA3 (coCNGA3) constructs driven by different TCUs with or without the M8 sequence are shown. ERG responses at 1 month (left bars) and 2 months (right bars) post-injection are shown. All animals were treated at 1 month of age, except for the group on extreme right; this group was treated at 2 weeks.

The hG1.4(M8) (SEQ ID NO:6) and hG1.7(M8) (SEQ ID NO:15) constructs were used in AAV2/8 vectors carrying a human codon optimised CNGA3 cDNA (coCNGA3) and the vectors' efficacy was determined in a CNGA3 knockout mouse model using electroretinographic (ERG) assessments of cone function. One month post vector administration, there was no clear advantage over vector without the M8 sequence, although the hG1.7(M8) vector appeared to show a small improvement over the corresponding vector without the M8 sequence (FIG. 4, left bars of column). When the ERG assessments in these animals were repeated at 2 months post administration, amplitudes in animals injected with 'M8' vectors further increased (FIG. 4, right bars of column), while amplitudes in animals injected with the standard vectors remained constant (hG1.4) or increased marginally (hG1.7). It was demonstrated that maximal expression levels are important to achieve a good functional rescue in Achromatopsia due to CNGA3 and these results indicate that inclusion of the M8 sequence in the constructs is beneficial for treatment.

Figure 5:
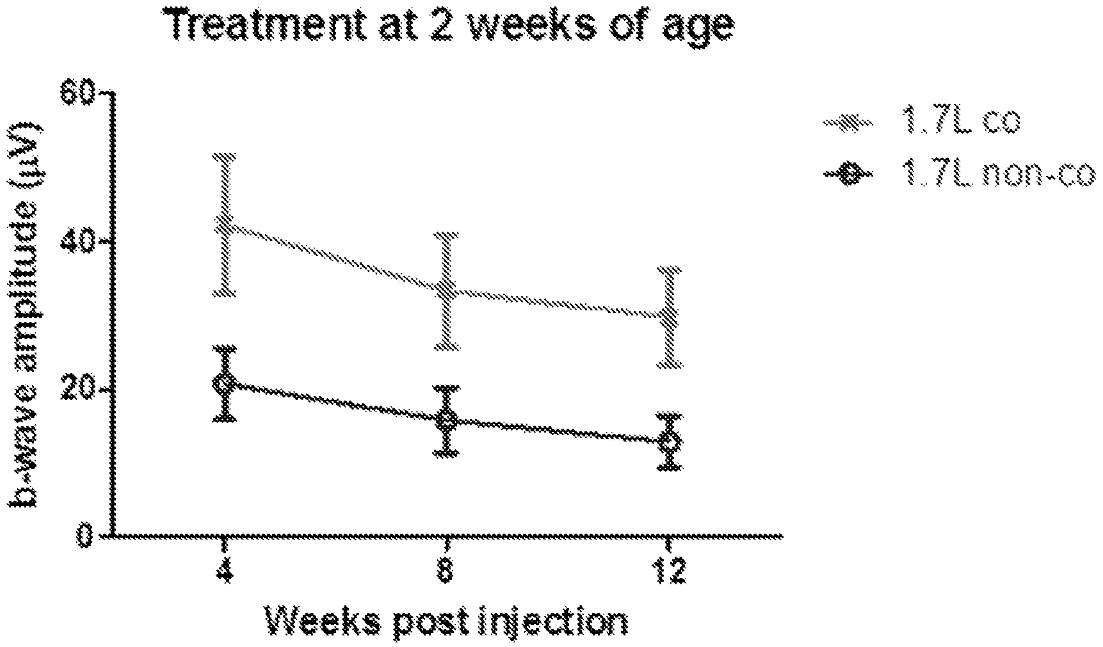
FIG. 5 illustrates that codon-optimized CNGA3 rescues phototopic responses in CNGA3 knockout mice more effectively than the wild type CNGA3 gene. Photopic ERG responses in Cnga3 knockout mice treated with AAV2/8 vectors carrying codon optimised CNGA3 ("co") and wild type CNGA3 constructs ("non-co").

The codon-optimised CNGA3 gene rescued photopic responses in Cnga3 knockout mouse more effectively than wild type human CNGA3 gene (FIG. 5). Constructs carrying the red opsin promoter (1.7L) driving either the wild type human CNGA3 gene or a codon optimised human CNGA3 gene were packaged in an AAV2/8 serotype and injected subretinally in Cnga3-deficient mice. Photopic ERG responses were assessed at 1 month and 2 months post injection. ERG responses in animals receiving the codon-optimised vector were consistently higher than in animals receiving the wild type gene (FIG. 5).

Figure 6:
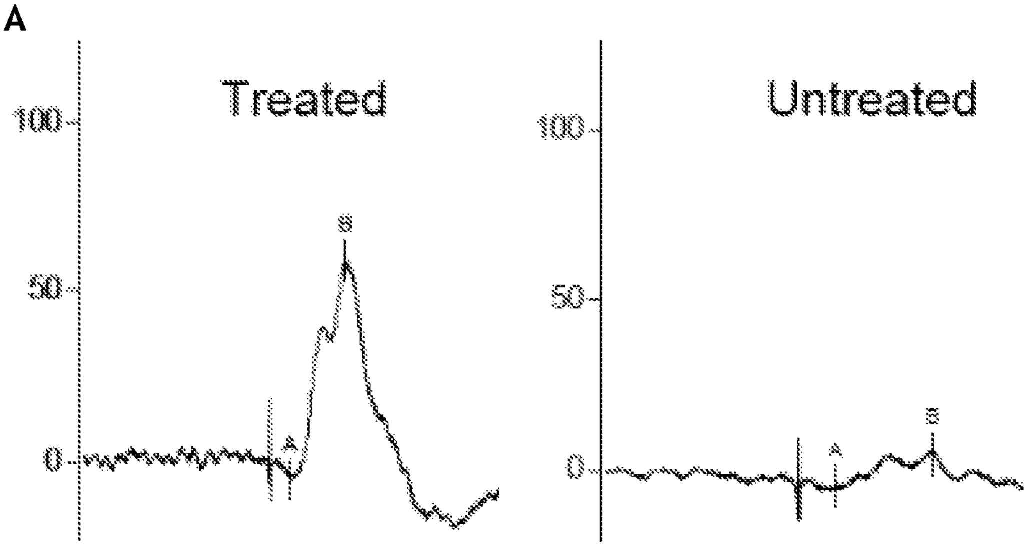
FIG. 6 illustrates that an AAV2/8 vector expressing CNGA3 under control of the hG1.4 TCU is effective in restoring cone function in CNGA3 knockout mice. (A) Photopic ERG traces of an AAV8-treated and untreated Cnga3 knockout mouse. A- and B-waves are annotated. Y axis denotes μV. Luminosity settings: 10 $Cdsm^{-2}$. (B) Photopic ERG responses of Cnga3 knockout mice treated with either AAV2/8-hG1.4(M8).coCNGA3 or AAV2/5-hG1.4 (M8).coCNGA3. Luminosity settings: 10 $Cdsm^{-2}$.
Figure 6:
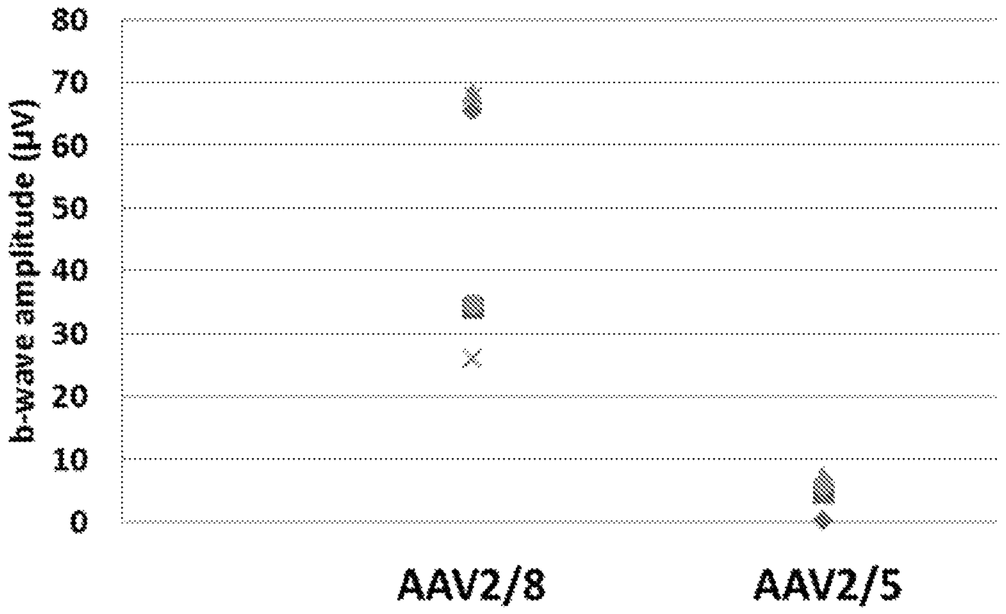

Example 4: AAV2/8 Vectors Expressing CNGA3 Can Rescue Photopic Responses in CNGA3 Knockout Mouse, While the Cooresponding AA2/5 Construct Provides Minimal Rescue To assess the ability of AAV2/5 and AAV2/8 vectors expressing CNGA3 to rescue photopic responses, AAV2/8-hG1.4(M8).coCNGA3 and AAV2/5-hG1.4(M8).coCNGA3 viral vectors were injected subretinally into 1 month old cnga3 knockout mice. Photopic ERG responses were assessed 4 weeks post administration. The inventors observed robust photopic responses in AAV2/8 treated eyes with ERG b-wave amplitudes of up to 70 μV (FIGS. 6A and B). The eyes that received subretinal injections in both hemispheres (superior/inferior) showed the greatest improvement in ERG b-wave amplitude. By comparison, a wild-type mouse has amplitudes of around 100-120 μV at the same experimental settings. There were no responses from untreated eyes and AAV2/5 treated eyes provide minimal responses (FIGS. 6A and B). This data shows that the AAV2/8-hG1.4(M8).coCNGA3 vector is able to provide high levels of CNGA3 expression and restore cone-function in CNGA3 knockout mice to that of approximately 60% of wild-type, as measured by cone ERG b-wave amplitudes.

Figure 7:
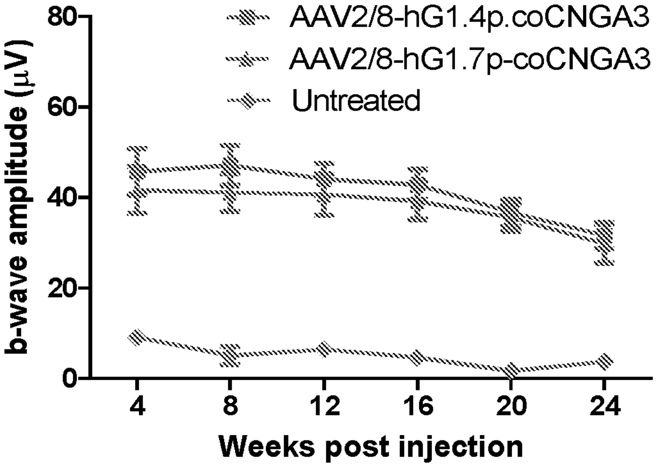
FIG. 7 illustrates the long-term in vivo rescue of retinal sensitivity with AAV2/8 vectors expressing CNGA3 under control two different optimized TCUs up to 6 months following treatment. Cnga3 deficient mice were sub-retinally injected at the age of 2 weeks with either AAV2/8-hG1.4(M8).coCNGA3 (n=14) or AAV2/8-hG1.7(M8).coCNGA3 (n=13) (titre $1\times10^{12}$ vg/ml for both). Untreated (n=3). Luminosity settings: 10 Cdsm−2.

To further demonstrate that the rescue of retinal sensitivity by AAV2/8 vectors expressing CNGA3 was long-lasting, Cnga3 deficient mice were sub-retinally injected at the age of 2 weeks with either AAV2/8-hG1.4(M8).coCNGA3 (n=14) or AAV2/8-hG1.7(M8).coCNGA3 (n=13) (titre $1\times10^{12}$ vg/ml for both), or left untreated (n=3). Both transfection with either vector lead to a sustained rescue of retinal sensitivity up to six months following treatment (FIG. 7).

Example 5: AAV2/8 Vectors Expressing CNGA3 Promote Long-Term Cone Survival

The ability of AAV2/8 vectors expressing CNGA3 to promote survival of cones was assessed by injecting a Cnga3-deficient mouse at 2 weeks of age with AAV2/8-hG1.7(M8).coCNGA3. A C57BL/6J mouse of 3-4 month of age, which did not receive an injection, served as a control for healthy cones. Retinas were isolated and stained with cone arrestin and cleared.

Figure 8:
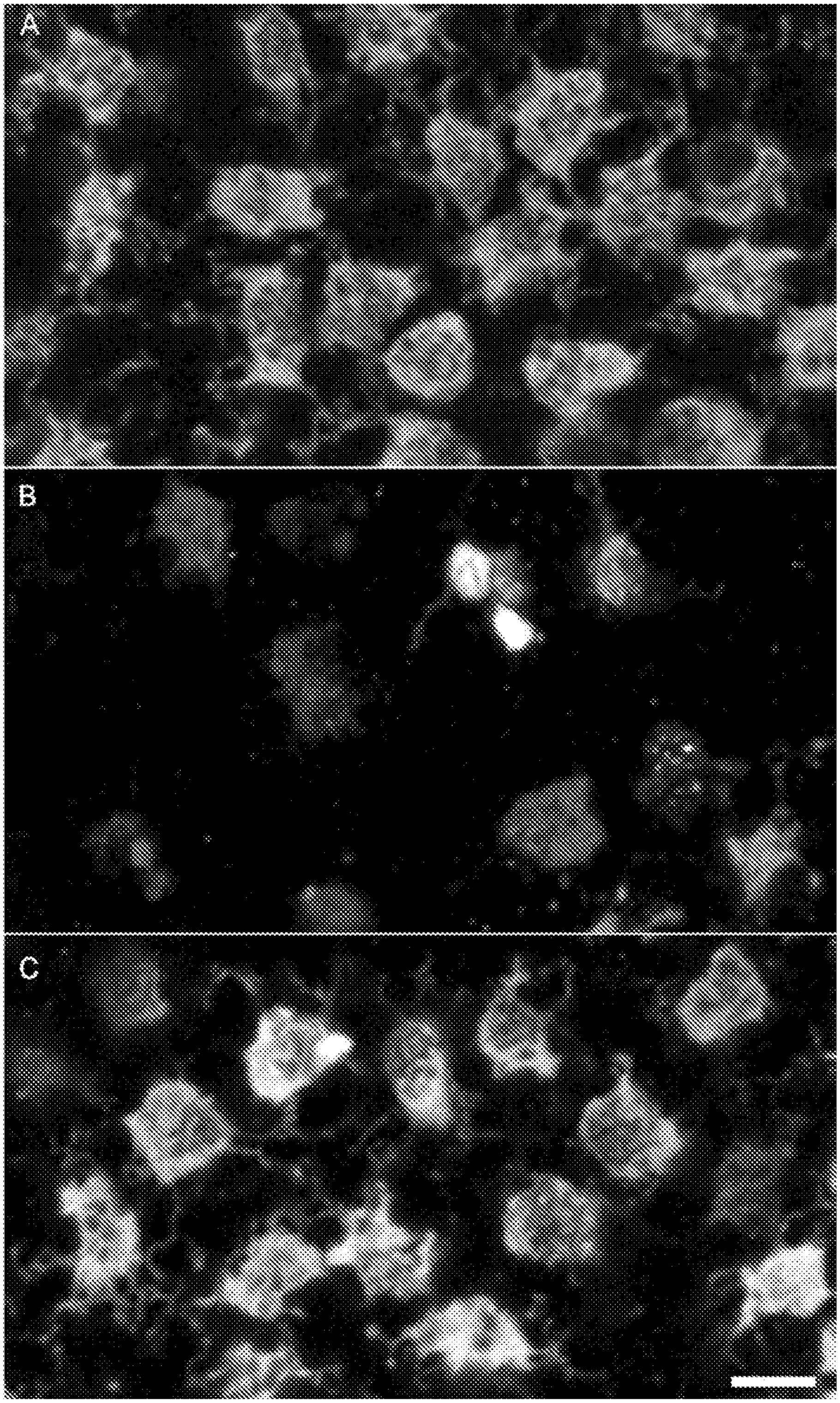
FIG. 8 illustrates the increased survival of cones in vivo 3-4 months following treatment with AAV2/8 vectors expressing CNGA3 under control of the hG1.7 TCU. Single plane confocal images of flat mount retina from a C57BL/6J mouse of 3-4 month of age (A), or a Cnga3 deficient mouse of the same age uninjected (B) or injected (C) with AAV2/8-hG1.7(M8).coCNGA3 at 2 weeks of age. The retinas were stained with cone arrestin and cleared. Scale bar: 5 μm.

Cnga3-deficient retinas transduced with AAV2/8-hG1.7 (M8).coCNGA3 (see FIG. 8C) showed survival of cones in vivo 3-4 months following treatment. The extent of the survival was similar to cone survival of the healthy control (see FIG. 8A) and significantly increased as compared to uninjected Cnga3-deficient retinas (see FIG. 8B).

Figure 9:
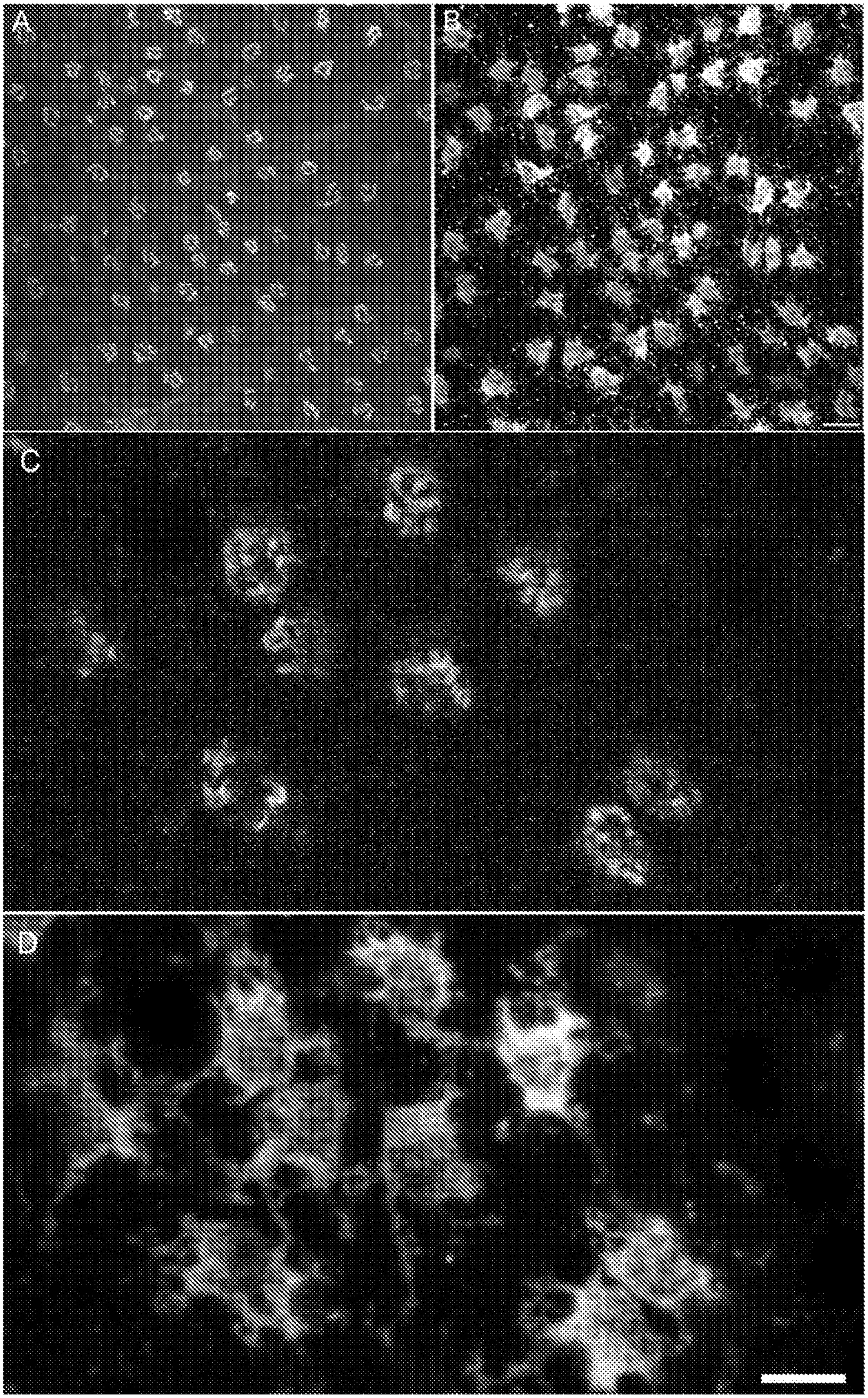
FIG. 9 illustrates the long-term increased survival of cones in vivo, 13 months following treatment with an AAV2/8 vector expressing CNGA3 under control of the hG1.7 TCU. Z-projection confocal images (A, B) or single plane confocal images (C, D) of flat mount retina from a Cnga3-deficient mouse of 14 months of age injected with AAV2/8-hG1.7(M8).coCNGA3 at 2 weeks of age. The untreated shows no positive PNA staining at this age. The retinal flat mounts were stained with PNA (A, C) and cone arrestin (B, D) and cleared. Scale bar: 10 μm (A, B), 5 μm (C, D).

The ability of AAV2/8 vectors expressing CNGA3 to promote cone survival was long lasting and could still be observed 13 months following vector treatment (see FIG. 9).

Example 6: AAV2/8 Vectors Expressing CNGA3 Preserve of Synaptic Connectivity In Vivo To assess the ability of AAV2/8 vectors expressing CNGA3 to improve the synaptic integrity between cone cells and supporting neurons (bipolar cells), a Cnga3-deficient mouse at 2 weeks of age was injected with AAV2/8-hG1.7(M8).coCNGA3. 3-4 months following treatment, the retinas were isolated and stained with Gpr179 and PNA and then cleared. Synaptic connectivity was determined by measuring the signal intensity of the synaptic marker Gpr179 in single plane confocal images of flat mount retinas. Leica Las X software was used to process the image. Gpr179 stainings were traced by drawing a free hand line on several cone pedicle related Gpr179 staining (PNA staining was used to confirm the cone pedicles) and more than 10 rod spherule related Gpr179 staining (A). Signal intensity was output (B; white line: Gpr179, red line: PNA). Peaks of signal intensity from each origin were averaged, and cone pedicle to rod spherule related GPr179 ratio (CP/RS) was calculated. CP/RS from four different locations were used for statistical analysis (Bonferroni's Multiple Comparison Test (ns: $p>0.05$, **: $p\leq0.01$, *: $p\leq0.05$)). Retinas from an uninjected Cnga3-deficient mouse and an uninjected C57BL/6J mouse of the same age (3-4 months) served as negative and positive controls, respectively.

Figure 10:
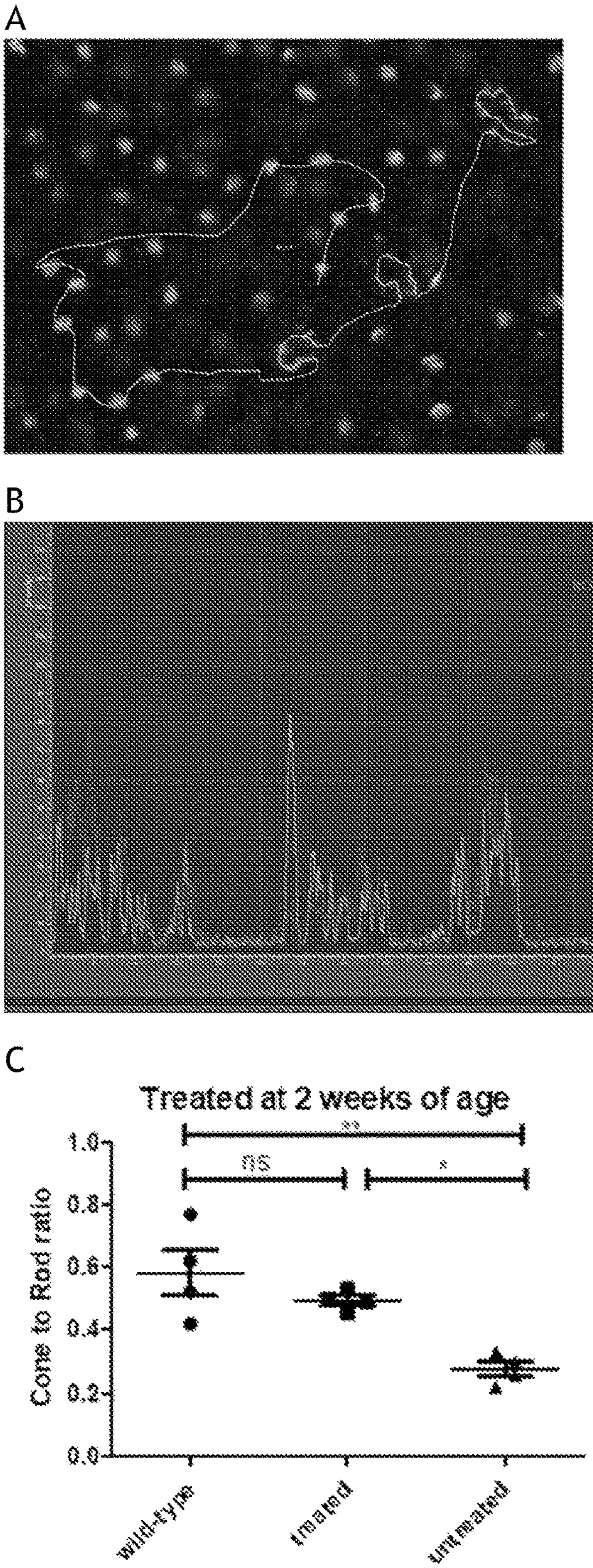
FIG. 10 illustrates a quantification of improvement of synaptic integrity between cone cells and supporting neurons (bipolar cells) in vivo 3-4 months following treatment with an AAV2/8 vector expressing CNGA3 under control of the hG1.7 TCU. The assessment was done using signal intensity of the synaptic marker GPr179. Analysis of signal intensity of GPr179 staining was performed on single plane confocal images of flat mount retinas from a C57BL/6J mouse of 3-4 month of age, or a Cnga3 deficient mouse of the same age uninjected or injected with AAV2/8-hG1.7 (M8).coCNGA3 at 2 weeks of age. The retinas were stained with GPr179 and PNA and then cleared. Gpr179 stainings were traced by drawing a free hand line on several cone pedicle related Gpr179 staining (PNA staining was used to confirm the cone pedicles) and more than 10 rod spherule related GPr179 staining (A). Signal intensity was output (B; white line:Gpr179, dark line: PNA). Peaks of signal intensity from each origin were averaged, and cone pedicle to rod spherule related GPr179 ratio (CP/RS) was calculated. CP/RS from four different locations were used for statistical analysis (Bonferroni's Multiple Comparison Test (ns: $p>0.05$, **: $p\leq0.01$, *: $p\leq0.05$)). Error bar indicates SEM. (C).

As shown in FIG. 10, transduction of Cnga3-deficient retinas with an AAV2/8 vectors expressing CNGA3 leads to synaptic connectivity similar to that of a healthy control mouse and significantly improved as compared to uninjected Cnga3-deficient retinas.

Example 7: coCNGA3 Delivery Using AAV2/8 Provides Greater Benefit than Delivery Using Novel Strong AAV Serotypes AAV-Anc80, AAV-44.9, and AAV5

A number of different AAV serotypes and capsids are available for the expression of genes. For instance, the newly developed Anc80-L65 capsid was shown to have efficient tropism to photoreceptors and to be comparable or even superior to AAV8. Further, the novel serotype AAV44.9 has also been shown to exhibit efficient transduction and high expression in photoreceptor cells when tested in combination with a fluorescent marker. Thus, the ability of four different AAV vectors—Anc80-L65, AAV44.9, AAV5, and AAV8—to express coCNGA3 and provide sustained ERG responses was compared.

Figure 11:
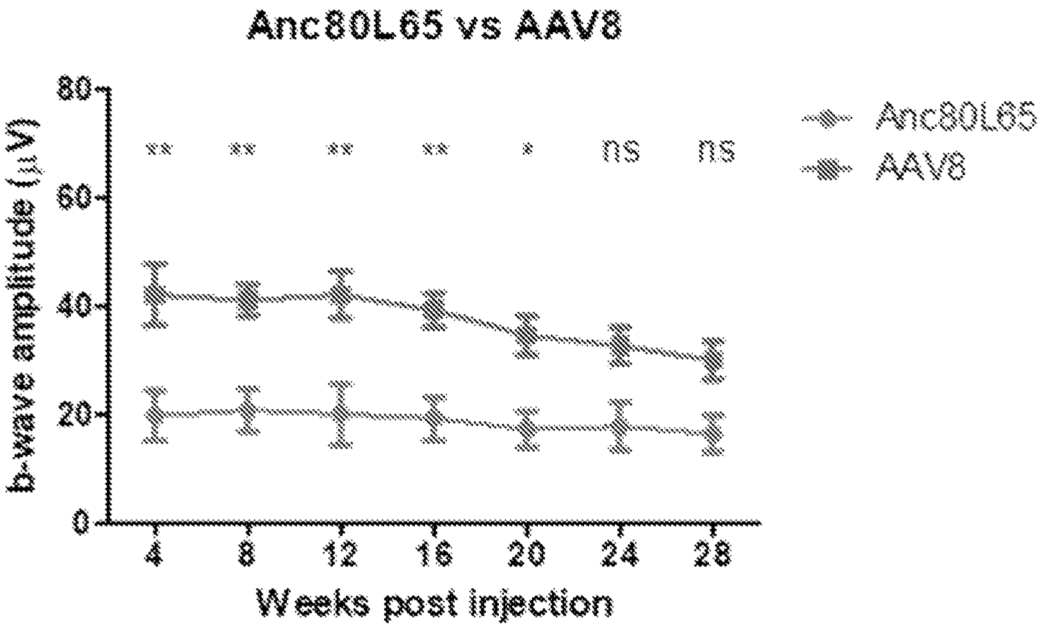
FIG. 11 illustrates that expression of CNGA3 under control of the hG1.4 TCU in AAV8 vectors lead to improved ERG responses in CNGA3 deficient mice as compared to AAV vectors Anc80L65, AAV44.9, or AAVS, respectively. (A). Comparison of Anc80L65 and AAV8. AAV-Anc80L65 or AAV8 carrying the hG1.4(M8).coCNGA3 expression cassette were delivered to Cnga3-deficient mice at the age of 2 weeks. **: $p\leq0.01$, *: $p\leq0.05$. Error bar indicates SEM. (B). Comparison of AAV8 and AAV44.9 for delivery of CNGA3 in Cnga3-deficient mice at 4 weeks of age. Error bar indicates SEM. (C) Comparison of AAV5 and AAV8. AAV5 or AAV8 carrying the hG1.4(M8).coCNGA3 expression cassette were delivered to Cnga3-deficient mice at the age of 2 weeks. **: $p\leq0.01$, *: $p\leq0.05$. Error bar indicates SEM.
Figure 11:
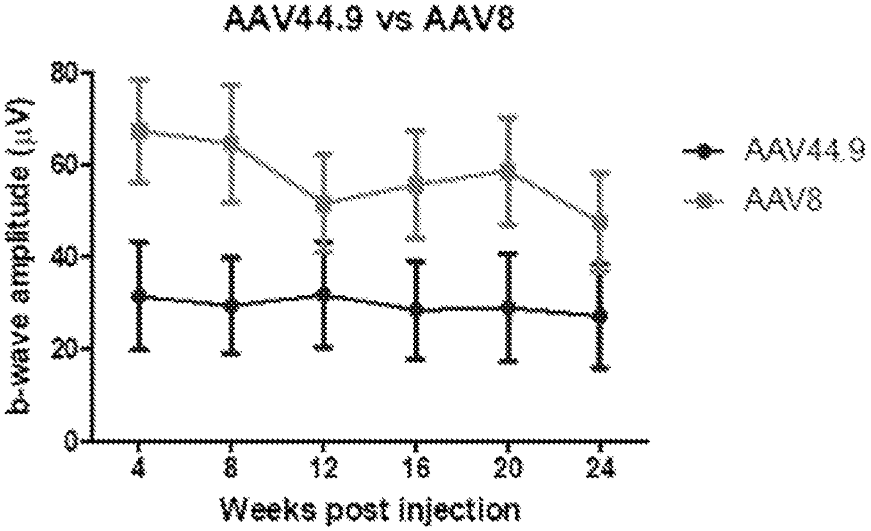
Figure 11:
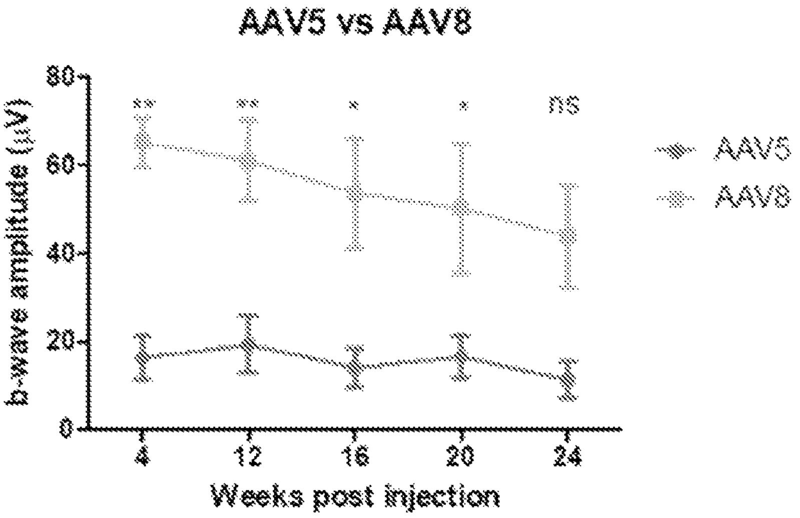

The respective vectors carrying the hG1.4(M8)-coCNGA3 expression cassette ($1.0\times10^{12}$ vg/mL) were delivered to subretinal space of Cnga3-deficient mice at the age of 2 weeks, and single flash photopic ERG was recorded at different time points post injection (see FIG. 11). The light stimulus of 10 cd·s/m$^2$ was used for analysis. As shown in FIG. 11, AAV8-mediated gene transfer led to higher ERG responses as compared to either Anc80-L65 (see FIG. 11A), AAV44.9 (see FIG. 11B), or AAV5 (see FIG. 11C and FIG. 6).

Figure 12:
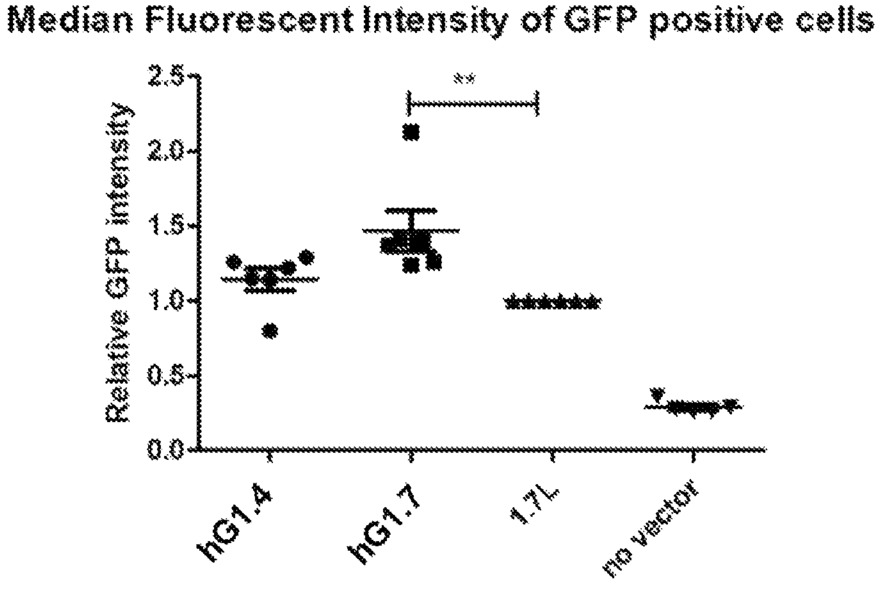
FIG. 12 illustrates improved expression levels for the TCUs hG1.4 and hG1.7 carrying the M8 mutation as compared to the expression levels observed for known cone promoters. (A) hEBs of 17-19 weeks of age were transduced with AAVShH10 expressing eGFP under two different green opsin promoters (hG1.4 and hG1.7) and were collected 2 weeks later (n=6-8 for each promoter). Following dissociation, cells were analysed for relative median fluorescence intensity (MFI) in GFP positive cells (relative MFI in the hEBs transduced with AAVShH10-eGFP analysed on the same day experiment were calculated as ratio to MFI in the EBs transduced with AAV ShH10-1.7L-eGFP) by flow cytometry. Asterisk indicates significant difference ($p\leq0.01$). Error bar indicates SEM. (B) Photopic ERG responses of treated Cnga3 knockout mice treated with either AAV2/8-CAR-CNGA3 or left untreated. Y axis denotes μV. Luminosity settings: 10 $Cdsm^{-2}$.
Figure 12:
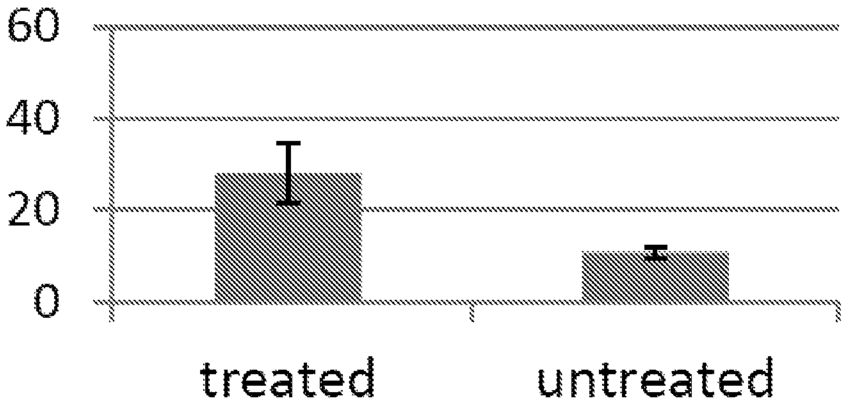

Example 8: Comparison of Optimized TCUs with Previously Known, Cone-Specific Promoters To compare the expression level of the TCUs disclosed herein with one of the strongest cone-specific promoters available (1.7L), human embryoid bodies (hEBs) of 17-19 weeks of age were transduced with AAV vector AAVShH10 expressing eGFP under control of hG1.4(M8), hG1.7(M8) or P1.7L, respectively, and collected 2 weeks later (n=6-8 for each promoter). Following dissociation, cells were analysed for relative median fluorescence intensity (MFI) in GFP positive cells. The relative MFI in the hEBs transduced with the different vectors was assessed by flow cytometry and calculated as ratio to MFI in the EBs transduced with AAV ShH10-1.7L-eGFP. As shown in FIG. 12A, the construct hG1.7 provides an approximately 50% increase in GFP expression as compared to the previously known promoter 1.7L.

Additionally, an AAV2/8 vector driving hCNGA3 from the hCAR (human cone arrestin) promoter in CNGA3 knockout mice was tested. Photopic responses rescue did not exceed 30% of wild-type levels (FIG. 12B).

It has been reported that an AAV2/5(Y719F) vector and a mouse blue cone opsin promoter can be used to rescue CNGA3 knockout mice. In that study, photopic ERG amplitudes reached 30% of wild-type when injected at P12 and assessed 10 weeks post treatment (Michalakis et al., 2010). Recently an AAV5 vector and a 2.1 kb red opsin promoter has been used to rescue CNGA3-deficient sheep. In this study, there was a doubling of cone flicker ERG when compared to untreated (Banin et al, 2015). However, both these promoters are known to function only in a subset of human cones (blue cone opsin promoter is active only in blue cones and the 2.1 red opsin promoter active in only red cones).

A study using a AAV2/5 vector with a CBA promoter to express murine CNGA3 in CNGA3 knockout mice by the Hauswirth lab showed rescue of up to 70% of wild type ERG cone b-wave amplitudes when mice were treated very early on (P14 assessed 3 weeks post treatment—viral titre 1E13) (Pang et al., 2012). The inventors achieved similar efficacy in rescuing photopic vision treating the same animal model later in life (1 month—viral titre 7E12). While Achromatopsia in humans is a stationary disorder, the CNGA3 mouse model suffers from cone cell death within the first month indicating that earlier treatment is beneficial. The non-specific CBA promoter is unlikely to be used in a CNGA3 trial, but supports the inventors' contention that high levels of CNGA3 expression is important for optimal rescue.

REFERENCES

Altschul S. F. A protein alignment scoring system sensitive at all evolutionary distances. 1993 J Mol Evol 36:290-300.

Altschul S. F. et al Basic local alignment search tool. 1990 J Mol Biol 215:403-10.

Banin E., Gootwine E., Obolensky A., Ezra-Elia R., Ejzenberg A., Zelinger L., Honig H., Rosov A., Yamin E., Sharon D., Averbukh E., Hauswirth W. W., Ofri R. Gene Augmentation Therapy Restores Retinal Function and Visual Behavior in a Sheep Model of CNGA3 Achromatopsia. 2015 Mol Ther. September; 23(9):1423-33.

Davidoff et al. Purification of recombinant adeno-associated virus type 8 vectors by ion exchange chromatography generates clinical grade vector stock. 2004 J. Virol. Methods 121; 209-215.

Devereux J. et al. A comprehensive set of sequence analysis programs for the VAX. 1984 Nucleic Acids Research 12, 387-395.

Gao G. P., Alvira M. R., Wang L., Calcedo R., Johnston J., Wilson J. M. Novel adeno-associated viruses from rhesus monkeys as vectors for human gene therapy. Proc. Natl. Acad. Sci. USA, 99 (18) (2002), pp. 11854-11859

Hawes N., Wang X., Hurd R. E., Wang J., Davisson M. T., Nusinowitz S., Heckenlively J. R., Chang B. A Point Mutation in the Cnga3 Gene Causes Cone Photoreceptor Function Loss (cpfl5) in Mice. 2006 *Invest Ophthalmol Vis Sci* 47: E-Abstr 4579

Henikoff S. and Henikoff J. G. Amino acid substitution matrices from protein blocks. 1992 Proc. Natl. Acad. Sci. USA 89: 10915-10919.

Karlin S. and Altschul S. F. Applications and statistics for multiple high-scoring segments in molecular sequences. 1993 Proc. Natl. Acad. Sci. USA 90: 5873-5787.

Michalakis S., Mülfriedel R., Tanimoto N., Krishnamoorthy V., Koch S., Fischer M. D., Becirovic E., Bai L., Huber G., Beck S. C., Fahl E., Büning H., Paquet-Durand F., Zong X., Gollisch T., Biel M., Seeliger M. W. Restoration of cone vision in the CNGA3−/− mouse model of congenital complete lack of cone photoreceptor function. 2010 Mol Ther. December; 18(12):2057-63.

Pang J. J., Deng W. T., Dai X., Lei B., Everhart D., Umino Y., Li J., Zhang K., Mao S., Boye S. L., Liu L., Chiodo V. A., Liu X., Shi W., Tao Y., Chang B., Hauswirth W. W. AAV-mediated cone rescue in a naturally occurring mouse model of CNGA3-Achromatopsia. 2012 PLoS One. 7(4): e35250.

Shabaan S. A. and Deeb S. S. Functional Analysis of the Promoters of the Human Red and Green Visual Pigment Genes. 1998 IOVS 39: 885-896.

Smallwood P. M., Wang Y., Nathans J. Role of a Locus Control Region in the mutually exclusive expression of human red and green cone pigment genes. 2002 Proc Natl Acad Sci USA. January 22; 99(2):1008-11.

Ye G. J., Budzynski E., Sonnentag P., Nork T. M., Sheibani N., Gurel Z., Boye S. L., Peterson J. J., Boye S. E., Hauswirth W. W., Chulay J. D. Cone-Specific Promoters for Gene Therapy of Achromatopsia and Other Retinal Diseases. 2016 Hum Gene Ther. January; 27(1):72-82.

SEQUENCE FORMATION 1.2 kb fragment of the M/L opsin Locus Control Region (LCR)

SEQ ID NO: 1

```
TAGGAATAGAAGGGTGGGTGCAGGAGGCTGAGGGGTGGGGAAAGGGCATGGGTGTTTCATGAGGACAGAGCTTCCGT

TTCATGCAATGAAAAGAGTTTGGAGACGGATGGTGGTGACTGGACTATACACTTACACACGGTAGCGATGGTACACT

TTGTATTATGTATATTTTACCACGATCTTTTTAAAGTGTCAAAGGCAAATGGCCAAATGGTTCCTTGTCCTATAGCT

GTAGCAGCCATCGGCTGTTAGTGACAAAGCCCCTGAGTCAAGATGACAGCAGCCCCCATAACTCCTAATCGGCTCTC

CCGCGTGGAGTCATTTAGGAGTAGTCGCATTAGAGACAAGTCCAACATCTAATCTTCCACCCTGGCCAGGGCCCCAG

CTGGCAGCGAGGGTGGGAGACTCCGGGCAGAGCAGAGGGCGCTGACATTGGGGCCCGGCCTGGCTTGGGTCCCTCTG

GCCTTTCCCCAGGGGCCCTCTTTCCTTGGGGCTTTCTTGGGCCGCCACTGCTCCCGCTCCTCTCCCCCCATCCCACC

CCCTCACCCCCTCGTTCTTCATATCCTTCTCTAGTGCTCCCTCCACTTTCATCCACCCTTCTGCAAGAGTGTGGGAC

CACAAATGAGTTTTCACCTGGCCTGGGGACACACGTGCCCCCACAGGTGCTGAGTGACTTTCTAGGACAGTAATCTG

CTTTAGGCTAAAATGGGACTTGATCTTCTGTTAGCCCTAATCATCAATTAGCAGAGCCGGTGAAGGTGCAGAACCTA

CCGCCTTTCCAGGCCTCCTCCCACCTCTGCCACCTCCACTCTCCTTCCTGGGATGTGGGGGCTGGCACACGTGTGGC

CCAGGGCATTGGTGGGATTGCACTGAGCTGGGTCATTAGCGTAATCCTGGACAAGGGCAGACAGGGCGAGCGGAGGG

CCAGCTCCGGGGCTCAGGCAAGGCTGGGGGCTTCCCCCAGACACCCCACTCCTCCTCTGCTGGACCCCCACTTCATA

GGGCACTTCGTGTTCTCAAAGGGCTTCCAAATAGCATGGTGGCCTTGGATGCCCAGGGAAGCCTCAGAGTTGCTTAT

CTCCCTCTAGACAGAAGGGGAATCTCGGTCAAGAGGGAGAGGTCGCCCTGTTCAAGGCCACCCAGCCAGCTCATGGC

GGTAATGGGACAAGGCTGGCCAGCCATCCCACCCTCAGAAGGGACCCGGTGGGGCAGGTGATCTCAGAGGAGGCTCA

CTTCTGGGTCTCACATTCTTG
```

2.0 kb M opsin promoter fragment, 500 bp fragment of SEQ ID NO: 3 underlined, UTR in italics with no M8 sequence

SEQ ID NO: 2

```
TAAAAAGCAAGTCTTGCCAGGGCAGTGGTGTGCACCTGTGGTCCCAGCTACTCAGGATGCTGAGGCAGGAGGATTAC

TTGTGCCCAGCAAGTAGAGGCTGCAGTGACCTGTGACTGTGCTACTGCCCTCCAACCTGGGTGACAGAGTGAGACCT

TGTCTCAAAAAAAAAAGAGCGGGGGGGGGGGGCCGGGCCGGGCGTGGTGGCTCACAGCTGTAATCCCAGCACTTTGG
```

-continued

GAAGCCAAGGCGGGTGGATCACTTGAGGTCAGGAGTTTGAGACCATCATGGTCAACACTGCGAAACACTGTCCCTAC

TAAAAATACAAAAATTAGCCGGGCATGGTGGCACACACCTGTAATCCCAGCTACTGGGGAGGCTGAGGCAGGAGAAT

TGCTTGAGCCGGGGAGACGGAGGTTGCAGTGAGCCGAGACTGCGCCACTGCACTCCAGCCTGACTGACAAGAGTGAG

ATTGTCTCAAAAAAAAAAAAAAAGTAATCACTAGAAAAGAAGCTACATATGTACATAACATCCAAATAACCAAGAGG

AGAAAAAAATGGACTTGATTAATCAAAACAAAAACAAAAAGAAAGAAAGAAAGGGGGAGAAAATAAAACAAGGGC

TGGGTGTGCTGGCTCATGCCTGTAATCCCAGCACTTTGGAAGCCAAGGTGGGTGGATCTCTTGAGCTCAGGAGGTCA

AGACCAGCCTGGGCAACATGGCGAAACCCCGTCTCTATTAAAAAAAAAATTAATACAACAATTATCCTGGAGTGGTG

GTGCACACCTGTAGTCCCAGCTACCCAGGACGCTGAGACGGGAGGATCGCTTGATCCCGGGGATGTCGAGGCTGCCG

TGATCGCACCACTGCCCTCCAGCCAGGGTGGCAGACTGAGACCCCATCTCAAAAAATAAATAAATAAAAGCAAACAA

GAAAAAAAAAGGCTTGAAACATATCTGATAGATAAAGGGCTAATCAACACAATATATAAAGAACTGCAAATCAGTAA

ACTAAGAGCAAATAACCCAATATAAAGACATTAAAGGGTAGCCACGGACATCTCAGACGACGAAAAACAAAAGACAG

TAAACGTATAATAAAACATGTAATTGCAAGGTGATCCGGGAATAGTAAGCGAAAAGCAACAATTAAATACTATTTTC

TCATCCACCAGAACGCCAAAAATTAAAAAGCCTAACAATGTCCAGGGCTGGCGAGAATGTGGCAGAAGGTGATGTCA

CATACCCTGCAAGTGGGAATCTAAACAGATTCAGGGTTTTGGTTTTTTTTTAATCGCAATTAGGTGGCCTGTTAAAT

TTTTTTTCTTGAGACAGAGTTTTGCTCTTGTTGCCCAGGCTGGAGTGCAATGGCTCGATCTTGGCTCACCGCAACCT

CGACCTCCCAGGTACAAGCGATTCTCCTGTCTCAGCCTCCCAAGTAGCTGGGAGTACAGGTATTTGCCACTAAGCCC

AGCTAATTGTTTTTTATTTAGTAGAAACGGGGTTTCACCATGTTAGTCAGGCTGGTCGGGAACTCCTGACCTCAGGA

GATCTACCCGCCTTGGCCTCCCAAAGTGCTGGGATTACAGGCGTGTGCCACTGTGCCCAGCCACTTTTTTTTAGACA

GAGTCTTGGTCTGTTGCCCAGGCTAGAGTTCAGTGGCGCCATCTCAGCTCACTGCAACCTCCGCCTCCCAGATTCAA

GCGATTCTCCTGCCTCGACCTCCCAGTAGCTGGGATTACAGGTTTCCAGCAAATCCCTCTGAGCCGCCCCCGGGGGC

TCGCCTCAGGAGCAAGGAAGCAAGGGGTGGGAGGAGGAGGTCTAAGTCCCAGGCCCAATTAAGAGATCAGATGGTGT

AGGATTTGGGAGCTTTTAAGGTGAAGAGGCCCGGGCTGATCCCACTGGCCGGTATAAAGCACCGTGACCCTCAGGTG

ACGCACCA*GGGCCGGCTGCCGTCGGGGACAGGGCTTTCCATAGCC*

500 bp M opsin fragment, UTR in italics, M8 mutation underlined

SEQ ID NO: 3

ACAGGTATTTGCCACTAAGCCCAGCTAATTGTTTTTTATTTAGTAGAAACGGGGTTTCACCATGTTAGTCAGGCTGG

TCGGGAACTCCTGACCTCAGGAGATCTACCCGCCTTGGCCTCCCAAAGTGCTGGGATTACAGGCGTGTGCCACTGTG

CCCAGCCACTTTTTTTTAGACAGAGTCTTGGTCTGTTGCCCAGGCTAGAGTTCAGTGGCGCCATCTCAGCTCACTGC

AACCTCCGCCTCCCAGATTCAAGCGATTCTCCTGCCTCGACCTCCCAGTAGCTGGGATTACAGGTTTCCAGCAAATC

CCTCTGAGCCGCCCCCGGGGGCTCGCCTCAGGAGCAAGGAAGCAAGGGGTGGGAGGAGGAGGTCTAAGTCCCAGGCC

CAATTAAGAGATCAGATGGTGTAGGATTTGGGAGCTTTTAAGGTGAAGAGGCCCGGGCTGATCCCACTGGCCGGTAT

AAAGCACCGTGACCCTCAGGTGACGCA*CCATCTAGAGCTGCCGTCGGGGACAGGGCTTTCCATAGCC* variant of hG1.7(M8) construct, 1.2 kb M/L opsin LCR fragment, 500 bp M opsin fragment, UTR in italics, M8 mutation underlined

SEQ ID NO: 4

TAGGAATAGAAGGGTGGGTGCAGGAGGCTGAGGGGTGGGGAAAGGGCATGGGTGTTTCATGAGGACAGAGCTTCCGT

TTCATGCAATGAAAAGAGTTTGGAGACGGATGGTGGTGACTGGACTATACACTTACACACGGTAGCGATGGTACACT

TTGTATTATGTATATTTTACCACGATCTTTTTAAAGTGTCAAAGGCAAATGGCCAAATGGTTCCTTGTCCTATAGCT

GTAGCAGCCATCGGCTGTTAGTGACAAAGCCCCTGAGTCAAGATGACAGCAGCCCCCATAACTCCTAATCGGCTCTC

CCGCGTGGAGTCATTTAGGAGTAGTCGCATTAGAGACAAGTCCAACATCTAATCTTCCACCCTGGCCAGGGCCCCAG

CTGGCAGCGAGGGTGGGAGACTCCGGGCAGAGCAGAGGGCGCTGACATTGGGGCCCGGCCTGGCTTGGGTCCCTCTG

GCCTTTCCCCAGGGGCCCTCTTTCCTTGGGGCTTTCTTGGGCCGCCACTGCTCCCGCTCCTCTCCCCCCATCCCACC

CCCTCACCCCCTCGTTCTTCATATCCTTCTCTAGTGCTCCCTCCACTTTCATCCACCCTTCTGCAAGAGTGTGGGAC

-continued

CACAAATGAGTTTTCACCTGGCCTGGGGACACACGTGCCCCCACAGGTGCTGAGTGACTTTCTAGGACAGTAATCTG

CTTTAGGCTAAAATGGGACTTGATCTTCTGTTAGCCCTAATCATCAATTAGCAGAGCCGGTGAAGGTGCAGAACCTA

CCGCCTTTCCAGGCCTCCTCCCACCTCTGCCACCTCCACTCTCCTTCCTGGGATGTGGGGGCTGGCACACGTGTGGC

CCAGGGCATTGGTGGGATTGCACTGAGCTGGGTCATTAGCGTAATCCTGGACAAGGGCAGACAGGGCGAGCGGAGGG

CCAGCTCCGGGGCTCAGGCAAGGCTGGGGGCTTCCCCCAGACACCCCACTCCTCCTCTGCTGGACCCCCACTTCATA

GGGCACTTCGTGTTCTCAAAGGGCTTCCAAATAGCATGGTGGCCTTGGATGCCCAGGGAAGCCTCAGAGTTGCTTAT

CTCCCTCTAGACAGAAGGGGAATCTCGGTCAAGAGGGAGAGGTCGCCCTGTTCAAGGCCACCCAGCCAGCTCATGGC

GGTAATGGGACAAGGCTGGCCAGCCATCCCACCCTCAGAAGGGACCCGGTGGGGCAGGTGATCTCAGAGGAGGCTCA

CTTCTGGGTCTCACATTCTTGACAGGTATTTGCCACTAAGCCCAGCTAATTGTTTTTTATTTAGTAGAAACGGGGTT

TCACCATGTTAGTCAGGCTGGTCGGGAACTCCTGACCTCAGGAGATCTACCCGCCTTGGCCTCCCAAAGTGCTGGGA

TTACAGGCGTGTGCCACTGTGCCCAGCCACTTTTTTTTAGACAGAGTCTTGGTCTGTTGCCCAGGCTAGAGTTCAGT

GGCGCCATCTCAGCTCACTGCAACCTCCGCCTCCCAGATTCAAGCGATTCTCCTGCCTCGACCTCCCAGTAGCTGGG

ATTACAGGTTTCCAGCAAATCCCTCTGAGCCGCCCCCGGGGGCTCGCCTCAGGAGCAAGGAAGCAAGGGGTGGGAGG

AGGAGGTCTAAGTCCCAGGCCCAATTAAGAGATCAGATGGTGTAGGATTTGGGAGCTTTTAAGGTGAAGAGGCCCGG

GCTGATCCCACTGGCCGGTATAAAGCACCGTGACCCTCAGGTGACGCA*CCATCTAGAGCTGCCGTCGGGGACAGGGC*

*TTTCCATAGCC*

200 bp M opsin fragment, UTR in italics, M8 mutation underlined

SEQ ID NO: 5

GATCGATTACAGGTTTCCAGCAAATCCCTCTGAGCCGCCCCCGGGGGCTCGCCTCAGGAGCAAGGAAGCAAGGGGTG

GGAGGAGGAGGTCTAAGTCCCAGGCCCAATTAAGAGATCAGATGGTGTAGGATTTGGGAGCTTTTAAGGTGAAGAGG

CCCGGGCTGATCCCACTGGCCGGTATAAAGCACCGTGACCCTCAGGTGACGCA*CCATCTAGAGCTGCCGTCGGGGAC*

*AGGGCTTTCCATAGCC* hG1.4(M8) construct: 1.2 kb M/L opsin LCR fragment, 200 bp M opsin fragment, UTR in italics, M8 mutation underlined

SEQ ID NO: 6

TAGGAATAGAAGGGTGGGTGCAGGAGGCTGAGGGGTGGGGAAAGGGCATGGGTGTTTCATGAGGACAGAGCTTCCGT

TTCATGCAATGAAAAGAGTTTGGAGACGGATGGTGGTGACTGGACTATACACTTACACACGGTAGCGATGGTACACT

TTGTATTATGTATATTTTACCACGATCTTTTTAAAGTGTCAAAGGCAAATGGCCAAATGGTTCCTTGTCCTATAGCT

GTAGCAGCCATCGGCTGTTAGTGACAAAGCCCCTGAGTCAAGATGACAGCAGCCCCCATAACTCCTAATCGGCTCTC

CCGCGTGGAGTCATTTAGGAGTAGTCGCATTAGAGACAAGTCCAACATCTAATCTTCCACCCTGGCCAGGGCCCCAG

CTGGCAGCGAGGGTGGGAGACTCCGGGCAGAGCAGAGGGCGCTGACATTGGGGCCCGGCCTGGCTTGGGTCCCTCTG

GCCTTTCCCCAGGGGCCCTCTTTCCTTGGGGCTTTCTTGGGCCGCCACTGCTCCCGCTCCTCTCCCCCCATCCCACC

CCCTCACCCCCTCGTTCTTCATATCCTTCTCTAGTGCTCCCTCCACTTTCATCCACCCTTCTGCAAGAGTGTGGGAC

CACAAATGAGTTTTCACCTGGCCTGGGGACACACGTGCCCCCACAGGTGCTGAGTGACTTTCTAGGACAGTAATCTG

CTTTAGGCTAAAATGGGACTTGATCTTCTGTTAGCCCTAATCATCAATTAGCAGAGCCGGTGAAGGTGCAGAACCTA

CCGCCTTTCCAGGCCTCCTCCCACCTCTGCCACCTCCACTCTCCTTCCTGGGATGTGGGGGCTGGCACACGTGTGGC

CCAGGGCATTGGTGGGATTGCACTGAGCTGGGTCATTAGCGTAATCCTGGACAAGGGCAGACAGGGCGAGCGGAGGG

CCAGCTCCGGGGCTCAGGCAAGGCTGGGGGCTTCCCCCAGACACCCCACTCCTCCTCTGCTGGACCCCCACTTCATA

GGGCACTTCGTGTTCTCAAAGGGCTTCCAAATAGCATGGTGGCCTTGGATGCCCAGGGAAGCCTCAGAGTTGCTTAT

CTCCCTCTAGACAGAAGGGGAATCTCGGTCAAGAGGGAGAGGTCGCCCTGTTCAAGGCCACCCAGCCAGCTCATGGC

GGTAATGGGACAAGGCTGGCCAGCCATCCCACCCTCAGAAGGGACCCGGTGGGGCAGGTGATCTCAGAGGAGGCTCA

CTTCTGGGTCTCACATTCTTGGATCGATTACAGGTTTCCAGCAAATCCCTCTGAGCCGCCCCCGGGGGCTCGCCTCA

GGAGCAAGGAAGCAAGGGGTGGGAGGAGGAGGTCTAAGTCCCAGGCCCAATTAAGAGATCAGATGGTGTAGGATTTG

-continued

GGAGCTTTTAAGGTGAAGAGGCCCGGGCTGATCCCACTGGCCGGTATAAAGCACCGTGACCCTCAGGTGACGCA*CCA*

*TCTAGAGCTGCCGTCGGGGACAGGGCTTTCCATAGCC* non-codon optimised CNGA3 cDNA

SEQ ID NO: 7

ATGGCCAAGATCAACACCCAATACTCCCACCCCTCCAGGACCCACCTCAAGGTAAAGACCTCAGACCGAGATCTCAA

TCGCGCTGAAAATGGCCTCAGCAGAGCCCACTCGTCAAGTGAGGAGACATCGTCAGTGCTGCAGCCGGGGATCGCCA

TGGAGACCAGAGGACTGGCTGACTCCGGGCAGGGCTCCTTCACCGGCCAGGGGATCGCCAGGCTGTCGCGCCTCATC

TTCTTGCTGCGCAGGTGGGCTGCCAGGCATGTGCACCACCAGGACCAGGGACCGGACTCTTTTCCTGATCGTTTCCG

TGGAGCCGAGCTTAAGGAGGTGTCCAGCCAAGAAAGCAATGCCCAGGCAAATGTGGGCAGCCAGGAGCCAGCAGACA

GAGGGAGAAGCGCCTGGCCCCTGGCCAAATGCAACACTAACACCAGCAACAACACGGAGGAGGAGAAGAAGACGAAA

AAGAAGGATGCGATCGTGGTGGACCCGTCCAGCAACCTGTACTACCGCTGGCTGACCGCCATCGCCCTGCCTGTCTT

CTATAACTGGTATCTGCTTATTTGCAGGGCCTGTTTCGATGAGCTGCAGTCCGAGTACCTGATGCTGTGGCTGGTCC

TGGACTACTCGGCAGATGTCCTGTATGTCTTGGATGTGCTTGTACGAGCTCGGACAGGTTTTCTCGAGCAAGGCTTA

ATGGTCAGTGATACCAACAGGCTGTGGCAGCATTACAAGACGACCACGCAGTTCAAGCTGGATGTGTTGTCCCTGGT

CCCCACCGACCTGGCTTACTTAAAGGTGGGCACAAACTACCCAGAAGTGAGGTTCAACCGCCTACTGAAGTTTTCCC

GGCTCTTTGAATTCTTTGACCGCACAGAGACAAGGACCAACTACCCCAATATGTTCAGGATTGGGAACTTGGTCTTG

TACATTCTCATCATCATCCACTGGAATGCCTGCATCTACTTTGCCATTTCCAAGTTCATTGGTTTTGGGACAGACTC

CTGGGTCTACCCAAACATCTCAATCCCAGAGCATGGGCGCCTCTCCAGGAAGTACATTTACAGTCTCTACTGGTCCA

CCTTGACCCTTACCACCATTGGTGAGACCCCACCCCCCGTGAAAGATGAGGAGTATCTCTTTGTGGTCGTAGACTTC

TTGGTGGGTGTTCTGATTTTTGCCACCATTGTGGGCAATGTGGGCTCCATGATCTCGAATATGAATGCCTCACGGGC

AGAGTTCCAGGCCAAGATTGATTCCATCAAGCAGTACATGCAGTTCCGCAAGGTCACCAAGGACTTGGAGACGCGGG

TTATCCGGTGGTTTGACTACCTGTGGGCCAACAAGAAGACGGTGGATGAGAAGGAGGTGCTCAAGAGCCTCCCAGAC

AAGCTGAAGGCTGAGATCGCCATCAACGTGCACCTGGACACGCTGAAGAAGGTTCGCATCTTCCAGGACTGTGAGGC

AGGGCTGCTGGTGGAGCTGGTGCTGAAGCTGCGACCCACTGTGTTCAGCCCTGGGGATTATATCTGCAAGAAGGGAG

ATATTGGGAAGGAGATGTACATCATCAACGAGGGCAAGCTGGCCGTGGTGGCTGATGATGGGGTCACCCAGTTCGTG

GTCCTCAGCGATGGCAGCTACTTCGGGGAGATCAGCATTCTGAACATCAAGGGGAGCAAGTCGGGGAACCGCAGGAC

GGCCAACATCCGCAGCATTGGCTACTCAGACCTGTTCTGCCTCTCAAAGGACGATCTCATGGAGGCCCTCACCGAGT

ACCCCGAAGCCAAGAAGGCCCTGGAGGAGAAAGGACGGCAGATCCTGATGAAAGACAACCTGATCGATGAGGAGCTG

GCCAGGGCGGGCGCGGACCCCAAGGACCTTGAGGAGAAAGTGGAGCAGCTGGGGTCCTCCCTGGACACCCTGCAGAC

CAGGTTTGCACGCCTCCTGGCTGAGTACAACGCCACCCAGATGAAGATGAAGCAGCGTCTCAGCCAACTGGAAAGCC

AGGTGAAGGGTGGTGGGGACAAGCCCCTGGCTGATGGGGAAGTTCCCGGGGATGCTACAAAAACAGAGGACAAACAA

CAGTGA codon-optimised CNGA3 cDNA

SEQ ID NO: 8

ATGGCAAAAATCAATACCCAGTACAGCCACCCCTCACGAACTCACCTGAAAGTCAAAACAAGCGATAGAGACCTGAA

CAGAGCCGAGAACGGCCTGTCCAGGGCCCACAGCTCCTCTGAGGAAACTAGTTCAGTGCTGCAGCCTGGAATCGCTA

TGGAGACCAGAGGGCTGGCTGACTCTGGCCAAGGAAGTTTCACAGGGCAGGGCATCGCCAGGCTGTCTAGACTGATT

TTTCTGCTGAGGAGATGGGCCGCTAGGCATGTGCACCATCAGGACCAGGGACCCGATAGTTTCCCTGAC

AGGTTCAGGGGGGCCGAACTGAAGGAGGTCAGCTCCCAGGAATCTAACGCACAGGCCAATGTGGGCAGTCAGGAGCC

CGCTGATAGAGGACGGTCCGCATGGCCTCTGGCCAAGTGCAACACTAATACCTCTAACAATACAGAGGAAGAGAAGA

AAACTAAGAAAAAGGATGCCATCGTGGTCGACCCTTCTAGTAACCTGTACTATAGGTGGCTGACAGCTATCGCACTG

CCAGTGTTCTACAATTGGTATCTGCTGATTTGCAGAGCTTGTTTTGACGAACTGCAGAGTGAGTATCTG

-continued

ATGCTGTGGCTGGTGCTGGATTACTCAGCAGACGTGCTGTATGTGCTGGATGTCCTGGTGCGCGCACGAACTGGGTT

CCTGGAGCAGGGCCTGATGGTGAGCGACACCAACAGACTGTGGCAGCACTACAAAACCACAACTCAGTTTAAGCTGG

ATGTCCTGTCCCTGGTGCCAACCGACCTGGCCTACCTGAAAGTCGGCACAAACTATCCCGAGGTGCGGTTCAATCGC

CTGCTGAAGTTCTCTCGGCTGTTTGAGTTCTTCGATAGGACAGAGACTAGAACCAACTACCCAAATATG

TTCCGCATCGGCAACCTGGTGCTGTATATTCTGATCATTATCCACTGGAATGCTTGTATCTACTTTGCAATCAGCAA

GTTCATTGGATTTGGGACCGACAGCTGGGTGTATCCAAACATTTCCATCCCCGAACATGGACGACTGAGCAGGAAGT

ACATCTATTCACTGTACTGGAGCACACTGACTCTGACCACAATTGGGGAGACCCCCCCTCCAGTGAAGGATGAAGAG

TACCTGTTCGTGGTCGTGGACTTTCTGGTCGGCGTGCTGATCTTCGCAACAATTGTCGGCAATGTGGGA

AGTATGATCTCAAACATGAATGCCTCACGAGCTGAGTTCCAGGCTAAAATTGACAGCATCAAGCAGTATATGCAGTT

TAGAAAAGTCACTAAGGATCTGGAGACCAGAGTGATCCGGTGGTTTGACTACCTGTGGGCCAACAAAAAGACAGTCG

ATGAAAAAGAGGTGCTGAAGAGCCTGCCCGACAAACTGAAGGCAGAGATTGCCATCAATGTCCATCTGGATACTCTG

AAAAAGGTGCGGATCTTCCAGGACTGCGAAGCAGGACTGCTGGTCGAGCTGGTGCTGAAGCTGCGCCCT

ACCGTGTTTAGCCCAGGCGATTATATCTGTAAAAAGGGGGACATTGGCAAAGAAATGTACATTATCAACGAGGGGAA

GCTGGCTGTCGTGGCAGACGATGGCGTGACCCAGTTCGTCGTGCTGAGCGATGGCAGCTATTTTGGGGAAATTTCCA

TCCTGAATATCAAAGGCTCCAAGTCTGGAAACCGGCGCACAGCTAATATTCGGTCCATCGGATATTCTGACCTGTTC

TGCCTGTCTAAGGACGATCTGATGGAGGCACTGACTGAATACCCCGAGGCCAAAAAGGCTCTGGAAGAG

AAAGGCCGGCAGATCCTGATGAAGGATAACCTGATTGACGAAGAGCTGGCACGAGCTGGAGCAGACCCTAAAGATCT

GGAAGAGAAGGTGGAGCAGCTGGGATCAAGCCTGGATACCCTGCAGACACGCTTCGCTCGACTGCTGGCAGAATACA

ATGCCACCCAGATGAAAATGAAGCAGCGCCTGAGTCAGCTGGAGTCACAGGTGAAAGGCGGAGGGGACAAGCCCCTG

GCAGATGGCGAAGTCCCTGGCGACGCTACAAAAACAGAAGATAAACAGCAGTAA

PDE6C cDNA, NM_006204.3

SEQ ID NO: 9

ATGGGTGAGATCAACCAAGTTGCCGTGGAGAAATACCTGGAGGAGAACCCTCAGTTTGCCAAGGAGTACTTTGACAG

GAAGTTGCGGGTGGAGGTGCTGGGAGAAATCTTCAAGAACAGCCAGGTGCCAGTCCAGTCCAGCATGTCCTTCTCTG

AGCTGACCCAGGTGGAGGAGTCAGCCCTGTGCTTGGAGCTGCTGTGGACCGTGCAGGAGGAGGGGGCACCCCAGAG

CAGGGGGTTCACAGGGCCCTGCAGAGGCTGGCCCACCTGCTCCAGGCTGACCGCTGCAGCATGTTCCTGTGCCGGTC

CCGGAACGGCATACCTGAGGTGGCCTCTAGGTTGCTGGATGTCACCCCCACCTCCAAGTTTGAGGACAACCTGGTGG

GCCCTGACAAAGAAGTTGTGTTTCCATTGGACATTGGGATAGTGGGTTGGGCTGCTCACACGAAGAAAACTCATAAT

GTCCCAGATGTGAAAAAGAACAGCCATTTTTCTGACTTCATGGACAAGCAAACTGGGTATGTCACTAAGAACCTGCT

GGCAACCCCGATCGTGGTGGGCAAGGAGGTTCTTGCTGTGATCATGGCAGTTAACAAAGTAAATGCATCTGAATTTT

CCAAACAGGATGAAGAGGTCTTTTCCAAATACCTCAACTTTGTGTCTATCATCCTAAGGCTTCATCACACCAGCTAC

ATGTACAATATTGAATCCCGAAGAAGCCAGATCCTTATGTGGTCAGCCAATAAAGTATTTGAAGAACTCACAGATGT

TGAGCGACAGTTTCACAAAGCGCTCTACACGGTTAGATCATATCTGAACTGTGAACGATACTCCATTGGACTGCTGG

ACATGACCAAGGAGAAGGAATTCTACGATGAATGGCCAATCAAGCTTGGAGAAGTAGAGCCTTATAAAGGTCCAAAG

ACACCTGATGGCAGGGAAGTCAACTTTTATAAAATCATTGATTACATTTTACATGGAAAAGAAGAGATCAAAGTGAT

TCCGACGCCTCCTGCAGACCACTGGACACTCATTAGTGGGTTGCCAACATATGTTGCTGAAAATGGATTTATCTGTA

ACATGATGAATGCCCCTGCGGATGAATACTTCACATTTCAGAAAGGACCTGTAGACGAAACTGGTTGGGTCATTAAG

AATGTTTTGTCCCTGCCTATTGTCAACAAGAAAGAAGATATTGTGGGAGTGGCTACATTTTACAACAGGAAGGATGG

AAAACCTTTCGATGAGCATGATGAATACATTACCGAGACTCTCACACAATTTCTTGGATGGTCTCTTTTAAATACTG

ACACCTACGATAAGATGAATAAGCTAGAAAACAGAAAGGACATTGCTCAGGAAATGCTCATGAACCAAACCAAAGCC

ACTCCTGAAGAAATTAAGTCCATTTTGAAATTTCAAGAGAAGTTAAATGTTGATGTAATTGACGACTGTGAAGAAAA

ACAACTTGTTGCAATTTTGAAAGAGGACTTGCCAGACCCACGCTCAGCAGAACTGTACGAATTCCGCTTCAGTGACT

-continued

TCCCCCTTACAGAGCACGGATTGATTAAATGTGGAATACGACTGTTTTTTGAAATAAATGTGGTGGAGAAATTCAAA

GTACCTGTAGAGGTTCTTACCAGATGGATGTACACTGTGAGGAAAGGGTACCGAGCTGTCACTTACCACAATTGGCG

GCATGGGTTCAACGTGGGGCAGACCATGTTTACTTTGCTGATGACAGGAAGATTAAAGAAGTACTACACAGATCTCG

AAGCCTTTGCCATGCTTGCTGCTGCTTTCTGCCATGATATTGACCACAGAGGCACCAATAATTTGTACCAGATGAAA

TCCACGTCTCCATTAGCAAGACTTCATGGTTCTTCTATTTTGGAGAGGCACCACCTGGAGTACAGTAAGACTCTGTT

GCAGGATGAGAGTTTAAACATCTTCCAGAACCTAAATAAGCGGCAGTTTGAAACAGTTATTCATTTGTTCGAGGTCG

CAATAATAGCAACTGACCTGGCTTTATATTTCAAGAAGAGGACCATGTTTCAAAAAATTGTTGATGCCTGTGAACAA

ATGCAAACGGAAGAAGAAGCCATCAAATATGTAACTGTTGATCCAACCAAGAAAGAGATTATCATGGCAATGATGAT

GACGGCATGTGACTTGTCTGCTATTACCAAGCCCTGGGAGGTGCAAAGTCAGGTAGCACTTATGGTTGCAAATGAAT

TTTGGGAACAAGGAGATCTGGAGAGAACAGTGTTGCAGCAACAACCCATTCCTATGATGGACAGAAACAAAAGAGAT

GAATTACCTAAACTTCAAGTTGGATTTATTGATTTTGTTTGTACTTTTGTATATAAGGAGTTCTCACGGTTTCACAA

AGAAATCACACCTATGCTGAGTGGTCTTCAGAATAACAGAGTAGAATGGAAATCACTAGCTGATGAGTATGATGCAA

AGATGAAGGTCATTGAAGAGGAGGCAAAAAAGCAAGAAGGAGGAGCCGAAAAAGCTGCTGAAGATTCAGGAGGTGGT

GATGACAAAAAGTCCAAAACATGTTTAATGTTGTAA

PDE6H cDNA, NM_006205.2

SEQ ID NO: 10

ATGAGTGACAACACTACTCTGCCTGCTCCAGCTTCAAACCAGGGTCCTACCACCCCACGCAAAGGCCCTCCCAAGTT

CAAGCAGAGGCAGACTCGCCAATTCAAGAGTAAACCTCCAAAGAAAGGTGTGAAAGGATTTGGAGATGACATTCCAG

GAATGGAGGGGCTAGGAACAGATATCACAGTGATTTGTCCATGGGAGGCATTCAGCCACCTGGAATTGCATGAGCTC

GCTCAGTTTGGGATTATCTGA

GNAT2 cDNA, NM_005272.3

SEQ ID NO: 11

ATGGGAAGTGGAGCCAGTGCTGAGGACAAAGAACTGGCCAAGAGGTCCAAGGAGCTAGAAAAGAAGCTGCAGGAGGA

TGCTGATAAGGAAGCCAAGACTGTCAAGCTGCTACTGCTGGGTGCTGGGGAGTCAGGAAAGAGCACCATCGTCAAAC

AGATGAAGATCATTCACCAGGATGGCTATTCACCAGAAGAATGCCTGGAGTTCAAGGCTATCATCTATGGAAATGTG

CTGCAGTCCATCCTGGCTATCATCCGGGCCATGACCACACTGGGCATCGATTATGCTGAACCAAGCTGTGCGGATGA

CGGGCGACAGCTCAACAACCTGGCTGACTCCATTGAGGAGGGAACCATGCCTCCTGAGCTCGTGGAGGTCATTAGGA

GGTTGTGGAAGGATGGTGGGGTGCAAGCCTGCTTCGAGAGAGCTGCAGAATACCAGCTTAATGACTCCGCATCTTAC

TACCTGAACCAATTAGAACGAATTACAGACCCTGAGTACCTCCCTAGTGAGCAAGATGTGCTCCGATCCAGAGTCAA

AACCACGGGCATCATTGAAACCAAGTTTTCCGTCAAAGACTTGAATTTCAGGATGTTTGATGTGGGAGGGCAGAGAT

CCGAGAGAAAGAAGTGGATCCACTGCTTCGAGGGAGTCACCTGCATCATTTTCTGTGCAGCCCTCAGTGCCTATGAT

ATGGTGCTGGTGGAAGATGACGAAGTGAATCGTATGCATGAGTCTTTGCATCTGTTCAACAGCATATGTAACCACAA

ATTCTTTGCGGCTACTTCCATTGTCCTCTTTCTCAACAAGAAGGACCTCTTTGAGGAAAAAATCAAGAAAGTCCATC

TCAGCATTTGTTTTCCAGAGTATGATGGTAACAACTCCTATGATGATGCGGGGAATTACATAAAGAGCCAGTTCCTT

GACCTCAATATGCGAAAAGATGTCAAAGAAATCTACAGTCACATGACCTGTGCTACAGATACACAGAATGTCAAATT

TGTGTTTGATGCAGTTACAGATATTATCATCAAAGAAAACCTCAAGGACTGCGGCCTCTTCTAA

KCNV2 cDNA, NM_133497.3

SEQ ID NO: 12

ATGCTCAAACAGAGTGAGAGGAGACGGTCCTGGAGCTACAGGCCCTGGAACACGACGGAGAATGAGGGCAGCCAACA

CCGCAGGAGCATTTGCTCCCTGGGTGCCCGTTCCGGCTCCCAGGCCAGCATCCACGGCTGGACAGAGGGCAACTATA

ACTACTACATCGAGGAAGACGAAGACGGCGAGGAGGAGGACCAGTGGAAGGACGACCTGGCAGAAGAGGACCAGCAG

GCAGGGGAGGTCACCACCGCCAAGCCCGAGGGCCCCAGCGACCCTCCGGCCCTGCTGTCCACGCTGAATGTGAACGT

GGGTGGCCACAGCTACCAGCTGGACTACTGCGAGCTGGCCGGCTTCCCCAAGACGCGCCTAGGTCGCCTGGCCACCT

-continued

CCACCAGCCGCAGCCGCCAGCTAAGCCTGTGCGACGACTACGAGGAGCAGACAGACGAATACTTCTTCGACCGCGAC

CCGGCCGTCTTCCAGCTGGTCTACAATTTCTACCTGTCCGGGGTGCTGCTGGTGCTCGACGGGCTGTGTCCGCGCCG

CTTCCTGGAGGAGCTGGGCTACTGGGGCGTGCGGCTCAAGTACACGCCACGCTGCTGCCGCATCTGCTTCGAGGAGC

GGCGCGACGAGCTGAGCGAACGGCTCAAGATCCAGCACGAGCTGCGCGCGCAGGCGCAGGTCGAGGAGGCGGAGGAA

CTCTTCCGCGACATGCGCTTCTACGGCCCGCAGCGGCGCCGCCTCTGGAACCTCATGGAGAAGCCATTCTCCTCGGT

GGCCGCCAAGGCCATCGGGGTGGCCTCCAGCACCTTCGTGCTCGTCTCCGTGGTGGCGCTGGCGCTCAACACCGTGG

AGGAGATGCAGCAGCACTCGGGGCAGGGCGAGGGCGGCCCAGACCTGCGGCCCATCCTGGAGCACGTGGAGATGCTG

TGCATGGGCTTCTTCACGCTCGAGTACCTGCTGCGCCTAGCCTCCACGCCCGACCTGAGGCGCTTCGCGCGCAGCGC

CCTCAACCTGGTGGACCTGGTGGCCATCCTGCCGCTCTACCTTCAGCTGCTGCTCGAGTGCTTCACGGGCGAGGGCC

ACCAACGCGGCCAGACGGTGGGCAGCGTGGGTAAGGTGGGTCAGGTGTTGCGCGTCATGCGCCTCATGCGCATCTTC

CGCATCCTCAAGCTGGCGCGCCACTCCACCGGACTGCGTGCCTTCGGCTTCACGCTGCGCCAGTGCTACCAGCAGGT

GGGCTGCCTGCTGCTCTTCATCGCCATGGGCATCTTCACTTTCTCTGCGGCTGTCTACTCTGTGGAGCACGATGTGC

CCAGCACCAACTTCACTACCATCCCCCACTCCTGGTGGTGGGCCGCGGTGAGCATCTCCACCGTGGGCTACGGAGAC

ATGTACCCAGAGACCCACCTGGGCAGGTTTTTTGCCTTCCTCTGCATTGCTTTTGGGATCATTCTCAACGGGATGCC

CATTTCCATCCTCTACAACAAGTTTTCTGATTACTACAGCAAGCTGAAGGCTTATGAGTATACCACCATACGCAGGG

AGAGGGGAGAGGTGAACTTCATGCAGAGAGCCAGAAAGAAGATAGCTGAGTGTTTGCTTGGAAGCAACCCACAGCTC

ACCCCAAGACAAGAGAATTAG

CACNA2D4 cDNA, NM_172364.4

SEQ ID NO: 13

ATGGTCTGTGGCTGCTCTGCCCTCCTTCCCCTCCCCAACCCCAGGCCCACCATGCCTGCAACTCCCAACTTCCTCGC

AAACCCCAGCTCCAGCAGCCGCTGGATTCCCCTCCAGCCAATGCCCGTGGCCTGGGCCTTTGTGCAGAAGACCTCGG

CCCTCCTGTGGCTGCTGCTTCTAGGCACCTCCCTGTCCCCTGCGTGGGGACAGGCCAAGATTCCTCTGGAAACAGTG

AAGCTATGGGCTGACACCTTCGGCGGGGACCTGTATAACACTGTGACCAAATACTCAGGCTCTCTCTTGCTGCAGAA

GAAGTACAAGGATGTGGAGTCCAGTCTGAAGATCGAGGAGGTGGATGGCTTGGAGCTGGTGAGGAAGTTCTCAGAGG

ACATGGAGAACATGCTGCGGAGGAAAGTCGAGGCGGTCCAGAATCTGGTGGAAGCTGCCGAGGAGGCCGACCTGAAC

CACGAATTCAATGAATCCCTGGTGTTCGACTATTACAACTCGGTCCTGATCAACGAGAGGGACGAGAAGGGCAACTT

CGTGGAGCTGGGCGCCGAGTTCCTCCTGGAGTCCAATGCTCACTTCAGCAACCTGCCGGTGAACACCTCCATCAGCA

GCGTGCAGCTGCCCACCAACGTGTACAACAAAGACCCAGATATTTTAAATGGAGTCTACATGTCTGAAGCCTTGAAT

GCTGTCTTCGTGGAGAACTTCCAGAGAGACCCAACGTTGACCTGGCAATATTTTGGCAGTGCAACTGGATTCTTCAG

GATCTATCCAGGTATAAAATGGACACCTGATGAGAATGGAGTCATTACTTTTGACTGCCGAAACCGCGGCTGGTACA

TTCAAGCTGCTACTTCTCCCAAGGACATAGTGATTTTGGTGGACGTGAGCGGCAGTATGAAGGGGCTGAGGATGACT

ATTGCCAAGCACACCATCACCACCATCTTGGACACCCTGGGGGAGAATGACTTCATTAATATCATAGCGTACAATGA

CTACGTCCATTACATCGAGCCTTGTTTTAAAGGGATCCTCGTCCAGGCGGACCGAGACAATCGAGAGCATTTCAAAC

TGCTGGTGGAGGAGTTGATGGTCAAAGGTGTGGGGGTCGTGGACCAAGCCCTGAGAGAAGCCTTCCAGATCCTGAAG

CAGTTCCAAGAGGCCAAGCAAGGAAGCCTCTGCAACCAGGCCATCATGCTCATCAGCGACGGCGCCGTGGAGGACTA

CGAGCCGGTGTTTGAGAAGTATAACTGGCCAGACTGTAAGGTCCGAGTTTTCACTTACCTCATTGGGAGAGAAGTGT

CTTTTGCTGACCGCATGAAGTGGATTGCATGCAACAACAAAGGCTACTACACGCAGATCTCAACGCTGGCGGACACC

CAGGAGAACGTGATGGAATACCTGCACGTGCTCAGCCGCCCCATGGTCATCAACCACGACCACGACATCATCTGGAC

AGAGGCCTACATGGACAGCAAGCTCCTCAGCTCGCAGGCTCAGAGCCTGACACTGCTCACCACTGTGGCCATGCCAG

TCTTCAGCAAGAAGAACGAAACGCGATCCCATGGCATTCTCCTGGGTGTGGTGGGCTCAGATGTGGCCCTGAGAGAG

CTGATGAAGCTGGCGCCCCGGTACAAGCTTGGAGTGCACGGATACGCCTTTCTGAACACCAACAATGGCTACATCCT

CTCCCATCCCGACCTCCGGCCCCTGTACAGAGAGGGGAAGAAACTAAAACCCAAACCTAACTACAACAGTGTGGATC

-continued

TCTCCGAAGTGGAGTGGGAAGACCAGGCTGAATCTCTGAGAACAGCCATGATCAATAGGGAAACAGGTACTCTCTCG

ATGGATGTGAAGGTTCCGATGGATAAAGGGAAGCGAGTTCTTTTCCTGACCAATGACTACTTCTTCACGGACATCAG

CGACACCCCTTTCAGTTTGGGGGTGGTGCTGTCCCGGGGCCACGGAGAATACATCCTTCTGGGGAACACGTCTGTGG

AAGAAGGCCTGCATGACTTGCTTCACCCAGACCTGGCCCTGGCCGGTGACTGGATCTACTGCATCACAGATATTGAC

CCAGACCACCGGAAGCTCAGCCAGCTAGAGGCCATGATCCGCTTCCTCACCAGGAAGGACCCAGACCTGGAGTGTGA

CGAGGAGCTGGTCCGGGAGGTGCTGTTTGACGCGGTGGTGACAGCCCCCATGGAAGCCTACTGGACAGCGCTGGCCC

TCAACATGTCCGAGGAGTCTGAACACGTGGTGGACATGGCCTTCCTGGGCACCCGGGCTGGCCTCCTGAGAAGCAGC

TTGTTCGTGGGCTCCGAGAAGGTCTCCGACAGGAAGTTCCTGACACCTGAGGACGAGGCCAGCGTGTTCACCCTGGA

CCGCTTCCCGCTGTGGTACCGCCAGGCCTCAGAGCATCCTGCTGGCAGCTTCGTCTTCAACCTCCGCTGGGCAGAAG

GACCAGAAAGTGCGGGTGAACCCATGGTGGTGACGGCAAGCACAGCTGTGGCGGTGACCGTGGACAAGAGGACAGCC

ATTGCTGCAGCCGCGGGCGTCCAAATGAAGCTGGAATTCCTCCAGCGCAAATTCTGGGCGGCAACGCGGCAGTGCAG

CACTGTGGATGGGCCGTGCACACAGAGCTGCGAGGACAGTGATCTGGACTGCTTCGTCATCGACAACAACGGGTTCA

TTCTGATCTCCAAGAGGTCCCGAGAGACGGGAAGATTTCTGGGGGAGGTGGATGGTGCTGTCCTGACCCAGCTGCTC

AGCATGGGGGTGTTCAGCCAAGTGACTATGTATGACTATCAGGCCATGTGCAAACCCTCGAGTCACCACCACAGTGC

AGCCCAGCCCCTGGTCAGCCCAATTTCTGCCTTCTTGACGGCGACCAGGTGGCTGCTGCAGGAGCTGGTGCTGTTCC

TGCTGGAGTGGAGTGTCTGGGGCTCCTGGTACGACAGAGGGGCCGAGGCCAAAAGTGTCTTCCATCACTCCCACAAA

CACAAGAAGCAGGACCCGCTGCAGCCCTGCGACACGGAGTACCCCGTGTTCGTGTACCAGCCGGCCATCCGGGAGGC

CAACGGGATCGTGGAGTGCGGGCCCTGCCAGAAGGTATTTGTGGTGCAGCAGATTCCCAACAGTAACCTCCTCCTCC

TGGTGACAGACCCCACCTGTGACTGCAGCATCTTCCCACCAGTGCTGCAGGAGGCGACAGAAGTCAAATATAATGCC

TCTGTCAAATGTGACCGGATGCGCTCCCAGAAGCTCCGCCGGCGACCAGACTCCTGCCACGCCTTCCATCCAGAGGA

GAATGCCCAGGACTGCGGCGGCGCCTCGGACACCTCAGCCTCGCCGCCCCTACTCCTGCTGCCTGTGTGTGCCTGGG

GGCTACTGCCCCAACTCCTGCGGTGA

CNGB3 cDNA, NM_019098.4

SEQ ID NO: 14

ATGTTTAAATCGCTGACAAAAGTCAACAAGGTGAAGCCTATAGGAGAGAACAATGAGAATGAACAAAGTTCTCGTCG

GAATGAAGAAGGCTCTCACCCAAGTAATCAGTCTCAGCAAACCACAGCACAGGAAGAAAACAAAGGTGAAGAGAAAT

CTCTCAAAACCAAGTCAACTCCAGTCACGTCTGAAGAGCCACACACCAACATACAAGACAAACTCTCCAAGAAAAAT

TCCTCTGGAGATCTGACCACAAACCCTGACCCTCAAAATGCAGCAGAACCAACTGGAACAGTGCCAGAGCAGAAGGA

AATGGACCCCGGGAAAGAAGGTCCAAACAGCCCACAAAACAAACCGCCTGCAGCTCCTGTTATAAATGAGTATGCCG

ATGCCCAGCTACACAACCTGGTGAAAAGAATGCGTCAAAGAACAGCCCTCTACAAGAAAAAGTTGGTAGAGGGAGAT

CTCTCCTCACCCGAAGCCAGCCCACAAACTGCAAAGCCCACGGCTGTACCACCAGTAAAAGAAAGCGATGATAAGCC

AACAGAACATTACTACAGGCTGTTGTGGTTCAAAGTCAAAAAGATGCCTTTAACAGAGTACTTAAAGCGAATTAAAC

TTCCAAACAGCATAGATTCATACACAGATCGACTCTATCTCCTGTGGCTCTTGCTTGTCACTCTTGCCTATAACTGG

AACTGCTGGTTTATACCACTGCGCCTCGTCTTCCCATATCAAACCGCAGACAACATACACTACTGGCTTATTGCGGA

CATCATATGTGATATCATCTACCTTTATGATATGCTATTTATCCAGCCCAGACTCCAGTTTGTAAGAGGAGGAGACA

TAATAGTGGATTCAAATGAGCTAAGGAAACACTACAGGACTTCTCCAAAATTTCAGTTGGATGTCGCATCAATAATA

CCATTTGATATTTGCTACCTCTTCTTTGGGTTTAATCCAATGTTTAGAGCAAATAGGATGTTAAAGTACACTTCATT

TTTTGAATTTAATCATCACCTAGAGTCTATAATGGACAAAGCATATATCTACAGAGTTATTCGAACAACTGGATACT

TGCTGTTTATTCTGCACATTAATGCCTGTGTTTATTACTGGGCTTCAAACTATGAAGGAATTGGCACTACTAGATGG

GTGTATGATGGGGAAGGAAACGAGTATCTGAGATGTTATTATTGGGCAGTTCGAACTTTAATTACCATTGGTGGCCT

ACCAGAACCACAAACTTTATTTGAAATTGTTTTTCAACTCTTGAATTTTTTTTCTGGAGTTTTTGTGTTCTCCAGTT

-continued

TAATTGGTCAGATGAGAGATGTGATTGGAGCAGCTACAGCCAATCAGAACTACTTCCGCGCCTGCATGGATGACACC

ATTGCCTACATGAACAATTACTCCATTCCTAAACTTGTGCAAAAGCGAGTTCGGACTTGGTATGAATATACATGGGA

CTCTCAAAGAATGCTAGATGAGTCTGATTTGCTTAAGACCCTACCAACTACGGTCCAGTTAGCCCTCGCCATTGATG

TGAACTTCAGCATCATCAGCAAAGTCGACTTGTTCAAGGGTTGTGATACACAGATGATTTATGACATGTTGCTAAGA

TTGAAATCCGTTCTCTATTTGCCTGGTGACTTTGTCTGCAAAAAGGGAGAAATTGGCAAGGAAATGTATATCATCAA

GCATGGAGAAGTCCAAGTTCTTGGAGGCCCTGATGGTACTAAAGTTCTGGTTACTCTGAAAGCTGGGTCGGTGTTTG

GAGAAATCAGCCTTCTAGCAGCAGGAGGAGGAAACCGTCGAACTGCCAATGTGGTGGCCCACGGGTTTGCCAATCTT

TTAACTCTAGACAAAAAGACCCTCCAAGAAATTCTAGTGCATTATCCAGATTCTGAAAGGATCCTCATGAAGAAAGC

CAGAGTGCTTTTAAAGCAGAAGGCTAAGACCGCAGAAGCAACCCCTCCAAGAAAAGATCTTGCCCTCCTCTTCCCAC

CGAAAGAAGAGACACCCAAACTGTTTAAAACTCTCCTAGGAGGCACAGGAAAAGCAAGTCTTGCAAGACTACTCAAA

TTGAAGCGAGAGCAAGCAGCTCAGAAGAAAGAAAATTCTGAAGGAGGAGAGGAAGAAGGAAAAGAAAATGAAGATAA

ACAAAAAGAAAATGAAGATAAACAAAAAGAAAATGAAGATAAAGGAAAAGAAAATGAAGATAAAGATAAAGGAAGAG

AGCCAGAAGAGAAGCCACTGGACAGACCTGAATGTACAGCAAGTCCTATTGCAGTGGAGGAAGAACCCCACTCAGTT

AGAAGGACAGTTTTACCCAGAGGGACTTCTCGTCAATCACTCATTATCAGCATGGCTCCTTCTGCTGAGGGCGGAGA

AGAGGTTCTTACTATTGAAGTCAAAGAAAAGGCTAAGCAATAA hG1.7(M8) construct, 1.2 kb M/L opsin LCR fragment, 500 bp M opsin fragment, UTR in italics, M8 mutation underlined

SEQ ID NO: 15

TAGGAATAGAAGGGTGGGTGCAGGAGGCTGAGGGGTGGGGAAAGGGCATGGGTGTTTCATGAGGACAGAGCTTCCGT

TTCATGCAATGAAAAGAGTTTGGAGACGGATGGTGGTGACTGGACTATACACTTACACACGGTAGCGATGGTACACT

TTGTATTATGTATATTTTACCACGATCTTTTTAAAGTGTCAAAGGCAAATGGCCAAATGGTTCCTTGTCCTATAGCT

GTAGCAGCCATCGGCTGTTAGTGACAAAGCCCCTGAGTCAAGATGACAGCAGCCCCCATAACTCCTAATCGGCTCTC

CCGCGTGGAGTCATTTAGGAGTAGTCGCATTAGAGACAAGTCCAACATCTAATCTTCCACCCTGGCCAGGGCCCCAG

CTGGCAGCGAGGGTGGGAGACTCCGGGCAGAGCAGAGGGCGCTGACATTGGGGCCCGGCCTGGCTTGGGTCCCTCTG

GCCTTTCCCCAGGGGCCCTCTTTCCTTGGGGCTTTCTTGGGCCGCCACTGCTCCCGCTCCTCTCCCCCCATCCCACC

CCCTCACCCCCTCGTTCTTCATATCCTTCTCTAGTGCTCCCTCCACTTTCATCCACCCTTCTGCAAGAGTGTGGGAC

CACAAATGAGTTTTCACCTGGCCTGGGGACACACGTGCCCCCACAGGTGCTGAGTGACTTTCTAGGACAGTAATCTG

CTTTAGGCTAAAATGGGACTTGATCTTCTGTTAGCCCTAATCATCAATTAGCAGAGCCGGTGAAGGTGCAGAACCTA

CCGCCTTTCCAGGCCTCCTCCCACCTCTGCCACCTCCACTCTCCTTCCTGGGATGTGGGGGCTGGCACACGTGTGGC

CCAGGGCATTGGTGGGATTGCACTGAGCTGGGTCATTAGCGTAATCCTGGACAAGGGCAGACAGGGCGAGCGGAGGG

CCAGCTCCGGGGCTCAGGCAAGGCTGGGGGCTTCCCCCAGACACCCCACTCCTCCTCTGCTGGACCCCCACTTCATA

GGGCACTTCGTGTTCTCAAAGGGCTTCCAAATAGCATGGTGGCCTTGGATGCCCAGGGAAGCCTCAGAGTTGCTTAT

CTCCCTCTAGACAGAAGGGGAATCTCGGTCAAGAGGGAGAGGTCGCCCTGTTCAAGGCCACCCAGCCAGCTCATGGC

GGTAATGGGACAAGGCTGGCCAGCCATCCCACCCTCAGAAGGGACCCGGTGGGGCAGGTGATCTCAGAGGAGGCTCA

CTTCTGGGTCTCACATTCTTGGATCACAGGTATTTGCCACTAAGCCCAGCTAATTGTTTTTTATTTAGTAGAAACGG

GGTTTCACCATGTTAGTCAGGCTGGTCGGGAACTCCTGACCTCAGGAGATCTACCCGCCTTGGCCTCCCAAAGTGCT

GGGATTACAGGCGTGTGCCACTGTGCCCAGCCACTTTTTTTTAGACAGAGTCTTGGTCTGTTGCCCAGGCTAGAGTT

CAGTGGCGCCATCTCAGCTCACTGCAACCTCCGCCTCCCAGATTCAAGCGATTCTCCTGCCTCGACCTCCCAGTAGC

TGGGATTACAGGTTTCCAGCAAATCCCTCTGAGCCGCCCCCGGGGGCTCGCCTCAGGAGCAAGGAAGCAAGGGGTGG

GAGGAGGAGGTCTAAGTCCCAGGCCCAATTAAGAGATCAGATGGTGTAGGATTTGGGAGCTTTTAAGGTGAAGAGGC

CCGGGCTGATCCCACTGGCCGGTATAAAGCACCGTGACCCTCAGGTGACGCA*CCATCTAGAGCTGCCGTCGGGGACA*

*GGGCTTTCCATAGCC*

-continued

M8 mutation

SEQ ID NO: 16

TCTAGA

SEQ ID NO: 2 2- 2.0 kb M opsin promoter fragment, 500 bp fragment of
SEQ ID NO: 3 underlined, UTR in italics, M8 mutation underlined

SEQ ID NO: 17

TAAAAAGCAAGTCTTGCCAGGGCAGTGGTGTGCACCTGTGGTCCCAGCTACTCAGGATGCTGAGGCAGGAGGATTAC

TTGTGCCCAGCAAGTAGAGGCTGCAGTGACCTGTGACTGTGCTACTGCCCTCCAACCTGGGTGACAGAGTGAGACCT

TGTCTCAAAAAAAAAAAGAGCGGGGGGGGGGGGCCGGGCCGGGCGTGGTGGCTCACAGCTGTAATCCCAGCACTTTGG

GAAGCCAAGGCGGGTGGATCACTTGAGGTCAGGAGTTTGAGACCATCATGGTCAACACTGCGAAACACTGTCCCTAC

TAAAAATACAAAAATTAGCCGGGCATGGTGGCACACACCTGTAATCCCAGCTACTGGGGAGGCTGAGGCAGGAGAAT

TGCTTGAGCCGGGGAGACGGAGGTTGCAGTGAGCCGAGACTGCGCCACTGCACTCCAGCCTGACTGACAAGAGTGAG

ATTGTCTCAAAAAAAAAAAAAAAGTAATCACTAGAAAAGAAGCTACATATGTACATAACATCCAAATAACCAAGAGG

AGAAAAAAAATGGGACTTGATTAATCAAAACAAAAACAAAAAAGAAAGAAAGAAAGGGGGAGAAAATAAAACAAGGGC

TGGGTGTGCTGGCTCATGCCTGTAATCCCAGCACTTTGGAAGCCAAGGTGGGTGGATCTCTTGAGCTCAGGAGGTCA

AGACCAGCCTGGGCAACATGGCGAAACCCCGTCTCTATTAAAAAAAAAATTAATACAACAATTATCCTGGAGTGGTG

GTGCACACCTGTAGTCCCAGCTACCCAGGACGCTGAGACGGGAGGATCGCTTGATCCCGGGGATGTCGAGGCTGCCG

TGATCGCACCACTGCCCTCCAGCCAGGGTGGCAGACTGAGACCCCATCTCAAAAAATAAATAAATAAAAGCAAACAA

GAAAAAAAAAGGCTTGAAACATATCTGATAGATAAAGGGCTAATCAACACAATATATAAAGAACTGCAAATCAGTAA

ACTAAGAGCAAATAACCCAATATAAAGACATTAAAGGGTAGCCACGGACATCTCAGACGACGAAAAACAAAAGACAG

TAAACGTATAATAAAACATGTAATTGCAAGGTGATCCGGGAATAGTAAGCGAAAAGCAACAATTAAATACTATTTTC

TCATCCACCAGAACGCCAAAAATTAAAAAGCCTAACAATGTCCAGGGCTGGCGAGAATGTGGCAGAAGGTGATGTCA

CATACCCTGCAAGTGGGAATCTAAACAGATTCAGGGTTTTGGTTTTTTTTTAATCGCAATTAGGTGGCCTGTTAAAT

TTTTTTTCTTGAGACAGAGTTTTGCTCTTGTTGCCCAGGCTGGAGTGCAATGGCTCGATCTTGGCTCACCGCAACCT

CGACCTCCCAGGTACAAGCGATTCTCCTGTCTCAGCCTCCCAAGTAGCTGGGAGTACAGGTATTTGCCACTAAGCCC

AGCTAATTGTTTTTTATTTAGTAGAAACGGGGTTTCACCATGTTAGTCAGGCTGGTCGGGAACTCCTGACCTCAGGA

GATCTACCCGCCTTGGCCTCCCAAAGTGCTGGGATTACAGGCGTGTGCCACTGTGCCCAGCCACTTTTTTTTAGACA

GAGTCTTGGTCTGTTGCCCAGGCTAGAGTTCAGTGGCGCCATCTCAGCTCACTGCAACCTCCGCCTCCCAGATTCAA

GCGATTCTCCTGCCTCGACCTCCCAGTAGCTGGGATTACAGGTTTCCAGCAAATCCCTCTGAGCCGCCCCCGGGGGC

TCGCCTCAGGAGCAAGGAAGCAAGGGGTGGGAGGAGGAGGTCTAAGTCCCAGGCCCAATTAAGAGATCAGATGGTGT

AGGATTTGGGAGCTTTTAAGGTGAAGAGGCCCGGGCTGATCCCACTGGCCGGTATAAAGCACCGTGACCCTCAGGTG

ACGCA*CCATCTAGAGCTGCCGTCGGGGACAGGGCTTTCCATAGCC*

---

The invention claimed is:

1. A transcriptional control unit (TCU) of up to 2500 nucleotides in length comprising in a 5' to 3' direction:
(a) a Locus Control Region (LCR) comprising
(i) SEQ ID NO: 1; or
(ii) a sequence having at least 90% sequence identity to said sequence (a)(i); and
(b) a promoter element comprising SEQ ID NO: 16 and
(i) at least the last 200 nucleotides but no more than 1100 nucleotides of SEQ ID NO: 17; or
(ii) a sequence having at least 90% sequence identity to said sequence (b)(i).

2. The TCU of claim 1, wherein (b) comprises:
(i) at least the last 500 nucleotides SEQ ID NO: 17, or
(ii) a sequence having at least 90% sequence identity to said sequence (i).

3. The TCU of claim 1, wherein (b) comprises at least 200 nucleotides of SEQ ID NO: 3.

4. The TCU of claim 1, wherein the sequence of (b)(i) comprises a sequence of at least 10 contiguous nucleotides selected from nucleotides 1442 to 1476 of SEQ ID NO:17, or wherein the sequence of (b)(ii) comprises a sequence comprising at least 10 contiguous nucleotides selected from a sequence having at least 90% sequence identity to nucleotides 1442 to 1476 of SEQ ID NO:17.

5. The TCU according to claim 1, wherein (b) comprises:
(i) SEQ ID NO: 3; or
(ii) a sequence having at least 90% sequence identity to said sequence (i).

6. The TCU of claim 5, wherein the TCU comprises SEQ ID NO: 4 or SEQ ID NO: 15.

7. The TCU of claim 1, wherein the promoter element comprises SEQ ID NO: 5.

8. The TCU of claim 7, wherein the TCU comprises SEQ ID NO: 6.

9. An expression construct comprising the TCU of claim 1, wherein the TCU is operably linked to a gene sequence to be expressed.

10. The expression construct according to claim 9, wherein the operably linked gene sequence is CNGA3, CNGB3, PDE6C, PDE6H, GNAT2, KCNV2 or CACNA2D4.

11. The expression construct according to claim 10, wherein the operably linked gene sequence comprises SEQ ID NO: 7, 8, 9, 10, 11, 12, 13 or 14, or that has at least 80% sequence identity to SEQ ID NO: 7, 8, 9, 10, 11, 12, 13 or 14 and has the ability to rescue cone photoreceptor function.

12. The expression construct according to claim 10, wherein the operably linked gene sequence comprises SEQ ID NO: 8, or that has at least 80% sequence identity to SEQ ID NO: 8 and has the ability to rescue cone photoreceptor function.

13. A vector comprising the TCU according to claim 1.

14. The vector according to claim 13, wherein the vector is a viral vector.

15. The vector according to claim 14, wherein the vector is an adeno-associated virus (AAV) vector.

16. The vector according to claim 15, wherein the vector comprises an AAV genome or a derivative thereof.

17. The vector according to claim 16, wherein the AAV comprises a capsid that is derived from AAV8.

18. The vector according to claim 17, wherein the TCU is operably linked to a gene sequence to be expressed.

19. The vector according to claim 18, wherein the operably linked gene sequence is CNGA3.

20. The vector according to claim 16, wherein said derivative is a chimeric, shuffled or capsid modified derivative.

21. The vector according to claim 16, wherein said AAV genome is from a naturally derived serotype or isolate or clade of AAV.

22. The vector according to claim 21, wherein said AAV genome is from AAV serotype 2 (AAV2), AAV serotype 4 (AAV4), or AAV serotype 8 (AAV8).

23. The vector according to claim 22, wherein the genome is derived from AAV2.

24. An isolated host cell that contains the vector of claim 13.

25. The isolated host cell according to claim 24 that is a HEK293 or HEK293T cell.

26. A pharmaceutical composition comprising the vector of claim 13 and a pharmaceutically acceptable carrier.

27. A method of treating a retinal disorder in a patient in need thereof, comprising administering a therapeutically effective amount of the vector according to claim 13 to said patient.

28. The method of claim 27, wherein the retinal disorder is Achromatopsia.

29. The method of claim 27, wherein the treatment is by administration of the vector to a patient by direct retinal, subretinal or intravitreal injection.

30. The method according to claim 27, wherein said vector is administered directly into the retinal, subretinal space or intravitreal space.

31. A vector comprising the expression construct according to claim 9.

32. The vector according to claim 31, wherein the vector is a viral vector.

33. The vector according to claim 32, wherein the vector is an AAV vector.

34. The vector according to claim 33, wherein the vector comprises an AAV genome or a derivative thereof.

35. The vector according to claim 34, wherein the AAV comprises a capsid that is derived from AAV8.

36. The vector according to claim 35, wherein said AAV genome is from AAV serotype 2 (AAV2), AAV serotype 4 (AAV4), or AAV serotype 8 (AAV8).

37. The vector according to claim 36, wherein the genome is derived from AAV2.

38. The vector according to claim 37, wherein the operably linked gene sequence is CNGA3.

39. An isolated host cell that produces the viral vector of claim 13.

40. The isolated host cell according to claim 39, wherein the cell is a HEK293 or HEK293T cell.

41. The expression construct of claim 9, wherein the TCU comprises SEQ ID NO: 4 and wherein the TCU is operably linked to SEQ ID NO: 8.

42. The expression construct according to claim 9, wherein the operably linked gene sequence is CNGA3 and the TCU comprises SEQ ID NO: 15.

* * * * *